(12) United States Patent
Olson et al.

(10) Patent No.: US 11,684,754 B2
(45) Date of Patent: *Jun. 27, 2023

(54) METHOD OF STABILIZING CATHETER TUBE USING STABILIZING DEVICE

(71) Applicant: Levity Products, Inc., Mahtomedi, MN (US)

(72) Inventors: Sarah L. Olson, Hugo, MN (US); Carl B. Kieranen, Toivola, MI (US); John R. Mack, Mahotomedi, MN (US); Jason P. Mack, Houghton, MI (US)

(73) Assignee: Levity Products, Inc., Mahtomedi, MN (US)

( * ) Notice: Subject to any disclaimer, the term of this patent is extended or adjusted under 35 U.S.C. 154(b) by 508 days.

This patent is subject to a terminal disclaimer.

(21) Appl. No.: 15/929,464

(22) Filed: May 4, 2020

(65) Prior Publication Data
US 2020/0261700 A1    Aug. 20, 2020

Related U.S. Application Data

(63) Continuation of application No. 16/148,202, filed on Oct. 1, 2018, now Pat. No. 10,639,453, which is a
(Continued)

(51) Int. Cl.
*A61M 25/02* (2006.01)
*A61M 27/00* (2006.01)

(52) U.S. Cl.
CPC ............ *A61M 25/02* (2013.01); *A61M 27/00* (2013.01); *A61M 2025/024* (2013.01);
(Continued)

(58) Field of Classification Search
CPC ............ A61M 25/02; A61M 2025/024; A61M 2025/0266; A61M 2025/028;
(Continued)

(56) References Cited

U.S. PATENT DOCUMENTS

| 3,444,861 A | 5/1969 | Schulte |
| 4,050,461 A | 9/1977 | Ruby |

(Continued)

FOREIGN PATENT DOCUMENTS

| EP | 0228826 A2 | 7/1987 |
| JP | 649656 | 1/1989 |

(Continued)

OTHER PUBLICATIONS

European Extended Search Report dated Jul. 14, 2020 from corresponding European Patent Application No. 17841192.2.
(Continued)

*Primary Examiner* — Katherine H Schwiker
*Assistant Examiner* — Hong-Van N Trinh
(74) *Attorney, Agent, or Firm* — Honigman LLP

(57) ABSTRACT

A method of stabilizing a tube at a stoma of a patient includes providing a stabilizing device having a base portion and a tube holding portion that is attached at the base portion via at least two legs and that, with the base portion affixed to the patient, is spaced from the stoma of the patient. The tube holding portion has a passageway therethrough that is configured to receive the tube that passes through the stoma. The tube holding portion may be adjusted to position the tube in a free-flow orientation or a restricted-flow orientation. The tube holding portion may include a disinfecting wiping element. The stabilizing device may have pads coupled to respective legs via an elastomeric connecting element to allow for adjustment of the pads relative to the legs. The tube holding portion may include flexible tabs that deflect to enlarge an effective diameter of the passageway.

22 Claims, 42 Drawing Sheets

Related U.S. Application Data continuation of application No. 15/680,704, filed on Aug. 18, 2017, now Pat. No. 10,086,168.

(60) Provisional application No. 62/501,988, filed on May 5, 2017, provisional application No. 62/442,566, filed on Jan. 5, 2017, provisional application No. 62/377,098, filed on Aug. 19, 2016.

(52) U.S. Cl.
CPC .............. *A61M 2025/028* (2013.01); *A61M 2025/0266* (2013.01); *A61M 2025/0286* (2013.01); *A61M 2025/0293* (2013.01); *A61M 2210/1085* (2013.01)

(58) Field of Classification Search
CPC .. A61M 2025/0293; A61M 2039/0282; A61M 39/16–165
See application file for complete search history.

(56) References Cited

U.S. PATENT DOCUMENTS

| | | | |
|---|---|---|---|
| 4,170,995 A | 10/1979 | Levine et al. | |
| 4,360,025 A | 11/1982 | Edwards | |
| 4,392,854 A | 7/1983 | Ibach | |
| 4,397,647 A | 8/1983 | Gordon | |
| 4,435,174 A | 3/1984 | Redmond et al. | |
| D287,166 S | 12/1986 | Lipsky et al. | |
| 4,645,492 A | 2/1987 | Weeks | |
| 4,660,555 A | 4/1987 | Payton | |
| 4,769,010 A * | 9/1988 | Fenton, Jr. ............... | A61M 5/46 128/DIG. 26 |
| 4,820,274 A | 4/1989 | Choksi et al. | |
| 5,052,411 A | 10/1991 | Schoolman | |
| 5,069,206 A | 12/1991 | Crosbie | |
| 5,196,019 A | 3/1993 | Davis et al. | |
| D337,383 S | 7/1993 | Smith | |
| D339,864 S | 9/1993 | Stern | |
| D342,134 S | 12/1993 | Mongeon | |
| 5,267,969 A | 12/1993 | Hirsch et al. | |
| 5,318,581 A | 6/1994 | Sunmo | |
| D349,765 S | 8/1994 | Russo | |
| 5,352,211 A | 10/1994 | Merskelly | |
| D363,778 S | 10/1995 | Cane et al. | |
| D364,457 S | 11/1995 | Mongeon | |
| 5,685,859 A | 11/1997 | Kornerup | |
| 5,690,616 A | 11/1997 | Mogg | |
| 5,693,032 A | 12/1997 | Bierman | |
| 5,916,200 A | 6/1999 | Eppley et al. | |
| 5,944,696 A | 8/1999 | Bayless et al. | |
| 6,074,368 A | 6/2000 | Wright | |
| 6,213,979 B1 | 4/2001 | Bierman | |
| 6,361,523 B1 | 3/2002 | Bierman | |
| 6,387,076 B1 | 5/2002 | Landuyt | |
| 6,413,240 B1 | 7/2002 | Bierman et al. | |
| 6,428,514 B1 | 8/2002 | Goebel et al. | |
| D462,443 S | 9/2002 | Webb | |
| 6,582,403 B1 | 6/2003 | Bierman et al. | |
| 6,663,600 B2 | 12/2003 | Bierman et al. | |
| 7,344,512 B2 | 3/2008 | Yamazaki et al. | |
| 7,563,251 B2 | 7/2009 | Bierman et al. | |
| 7,762,991 B2 | 7/2010 | Bierman et al. | |
| 7,837,655 B2 | 11/2010 | Bierman et al. | |
| 7,922,697 B2 | 4/2011 | Beran | |
| 7,935,084 B2 | 5/2011 | Bierman | |
| 7,947,021 B2 | 5/2011 | Bourne et al. | |
| 7,955,307 B2 | 6/2011 | Bierman et al. | |
| 7,985,205 B2 | 7/2011 | Adams | |
| 8,025,643 B2 | 9/2011 | Bierman | |
| 8,052,649 B2 | 11/2011 | Wright | |
| 8,298,191 B2 | 10/2012 | Bierman et al. | |
| 8,308,740 B2 | 11/2012 | Tolley et al. | |
| 8,394,065 B2 | 3/2013 | Bierman | |
| 8,398,599 B2 | 3/2013 | Bierman | |
| 8,540,680 B2 | 9/2013 | Burn | |
| 8,636,699 B2 | 1/2014 | Russo | |
| 8,684,976 B2 | 4/2014 | Bierman et al. | |
| 8,734,401 B2 | 5/2014 | Beran | |
| 8,740,876 B2 | 6/2014 | Aguirre et al. | |
| 8,771,231 B2 | 7/2014 | Makino et al. | |
| 8,900,195 B2 | 12/2014 | Delegge et al. | |
| 8,936,025 B2 | 1/2015 | Flagler et al. | |
| 9,056,186 B2 | 6/2015 | Wright et al. | |
| D757,935 S | 5/2016 | Solingen et al. | |
| 9,526,871 B2 | 12/2016 | Wright et al. | |
| 9,638,354 B1 | 5/2017 | Ogueli et al. | |
| 9,642,987 B2 | 5/2017 | Bierman et al. | |
| 9,642,988 B2 | 5/2017 | Mizoguchi et al. | |
| D811,604 S | 2/2018 | Hashimoto et al. | |
| D814,026 S | 3/2018 | Darras et al. | |
| 9,974,929 B2 | 5/2018 | Ciccone et al. | |
| 10,034,971 B2 | 7/2018 | Abu-Sultaneh et al. | |
| 10,086,168 B2 | 10/2018 | Olson et al. | |
| 10,092,729 B2 | 10/2018 | Beran | |
| 10,639,453 B2 | 5/2020 | Olson et al. | |
| 2001/0011164 A1 | 8/2001 | Bierman | |
| 2002/0103481 A1 | 8/2002 | Webb et al. | |
| 2005/0267373 A1 | 12/2005 | Lee | |
| 2007/0149878 A1 | 6/2007 | Hankins | |
| 2008/0249476 A1 | 10/2008 | Bierman et al. | |
| 2008/0300546 A1 * | 12/2008 | Godara ................. | A61M 25/02 604/174 |
| 2009/0157000 A1 | 6/2009 | Waller | |
| 2011/0218498 A1 | 9/2011 | Bierman et al. | |
| 2012/0046515 A1 | 2/2012 | Woo et al. | |
| 2014/0018778 A1 | 1/2014 | Lopera et al. | |
| 2014/0276543 A1 | 9/2014 | Beran | |
| 2014/0364880 A1 | 12/2014 | Farnan et al. | |
| 2016/0074285 A1 | 3/2016 | Thomas | |
| 2016/0296725 A1 | 10/2016 | Calco | |
| 2019/0030289 A1 | 1/2019 | Olson et al. | |

FOREIGN PATENT DOCUMENTS

| | | |
|---|---|---|
| JP | 2015536200 A | 12/2015 |
| WO | 2006050080 A2 | 5/2006 |
| WO | 2007013202 A1 | 2/2007 |
| WO | 2016141291 A1 | 9/2016 |

OTHER PUBLICATIONS

International Search Report dated Oct. 30, 2017 for corresponding PCT Application No. PCT/IB2017/055021.

* cited by examiner

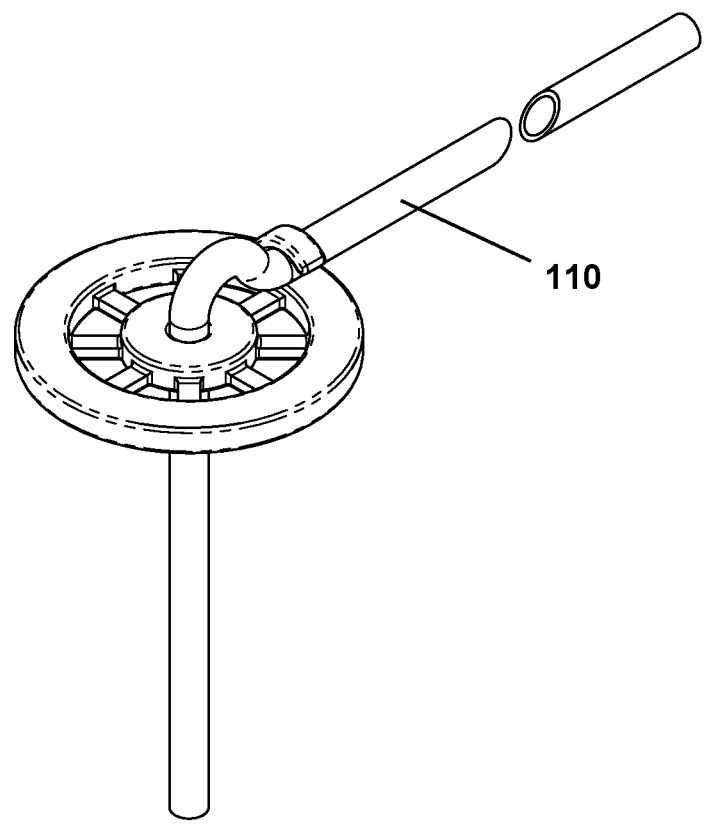
110
Fig. 6
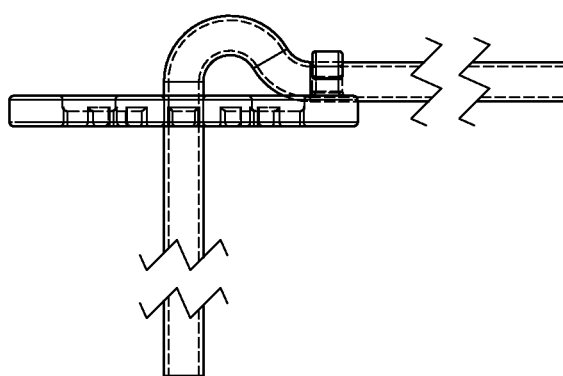
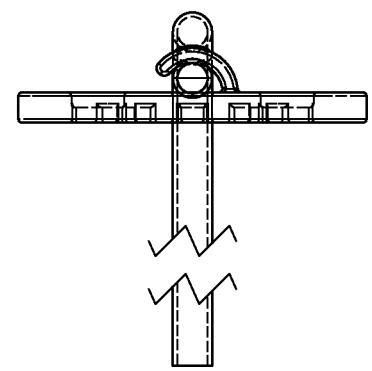
Fig. 6A Fig. 6B

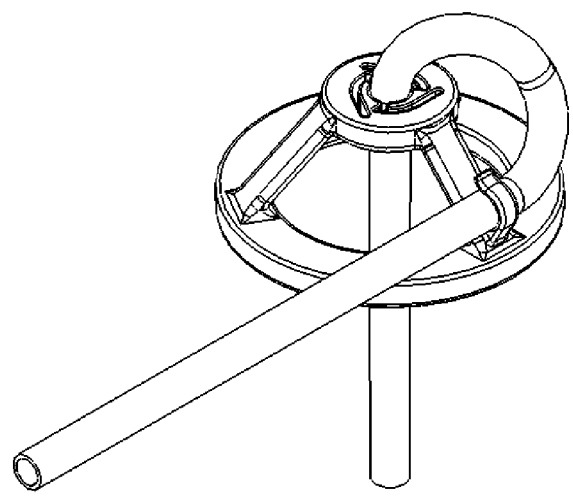
Fig. 11
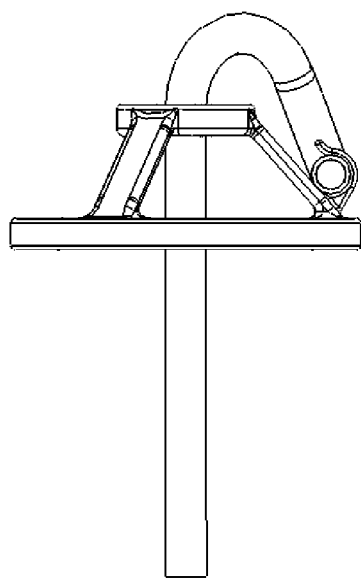
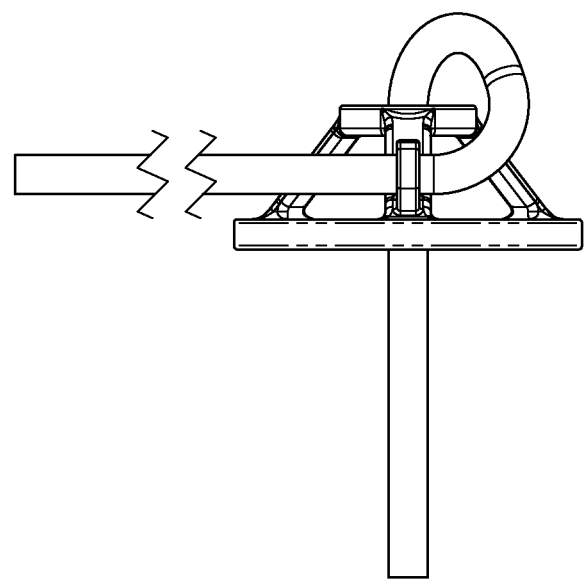
Fig. 11A  Fig. 11B

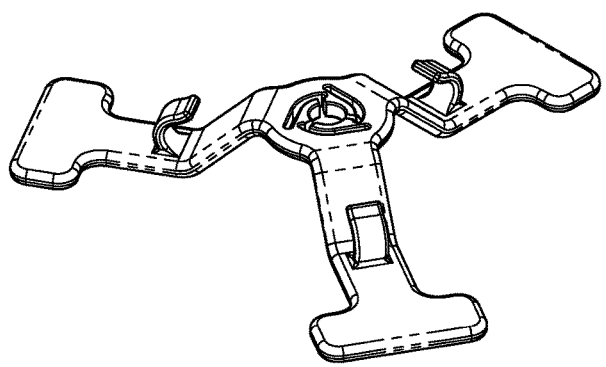
Fig. 22
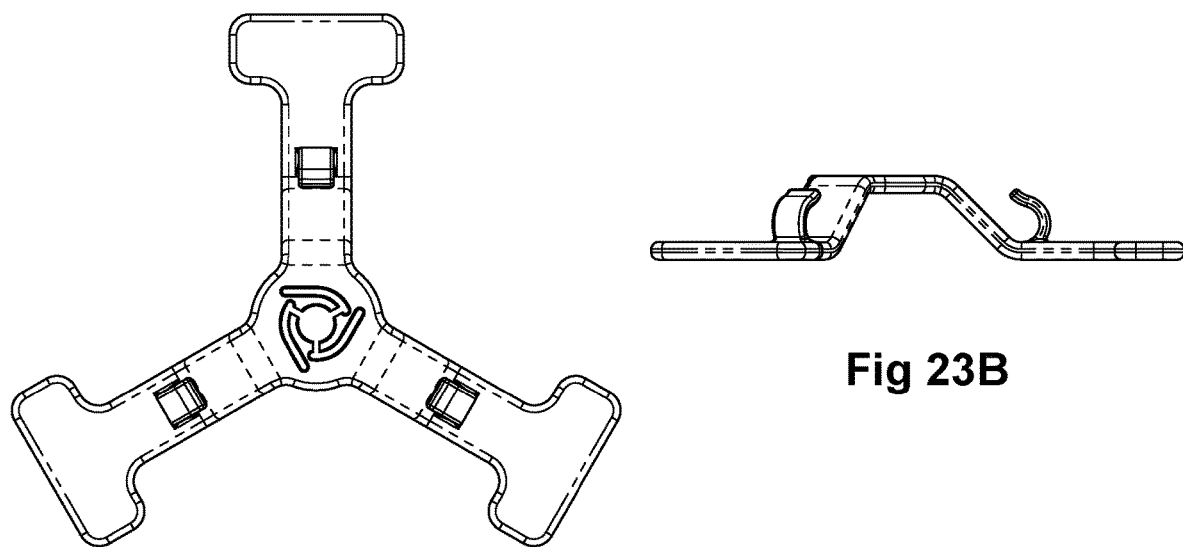
Fig 23B
Fig. 23
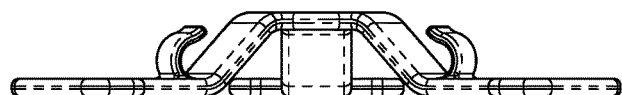
Fig 23A

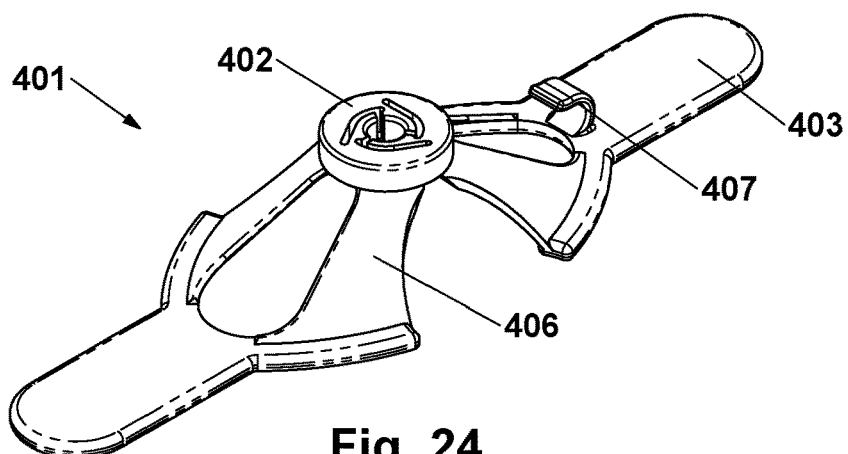
Fig. 24
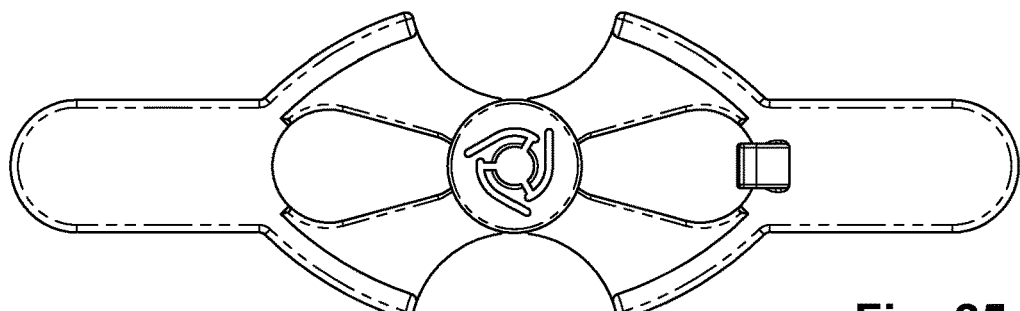
Fig. 25
Fig. 25B
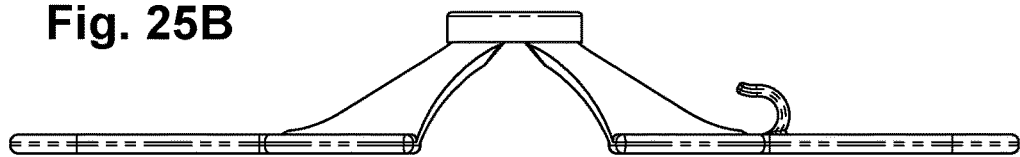
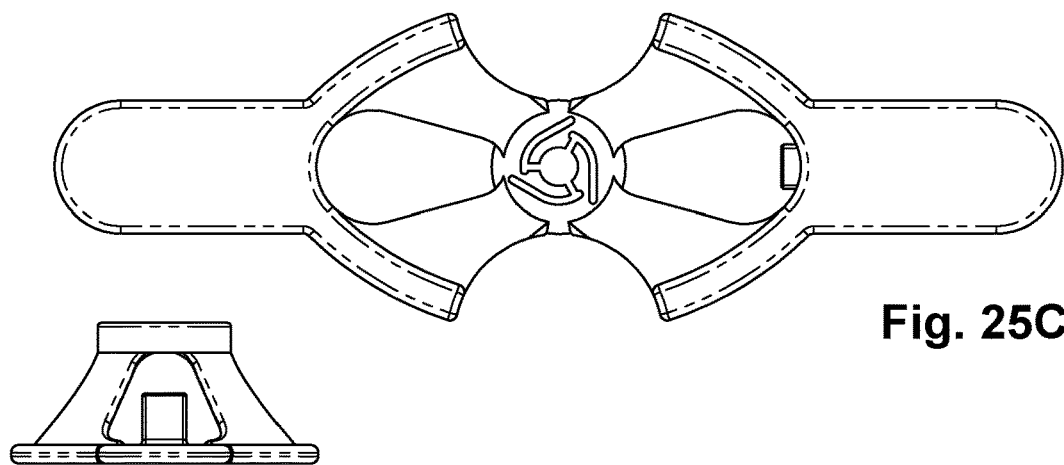
Fig. 25C
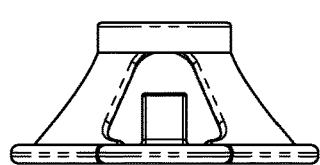
Fig. 25A

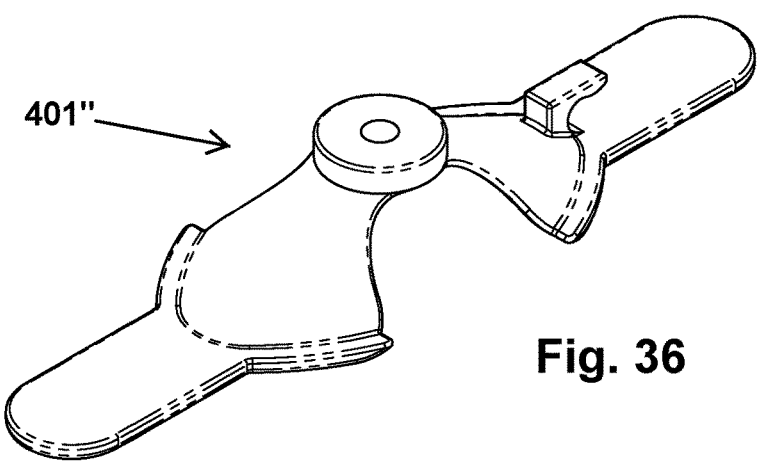
Fig. 36
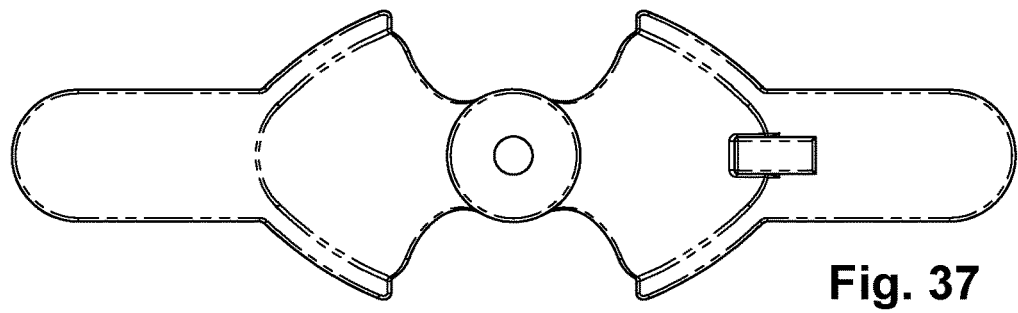
Fig. 37
Fig. 37B
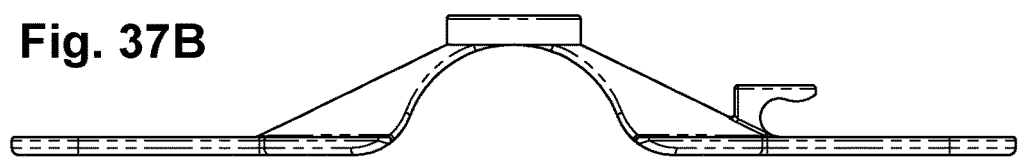
Fig. 37C
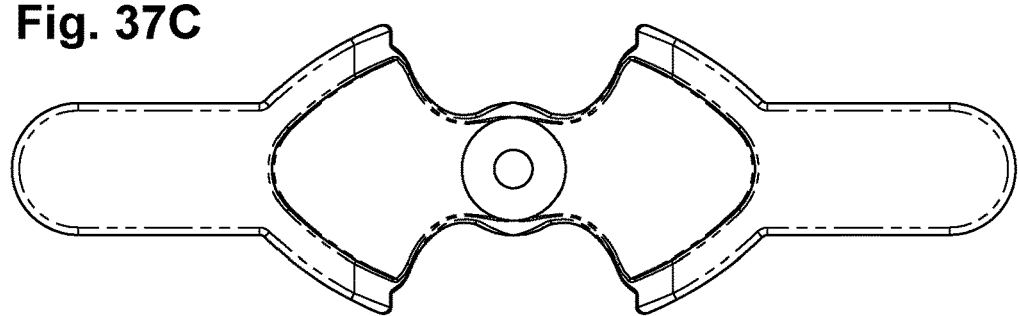
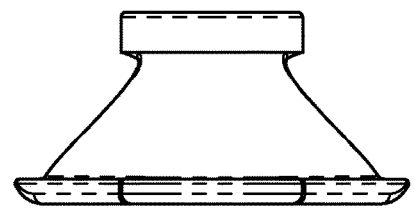
Fig. 37A

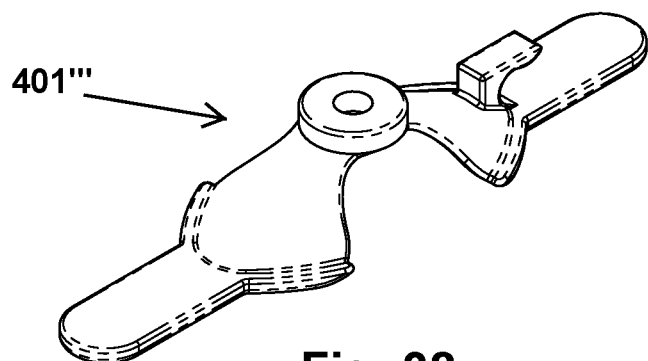
Fig. 38
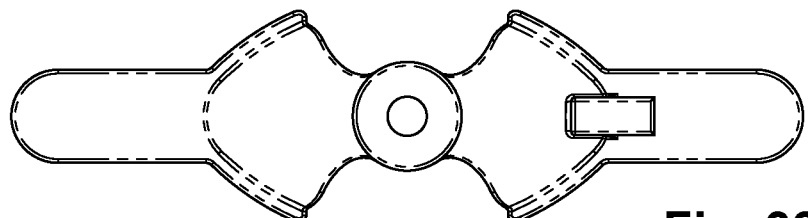
Fig. 39
Fig. 39B
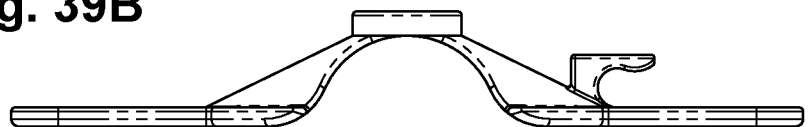
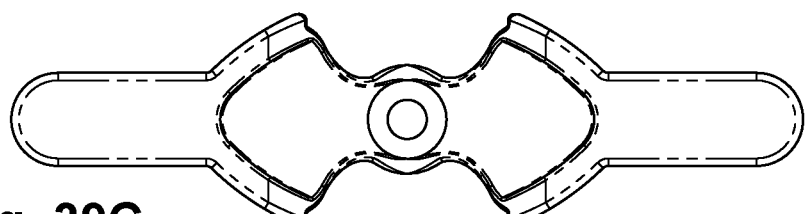
Fig. 39C
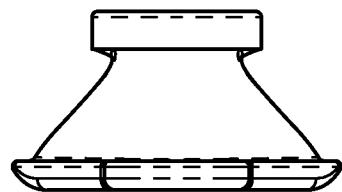
Fig. 39A

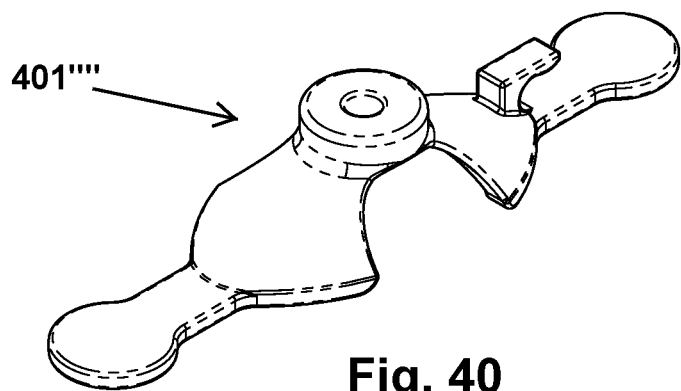
Fig. 40
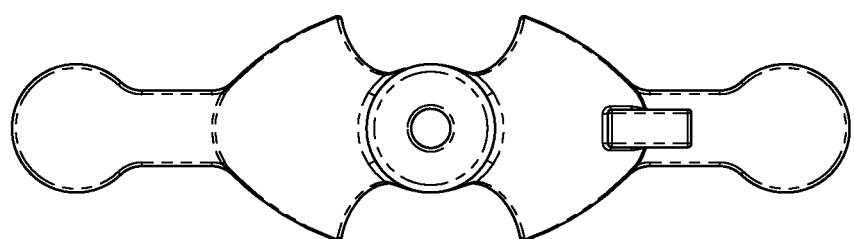
Fig. 41
Fig. 41B
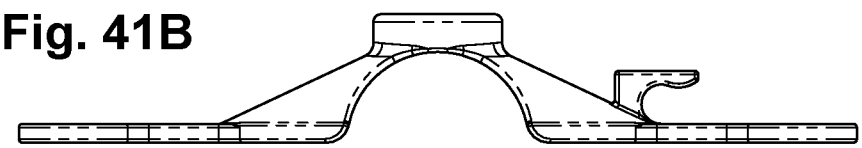
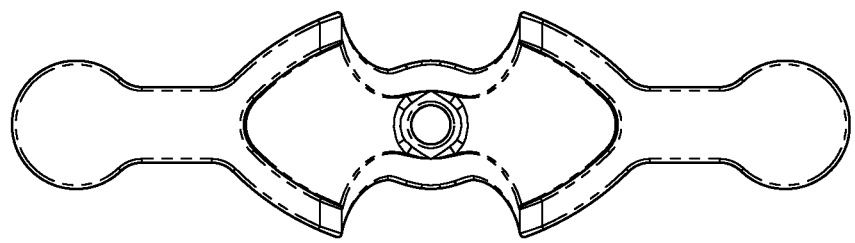
Fig. 41C
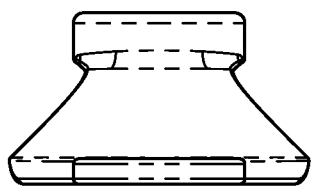
Fig. 41A

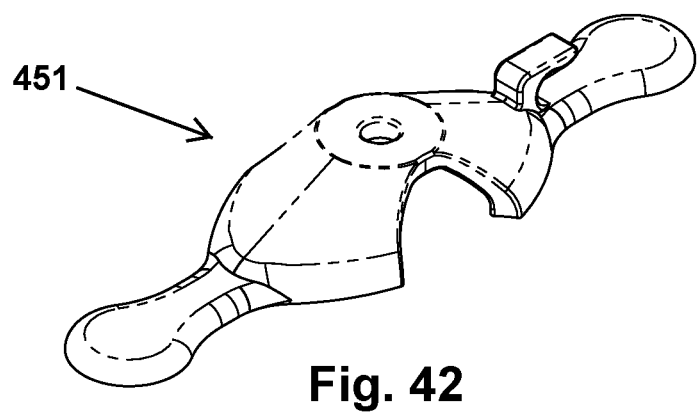
Fig. 42
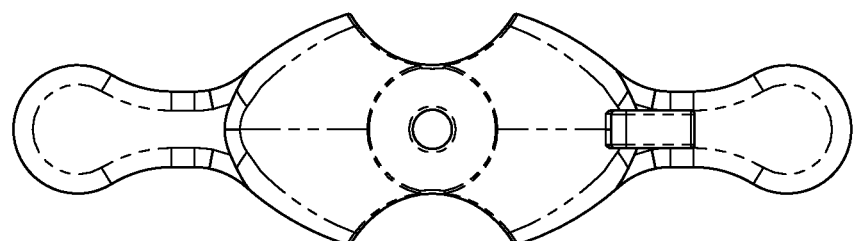
Fig. 43
Fig. 43B
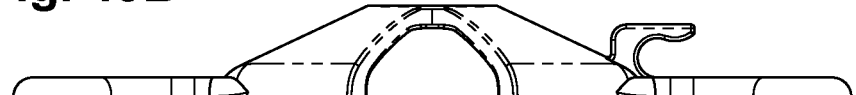
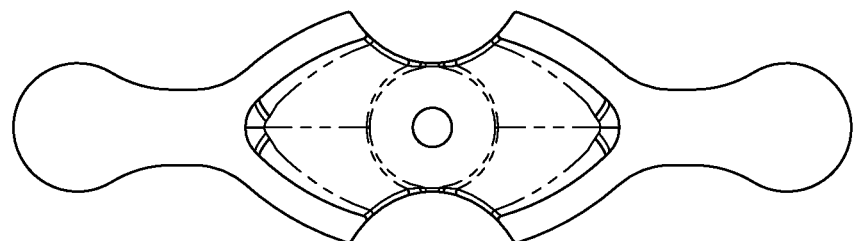
Fig. 43C
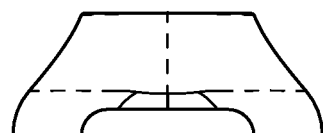
Fig. 43A

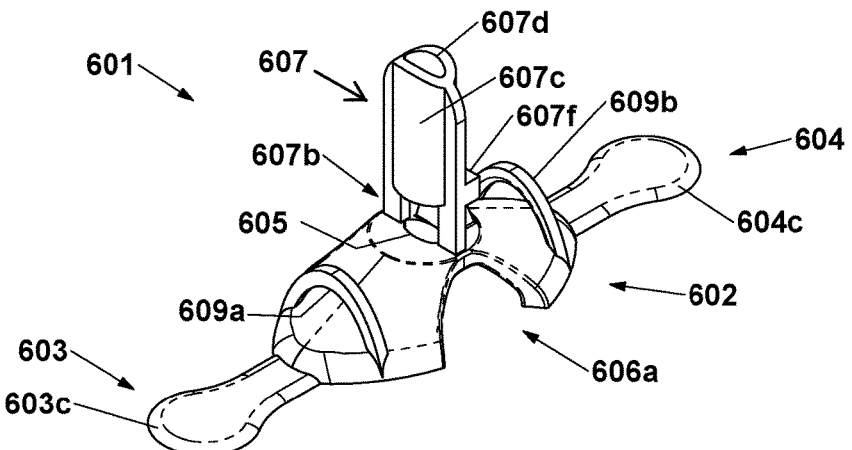
Fig. 47
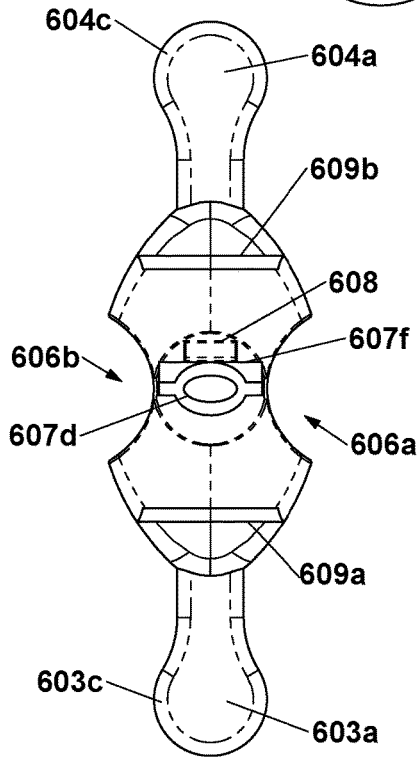 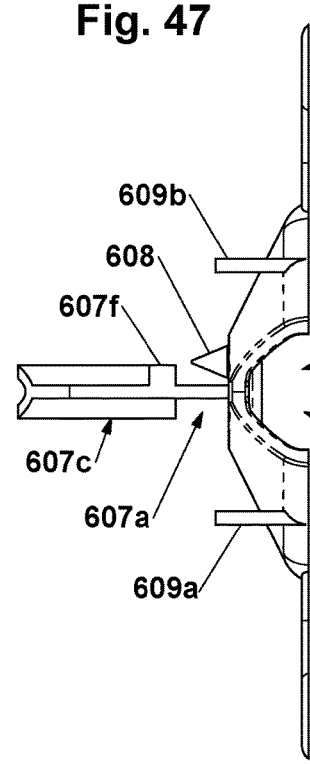 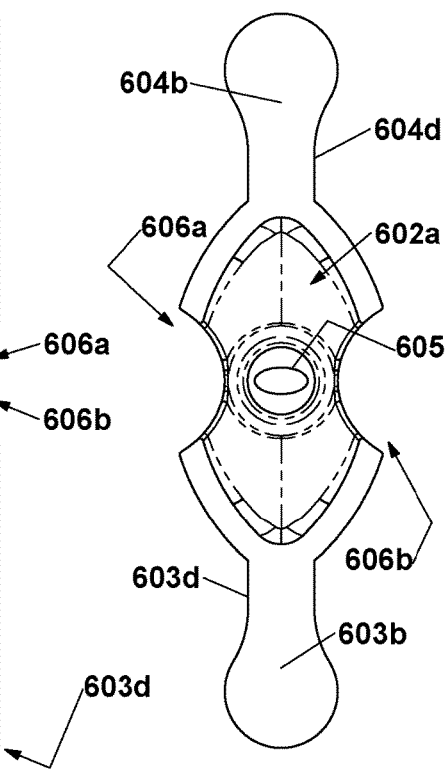
Fig. 48    Fig. 48B    Fig. 48C
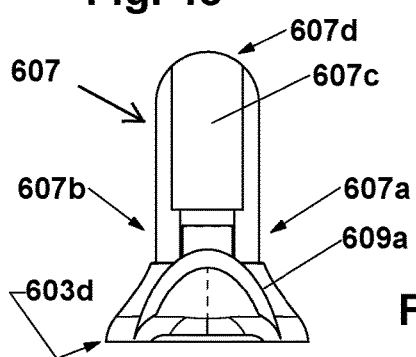
Fig. 48A

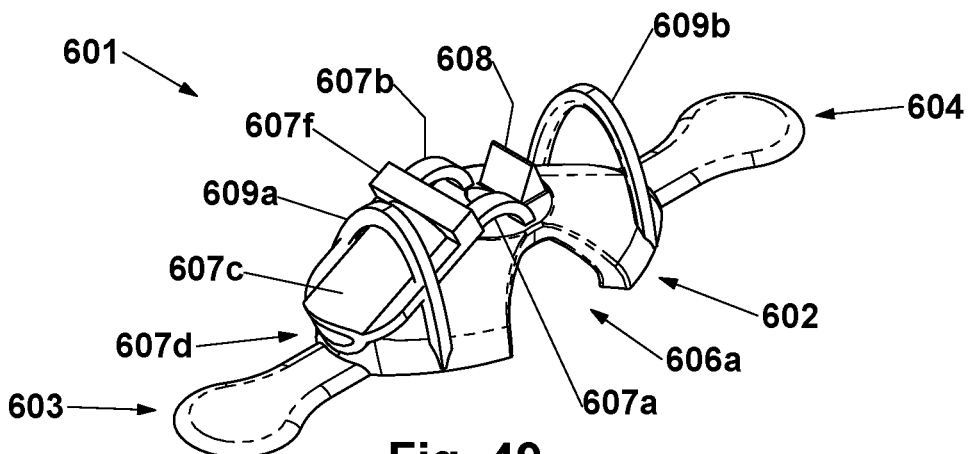
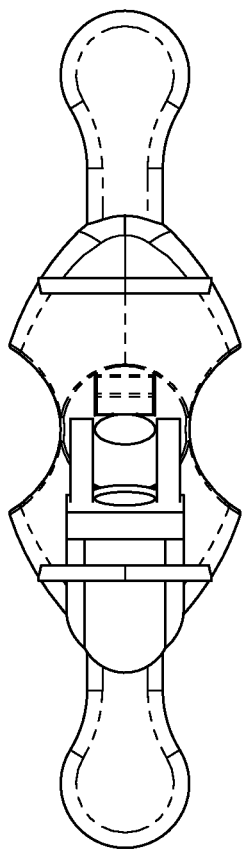
Fig. 50
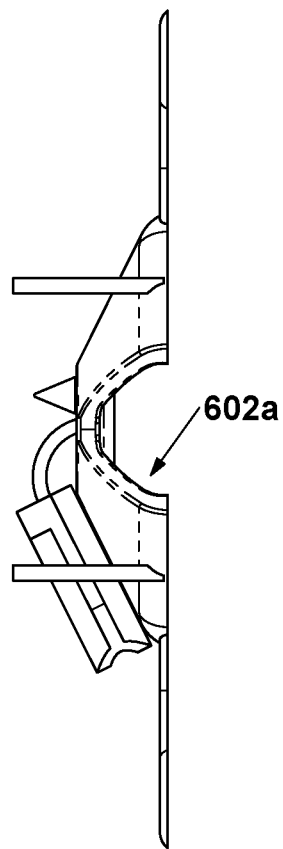
Fig. 50B
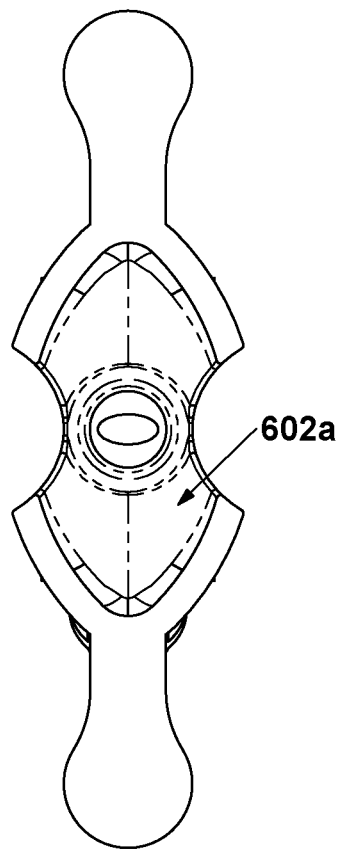
Fig. 50C
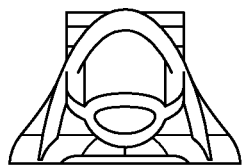
Fig. 50A

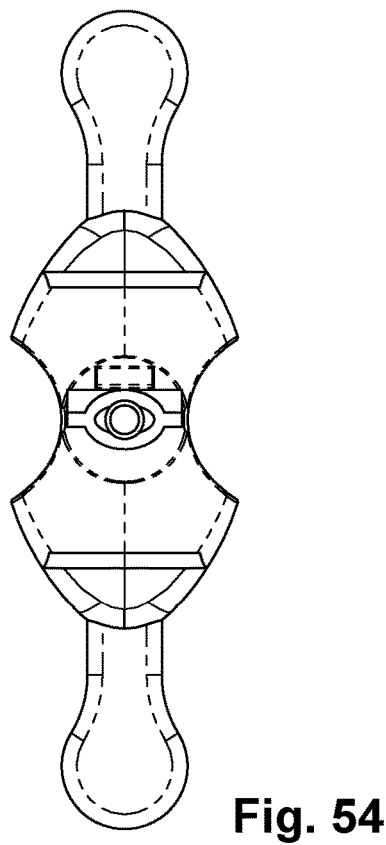
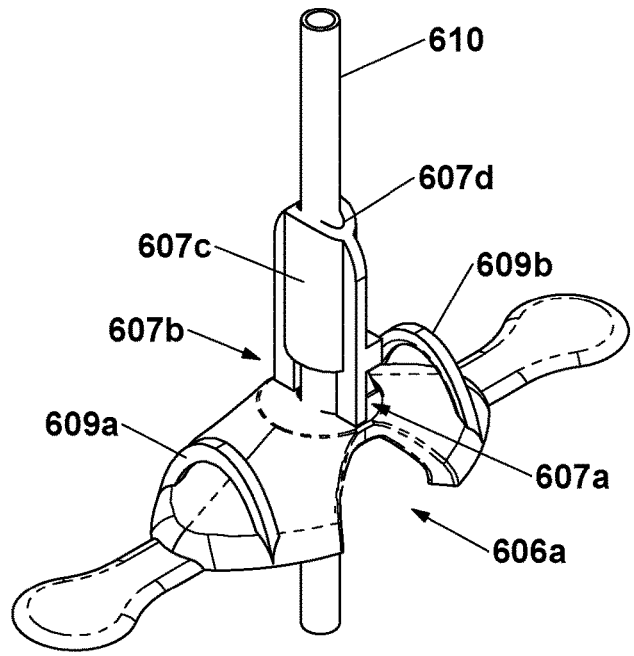
Fig. 53
Fig. 54
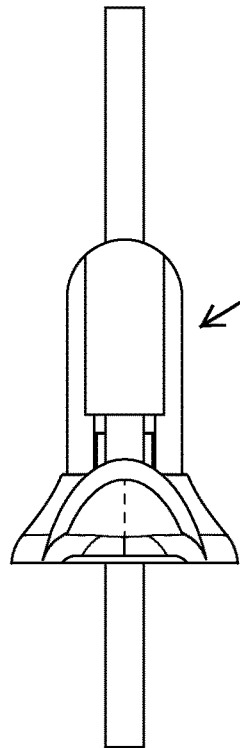
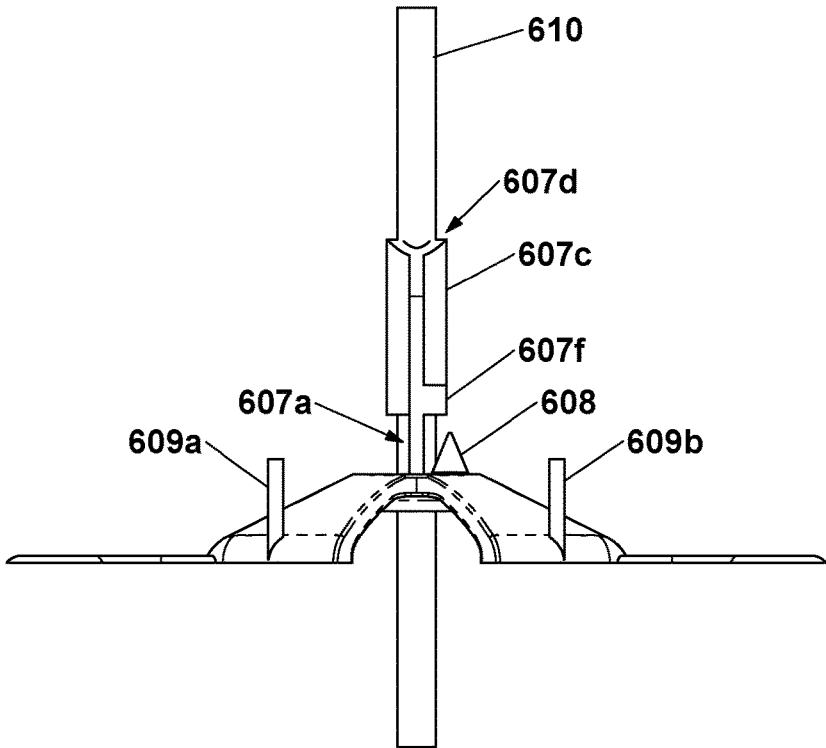
Fig. 54A
Fig. 54B

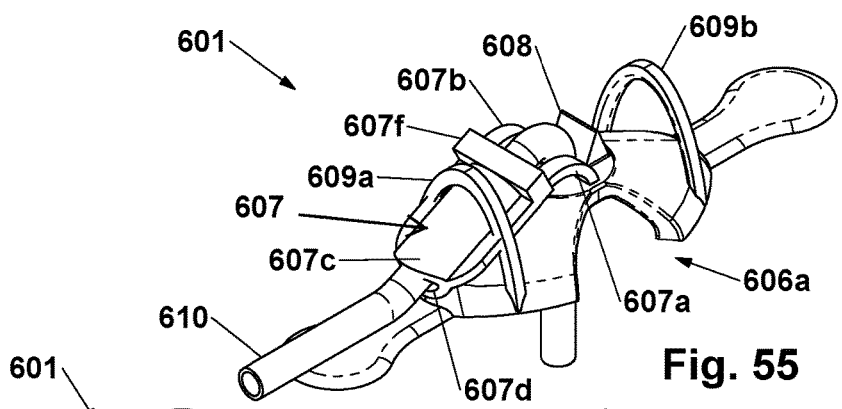
Fig. 55
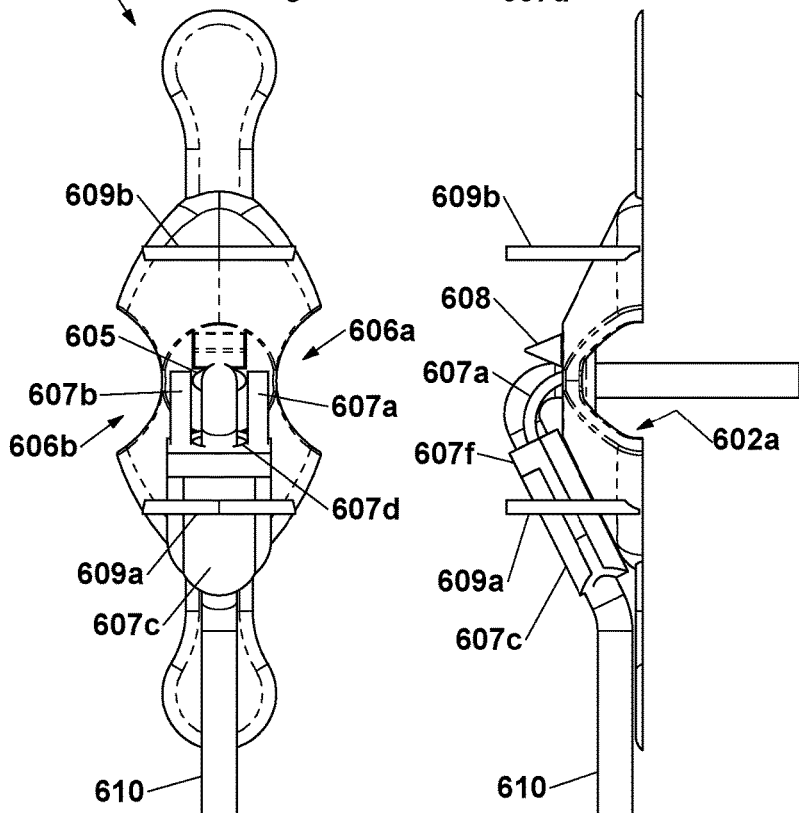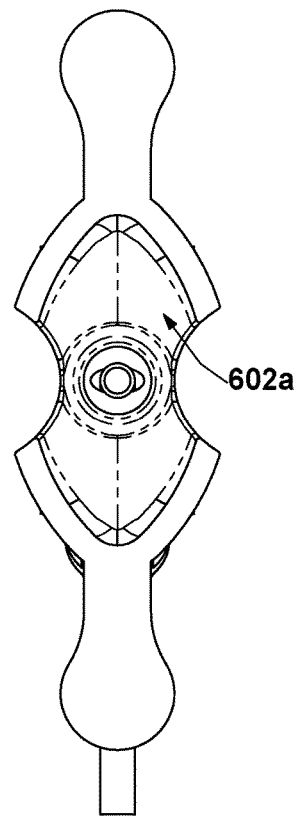
Fig. 56    Fig. 56B    Fig. 56C
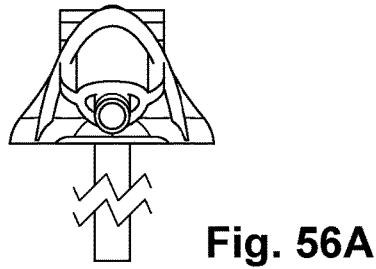
Fig. 56A

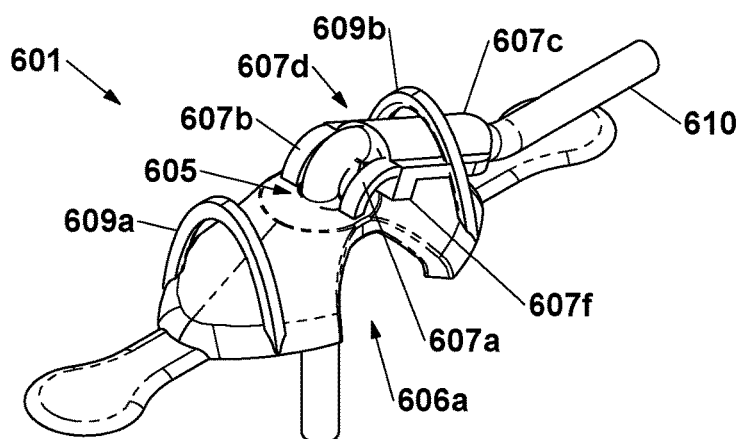
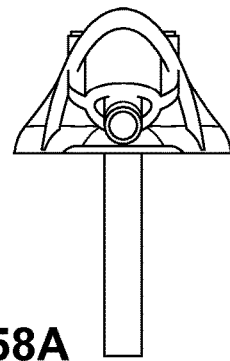
Fig. 57
Fig. 58A
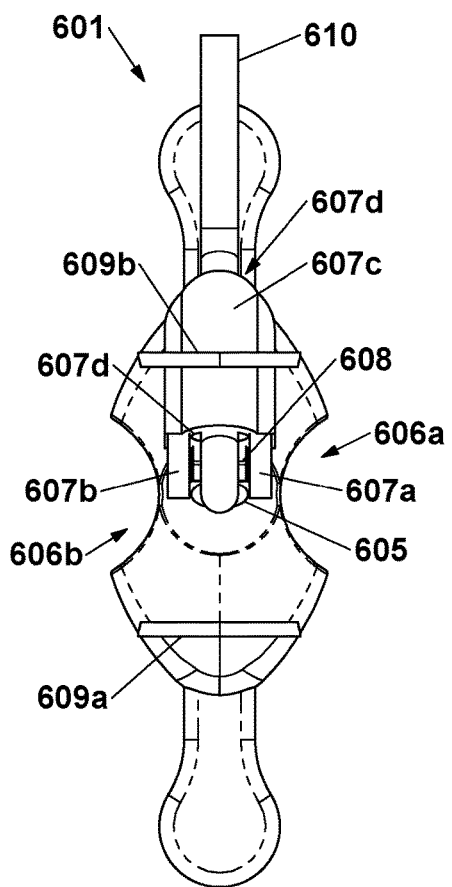
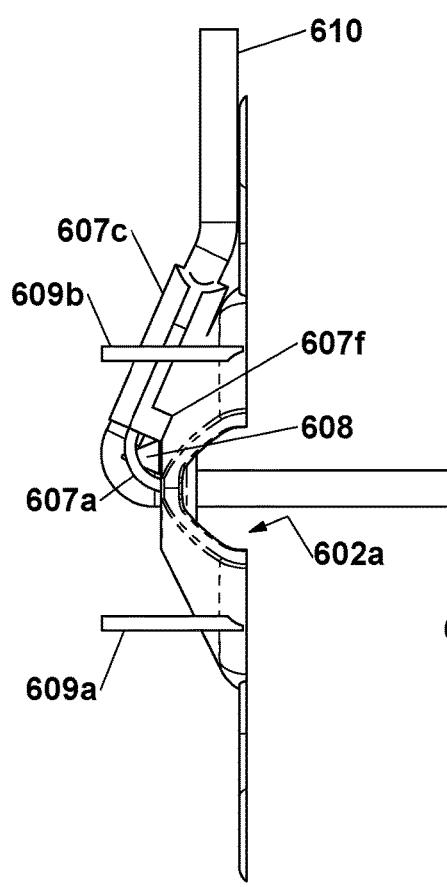
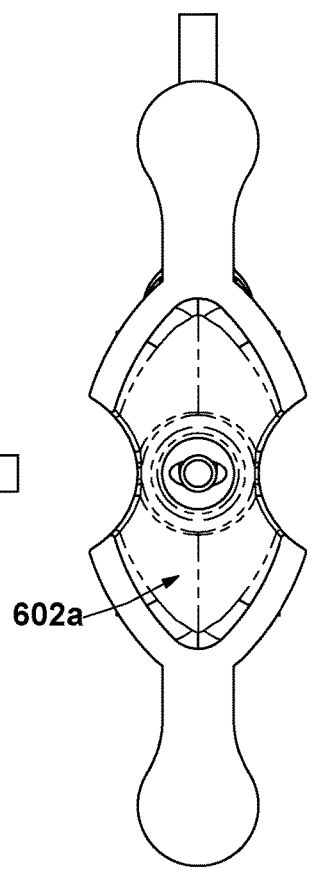
Fig. 58
Fig. 58B
Fig. 58C

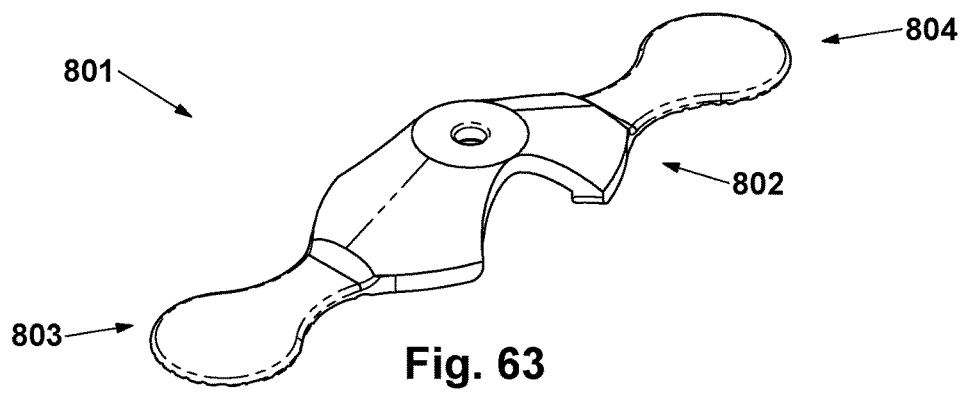
Fig. 63
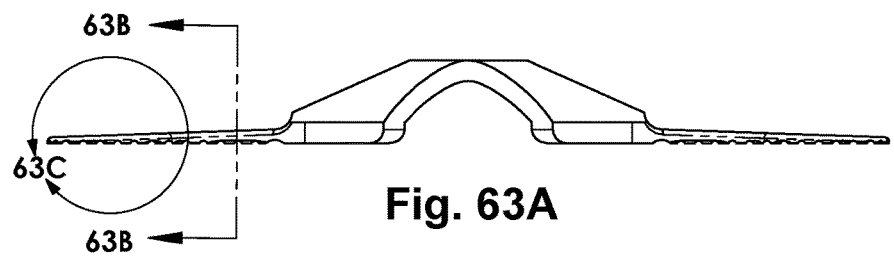
Fig. 63A
Fig. 63B
Fig. 63C
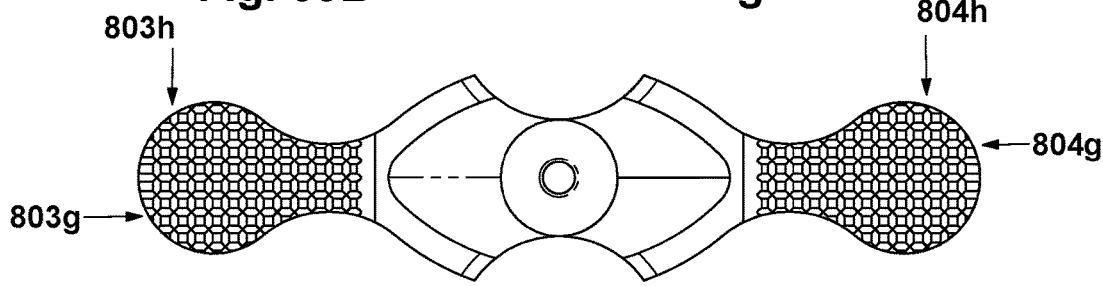
Fig. 63D
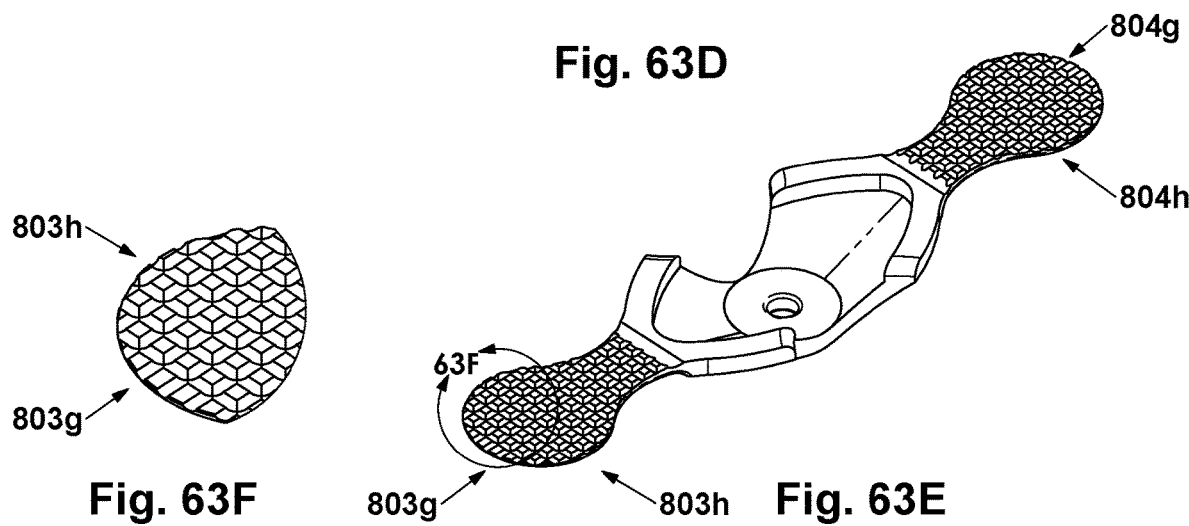
Fig. 63F
Fig. 63E

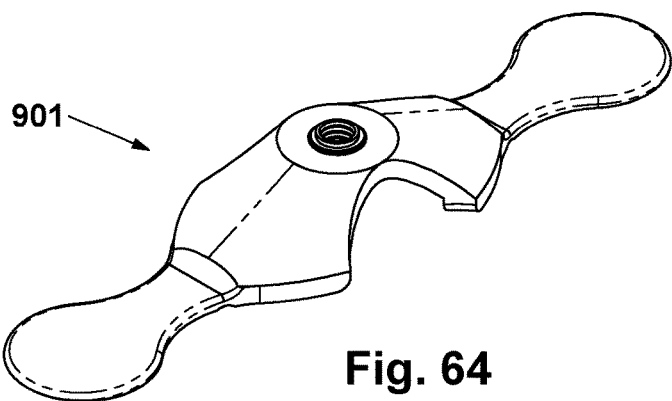
Fig. 64
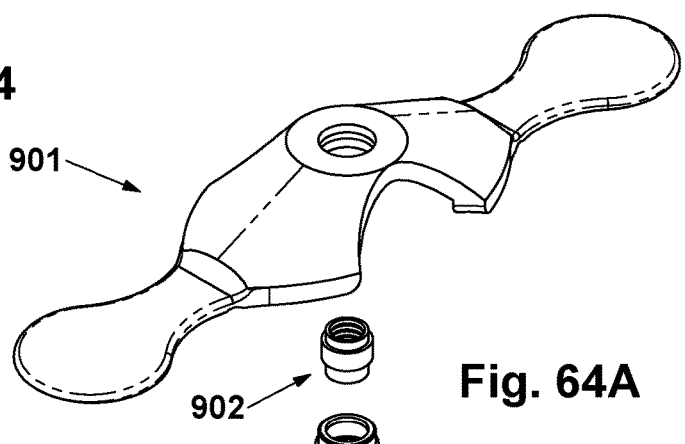
Fig. 64A
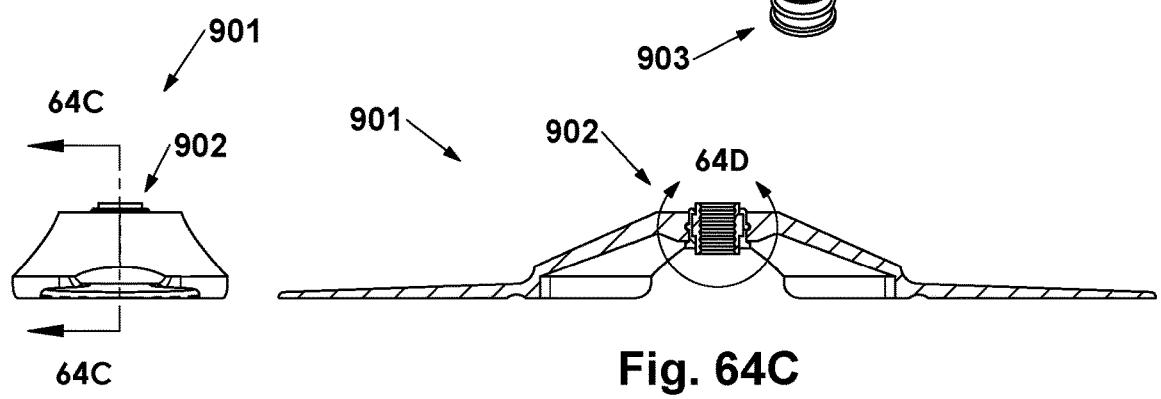
Fig. 64B
Fig. 64C
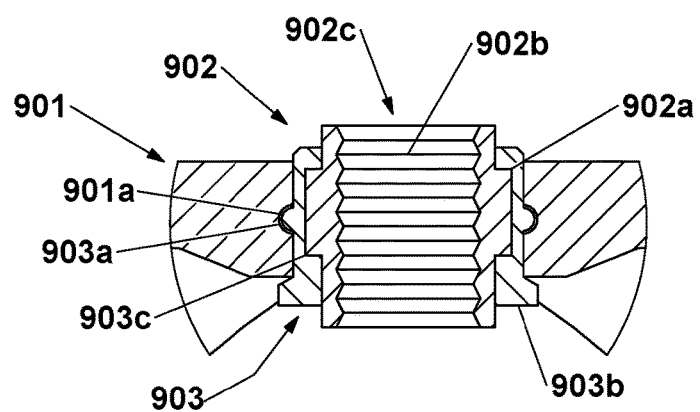
Fig. 64D

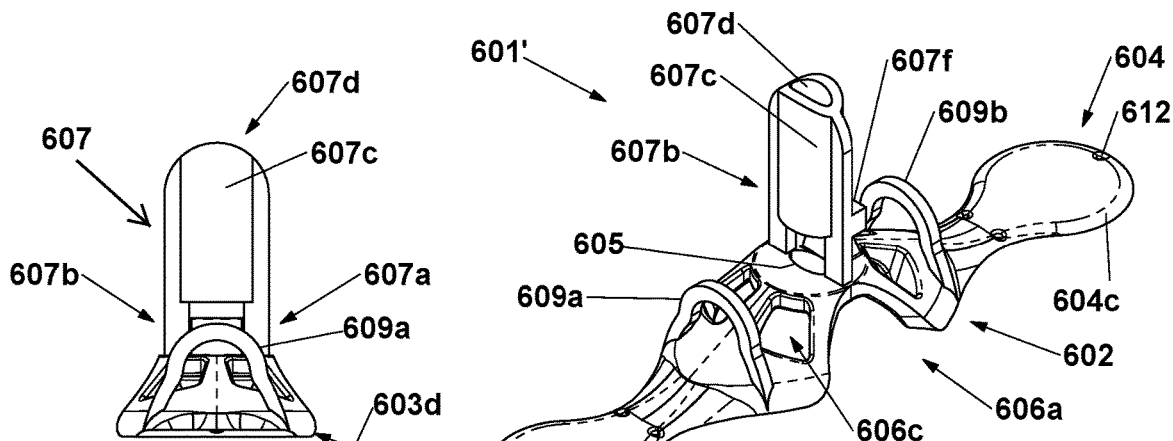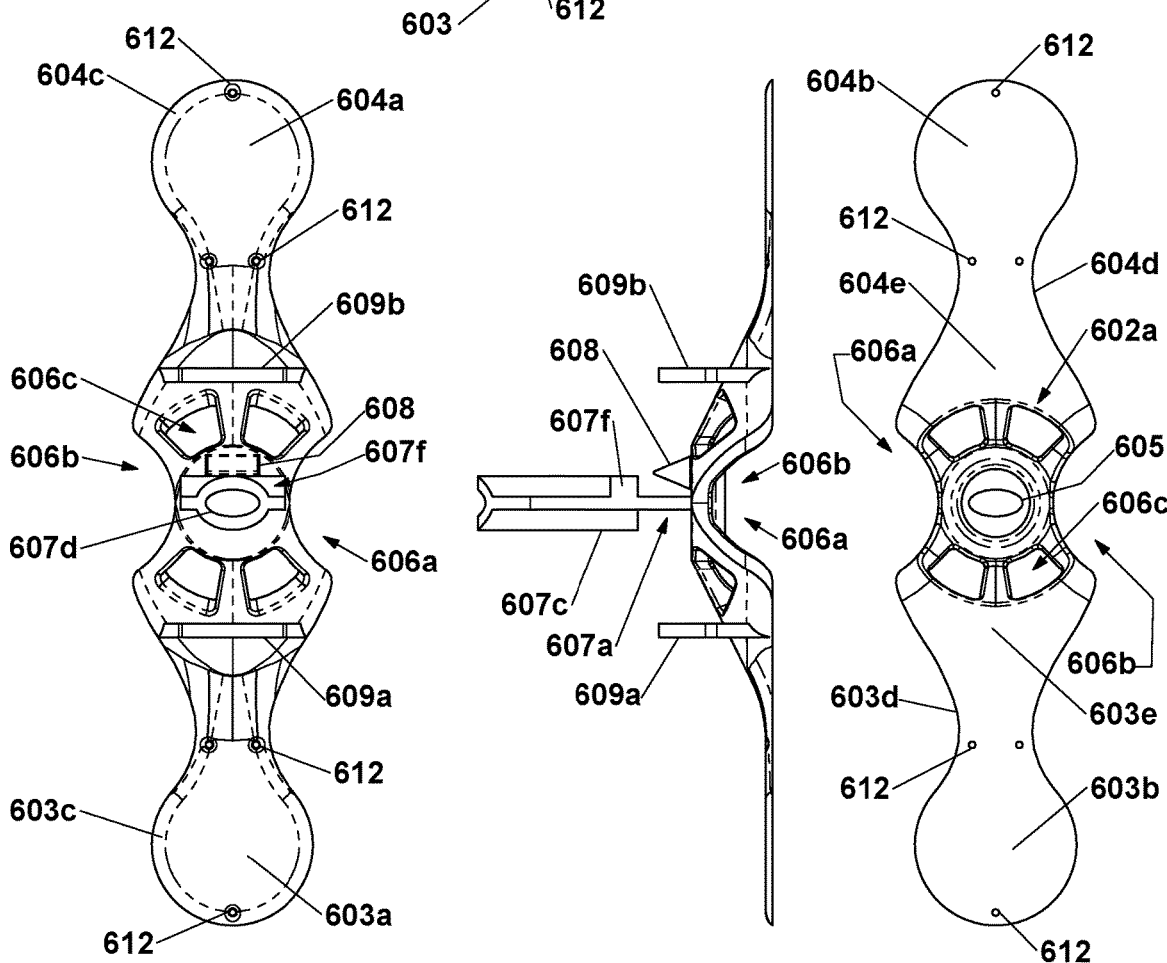

METHOD OF STABILIZING CATHETER TUBE USING STABILIZING DEVICE

CROSS REFERENCE TO RELATED APPLICATIONS

The present application is a continuation of U.S. patent application Ser. No. 16/148,202, filed Oct. 1, 2018, now U.S. Pat. No. 10,639,453, which is a continuation of U.S. patent application Ser. No. 15/680,704, filed Aug. 18, 2017, now U.S. Pat. No. 10,086,168, which claims the filing benefits of U.S. provisional applications, Ser. No. 62/501,988, filed May 5, 2017; Ser. No. 62/442,566, filed Jan. 5, 2017, and Ser. No. 62/377,098, filed Aug. 19, 2016, which are hereby incorporated herein by reference in their entireties.

FIELD OF THE INVENTION

The present invention relates generally to control and stabilization of catheters and other similar generally flexible tubes comprised of medical-grade plastic or other known polymer materials, the purpose of which is for facilitating medical procedures related to draining or allowing for the drainage of bodily fluids or substantially liquid and flowable materials from the interior to the exterior portions of the human body for patients undergoing on-going, periodic, or one-time use medical treatments and procedures.

BACKGROUND OF THE INVENTION

When a patient/doctor is going to be using a catheter or a similar device to drain fluids from the body, dislodgment of the catheter at the stoma site can significantly increase the risk of infection and irritation to the surrounding skin. Thus, various solutions have been proposed to retain a catheter in place at the patient. For example, for a bladder Mitrofanoff surgery, a Foley catheter leaves an inflated balloon-like device inside the bladder and can cause bladder spasms as it hits or comes in contact with the interior wall of the bladder. The Foley Catheter remains stationary within the bladder and cannot be removed until the balloon-like device is deflated. It works well to keep the stoma passageway open while it heals and allows the bladder to be drained. However, a major disadvantage to the patient is that the balloon-like device in the bladder can, and often does in a large majority of patients, cause major bladder spasms during the time that it remains in place. Bladder spasms because of the presence of the Foley Catheter and its inflated balloon-like device are well known to cause frequent, if not continuous levels of extreme discomfort and pain in most if not all patients who must undergo this on-going and preferably temporary medical procedure.

There are some types of other catheter stabilizers, but they are not placed over the stoma site which gives ample opportunity for the catheter to be accidentally or otherwise inadvertently pulled out of the bladder or stoma passageway. These types of devices tend to provide only a partial solution and fall short due to inherent limitations of their designs. Taping the catheter down directly to the surface of the skin is typically required, but this is not an adequate or long-term solution for patients needing to drain a bladder manually over an extended period of time, which is generally defined by the particular instance or length of the healing process of each particular patient. If the installed catheter is not closely monitored or otherwise carefully guarded, it may easily and inadvertently become mechanically pulled-on or get caught on something. In severe cases, it will rip out causing extreme pain, possible infection, irritation of the skin, and a possible revision or emergency repair surgery. The known L-stint procedure offers some degree of remedy to the problem of stomal stenosis, but the bladder is not able to be drained without the use of a second additional catheter. Every time the patient needs to be catheterized, a brand-new catheter needs to be used to perform the catheterization and another second additional catheter is used to create a new L-stint.

SUMMARY OF THE INVENTION

The present invention provides an external catheter stabilizer device that is positionable at and around a stoma and that holds and retains a generally flexible tube that passes through the patient, such as for a catheter or the like. The device includes a base portion that has one or more engaging surfaces for attaching or affixing the device at the patient, and the device includes a central passageway that may snugly receive the generally flexible catheter tube therethrough. The device further includes a hook or catheter restraint feature that allows for the tube to be bent or routed through the central passageway and through the hook or catheter restraint feature (disposed radially outward from the central passageway) so that the catheter tube can be mechanically held in place at the device. The center region of the device (where the passageway is established) may be separated from the base portion by a plurality of arms, spokes, or structural support features such that the stoma that is surrounded by the base portion is viewable (such as for post-operation observation by the medical personnel) and can have air flow thereat. The center region may be raised above the base portion so as to be spaced from the patient when the device is attached at the patient. The device may retain the tube and may provide a means for pinching or clamping or bending the tube to selectively restrict flow through the tube.

Thus, the present invention provides an external catheter stabilizer device that is attachable at a patient around a stoma and that allows for observation of the stoma while also retaining the generally flexible catheter tube at a desired position. The external catheter stabilizer device thus provides enhanced retention of a catheter tube that allows for repeated and ongoing use of the installed catheter tube and further provides for easier on-going and repeated periodic treatment of the patient, without requiring a significant quantity of new catheter tubes to be discarded after each use, and without requiring additional catheter tubes used in one procedural instance, balloon-like devices or the like.

These and other objects, advantages, purposes and features of the present invention will become apparent upon review of the following specification in conjunction with the drawings.

BRIEF DESCRIPTION OF THE DRAWINGS

FIG. 6 is a perspective view of the device of FIGS. 1 through 2D, showing further details of the retaining clip member and arrangement of the generally flexible catheter tube when temporarily secured into place;

FIG. 6A is a side elevation of the arrangement shown in FIG. 6;

FIG. 6B is another side elevation of the arrangement shown in FIG. 6;

FIG. 11 is a perspective view showing an example arrangement of the device shown in FIGS. 9 through 10B, shown with an example of a catheter tube engaged and temporarily clipped into place;

FIG. 11A is a side elevation of the example arrangement shown in FIG. 11;

FIG. 11B is another side elevation of the example arrangement shown in FIG. 11;

FIG. 22 is a perspective view of another device of the present invention similar to the device shown in FIGS. 20-21C, where the design comprises three radial extensions rather than a single elongated member;

FIG. 23 is a top plan view of the device shown in FIG. 22;

FIG. 23A is a side elevation of the device shown in FIG. 22;

FIG. 23B is another side elevation of the device shown in FIG. 22;

FIG. 24 is a perspective view of another device of the present invention, where a generally elongated member includes a raised center portion that is supported by a generally elliptical structure including elongated portions providing contact surface area for use of medical adhesives or tape for stability and attachment to the surface of the skin;

FIG. 25 is a top plan view of the device shown in FIG. 24;

FIG. 25A is an end elevation of the device shown in FIG. 24;

FIG. 25B is a side elevation of the device shown in FIG. 24;

FIG. 25C is a bottom plan view of the device shown in FIG. 24;

FIG. 36 is a perspective view of another device similar to the device shown in FIG. 26, where the two longitudinal openings at the sloped center portion have been eliminated and the side openings have been enlarged and include the addition of radii at the bottom portion near the center portion of the base, and the center hole has been optionally simplified;

FIG. 37 is a top plan view of the device shown in FIG. 36;

FIG. 37A is an end elevation of the device shown in FIG. 36;

FIG. 37B is a side elevation of the device shown in FIG. 36;

FIG. 37C is a bottom plan view of the device shown in FIG. 36;

FIG. 38 is a perspective view of another device similar to the device shown in FIG. 36, where the size or scale of the device has been generally reduced by a factor of 0.80 of that shown in FIG. 36;

FIG. 39 is a top plan view of the device shown in FIG. 38;

FIG. 39A is an end elevation of the device shown in FIG. 38;

FIG. 39B is a side elevation of the device shown in FIG. 38;

FIG. 39C is a bottom plan view of the device shown in FIG. 38;

FIG. 40 is a perspective view of another device similar to the device shown in FIG. 38, where the thickness and therefore the strength of the central portion has been enlarged and the distal ends have been revised to include more circular-shaped ends;

FIG. 41 is a top plan view of the device shown in FIG. 40;

FIG. 41A is an end elevation of the device shown in FIG. 40;

FIG. 41B is a side elevation of the device shown in FIG. 40;

FIG. 41C is a bottom plan view of the device shown in FIG. 40;

FIG. 42 is a perspective view of another device similar to the device shown in FIG. 40, where the overall height has been reduced and the top outer profile shape of the device has been streamlined;

FIG. 43 is a top plan view of the device shown in FIG. 42;

FIG. 43A is an end elevation of the device shown in FIG. 42;

FIG. 43B is a side elevation of the device shown in FIG. 42;

FIG. 43C is a bottom plan view of the device shown in FIG. 42;

FIG. 47 is a perspective view of another embodiment of the present invention, shown with a flexible tube retainer that flexes to selectively retain the tube in either a free-flow orientation or a restricted or no-flow orientation;

FIG. 48 is a top plan view of the device shown in FIG. 47;

FIG. 48A is an end elevation of the device shown in FIG. 47;

FIG. 48B is a side elevation of the device shown in FIG. 47;

FIG. 48C is bottom plan view of the device shown in FIG. 47;

FIG. 49 is a perspective view of the device shown in FIG. 48, shown configured for free-flow operation without a catheter installed for purpose of clarity;

FIG. 50 is a top plan view of the device shown in FIG. 49;

FIG. 50A is an end elevation of the device shown in FIG. 49;

FIG. 50B is a side elevation of the device shown in FIG. 49;

FIG. 50C is a bottom plan view of the device shown in FIG. 49;

FIG. 51 is a perspective view of the device shown in FIG. 48, shown configured for no-flow operation without a catheter installed for the purpose of clarity;

FIG. 52 is a top plan view of the device shown in FIG. 51;

FIG. 52A is an end elevation of the device shown in FIG. 51;

FIG. 52B is a side elevation of the device shown in FIG. 51;

FIG. 52C is a bottom plan view of the device shown in FIG. 51;

FIG. 53 is a perspective view of the device shown in FIG. 47, shown with an example section of flexible catheter tube installed within the device at a generally vertical position allowing for free-flow of fluid through the catheter;

FIG. 54 is a top plan view of the device shown in FIG. 53;

FIG. 54A is an end elevation of the device shown in FIG. 53;

FIG. 54B is a side elevation of the device shown in FIG. 53;

FIG. 55 is a perspective view of the device shown in FIG. 53, shown configured for free-flow of fluid operation with an example flexible catheter tube installed;

FIG. 56 is a top plan view of the device and an example catheter installed.as shown in FIG. 55;

Figure 59:
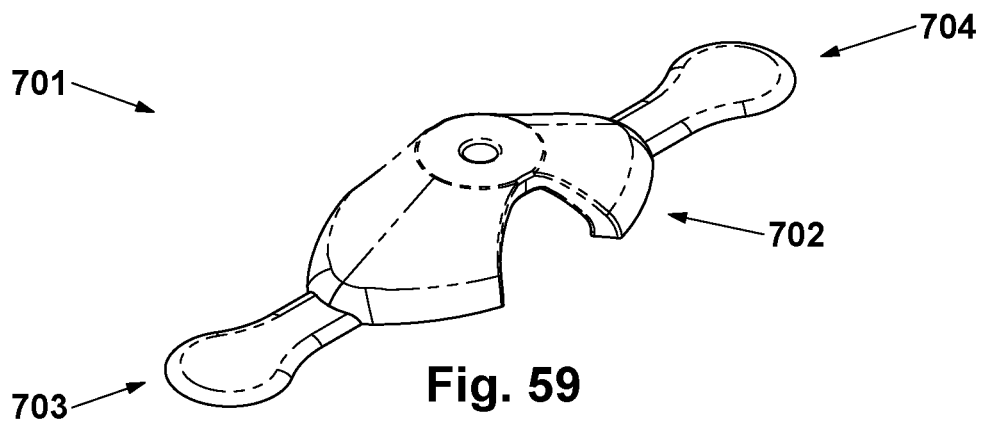
Figure 59A:
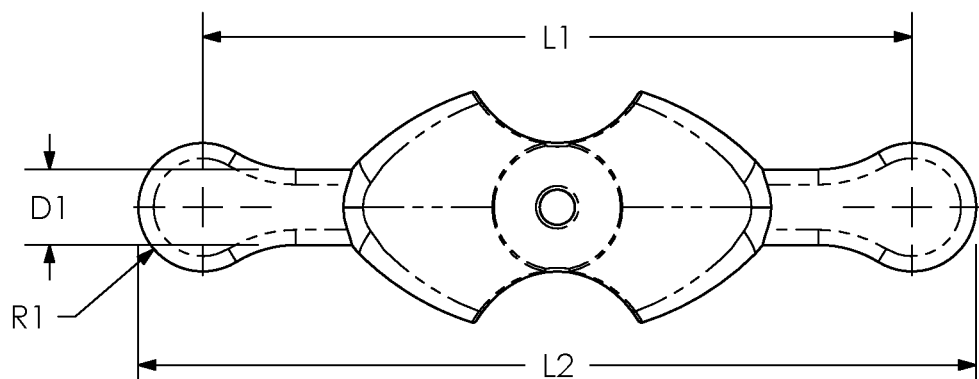
Figure 59B:
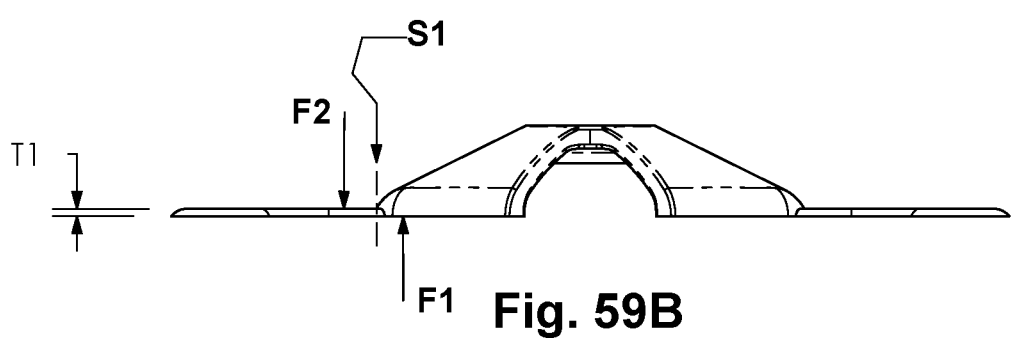
Figure 59C:
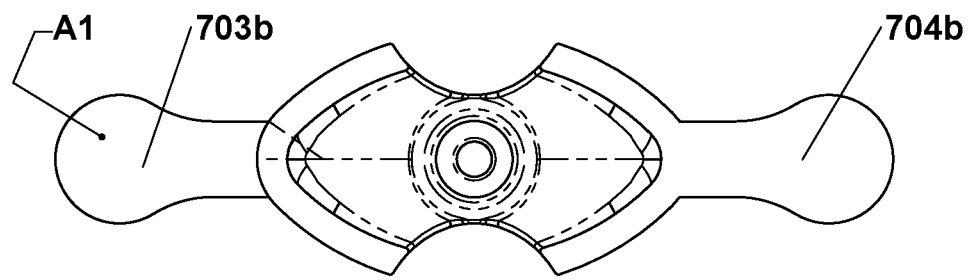
Figure 60:
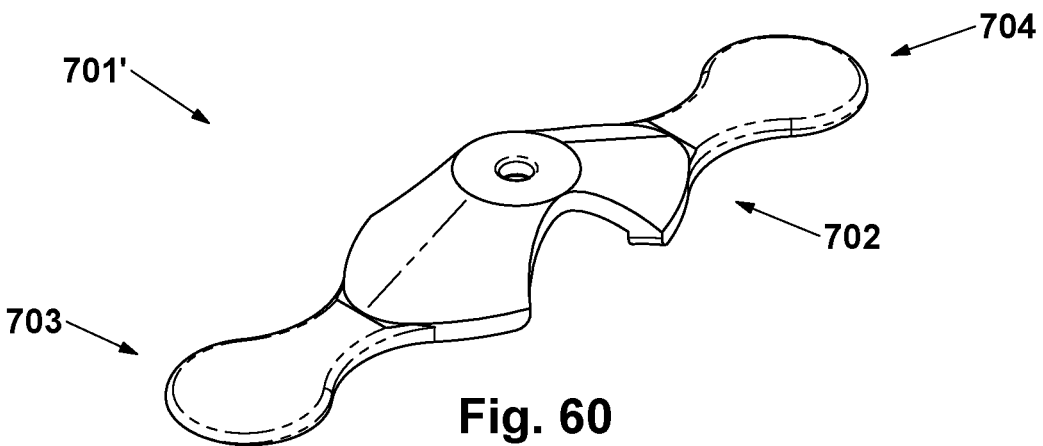
Figure 60A:
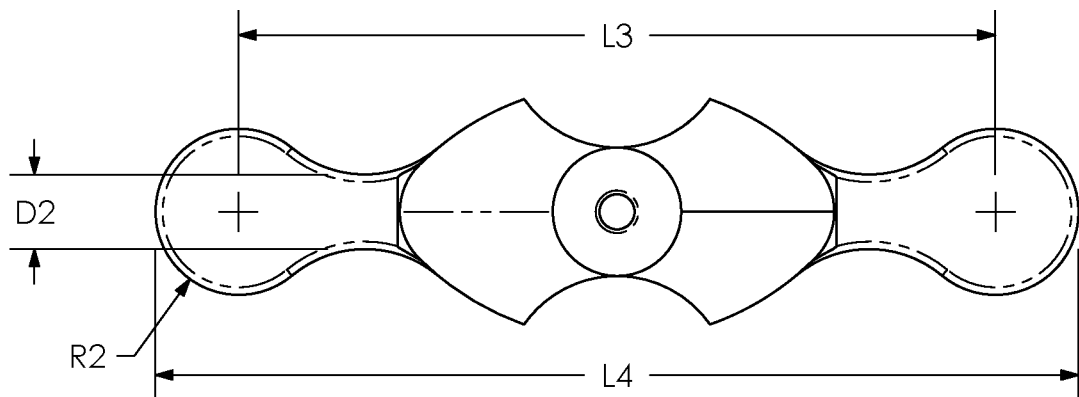
Figure 60B:
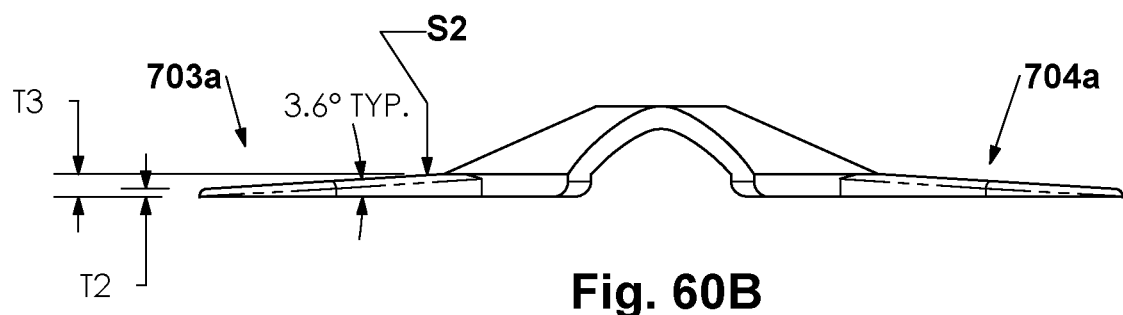
Figure 60C:
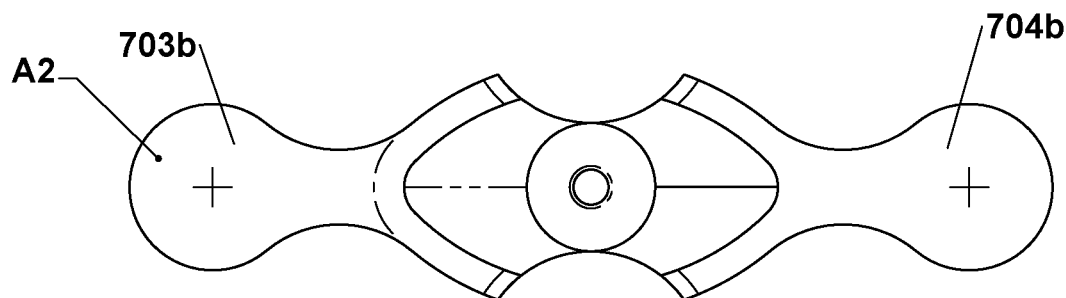
Figure 61:
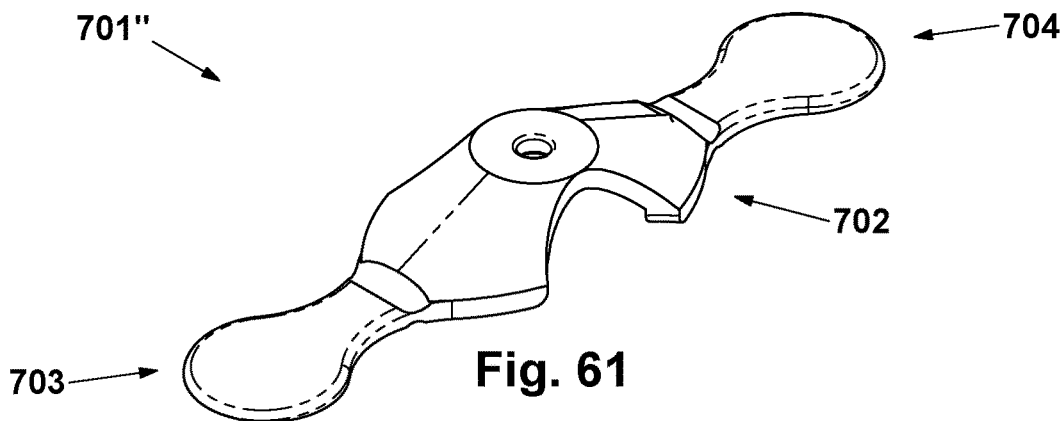
Figure 61A:
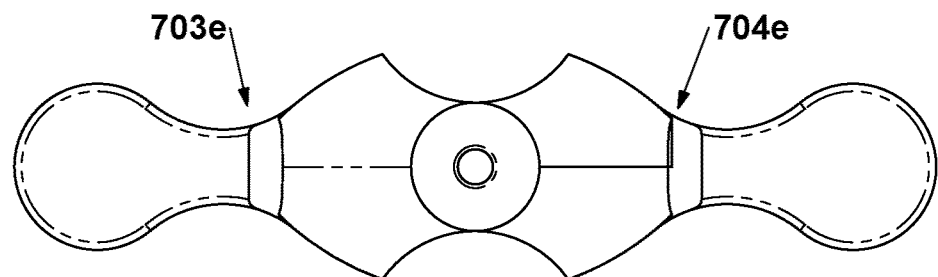
Figure 61B:
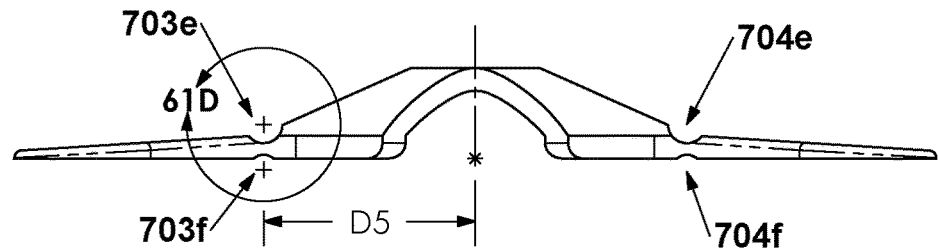
Figure 61D:
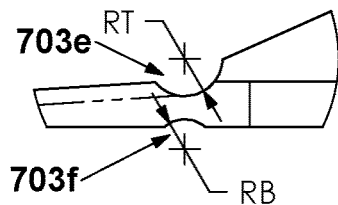
Figure 61C:
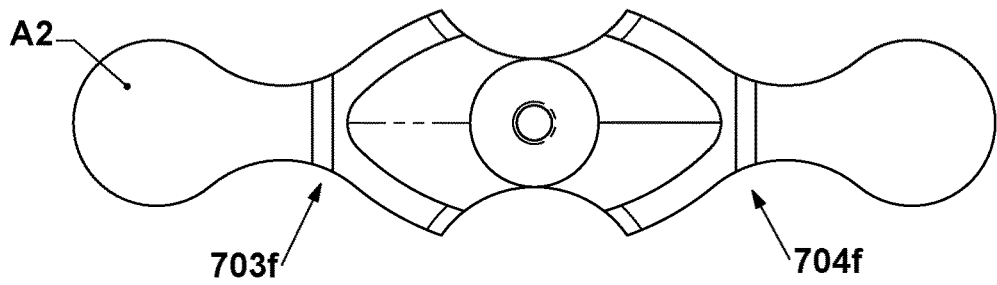
Figure 62:
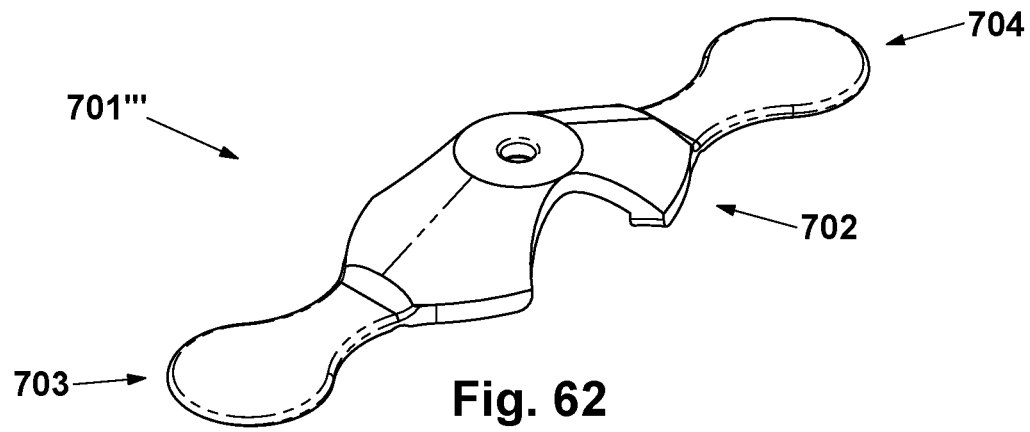
Figure 62A:
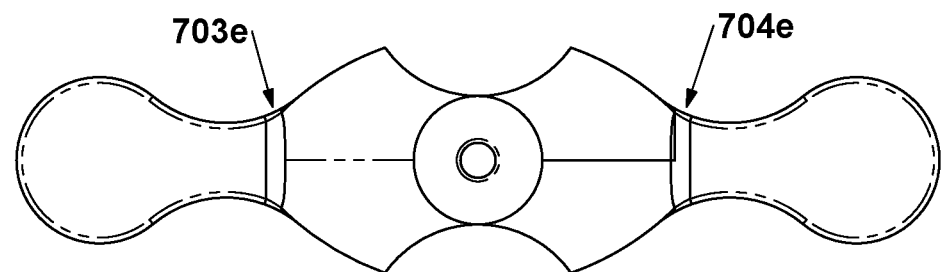
Figure 62B:
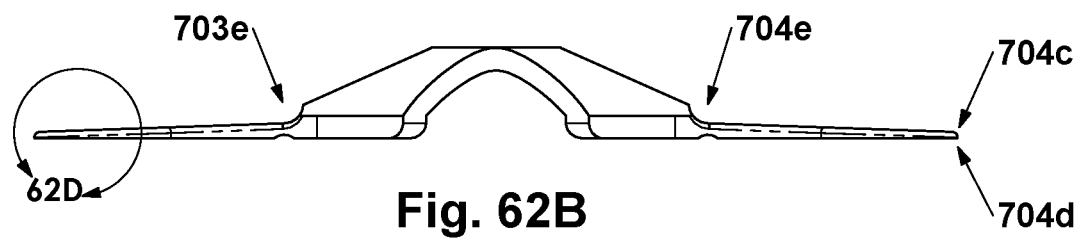
Figure 62D:
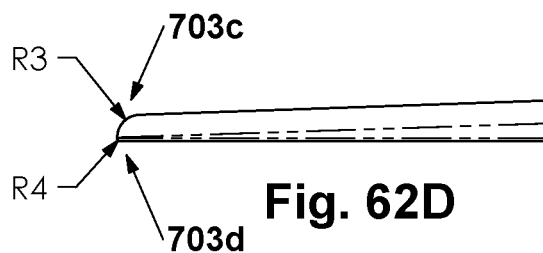
Figure 62C:
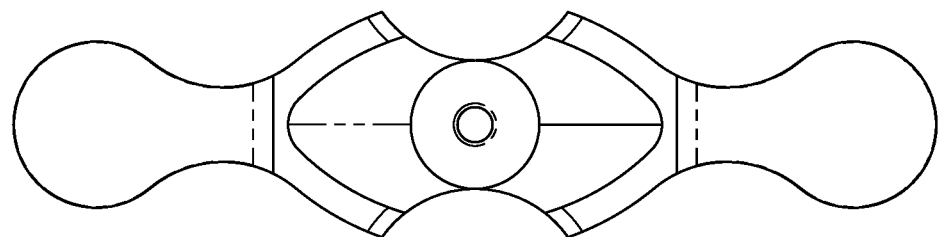
Figure 65:
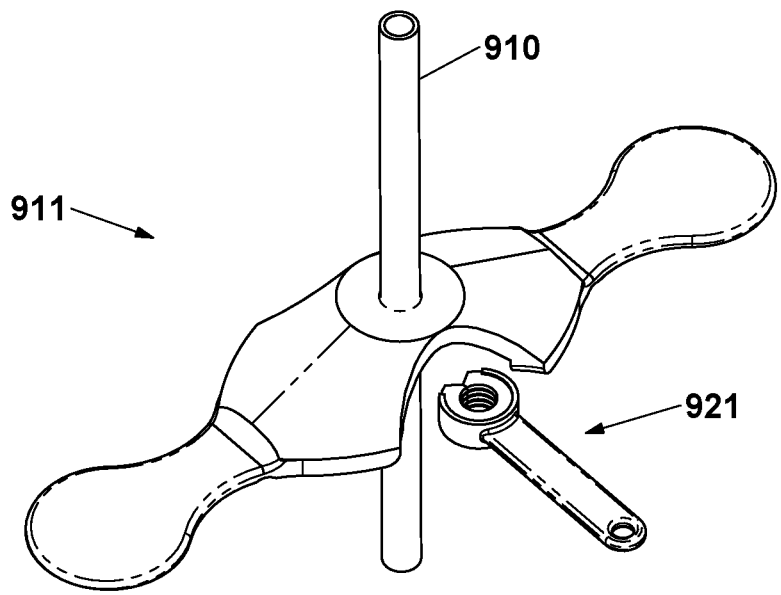
Figure 65A:
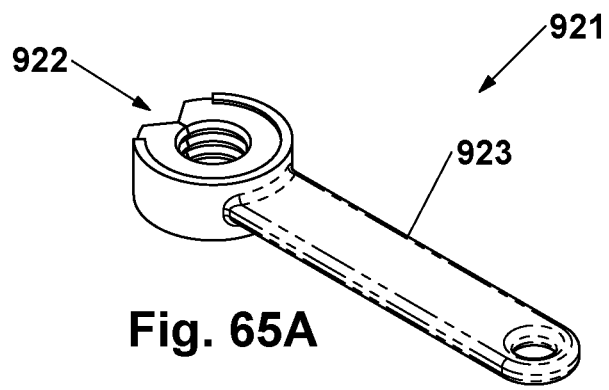
Figure 65B:
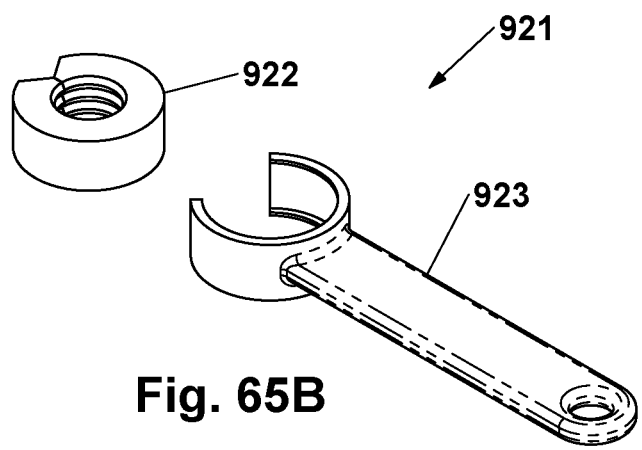

FIG. 56A is an end elevation of the device and an example catheter installed as shown in FIG. 55;

FIG. 56B is a side elevation of the device and an example catheter installed as shown in FIG. 55;

FIG. 56C is bottom plan view of the device and an example catheter installed as shown in FIG. 55;

FIG. 57 is a perspective view of the device shown in FIG. 53 configured for blocked or no-flow of fluid operation with an example flexible catheter tube installed;

FIG. 58 is a top plan view of the device and an example catheter installed as shown in FIG. 57;

FIG. 58A is an end elevation of the device and an example catheter installed as shown in FIG. 57;

FIG. 58B is a side elevation of the device and an example catheter installed as shown in FIG. 57;

FIG. 58C is a bottom plan view of the device and an example catheter installed as shown in FIG. 57;

FIG. 59 is a perspective view of another device of the present invention having a longitudinal paddles design;

FIG. 59A is a top plan view of the longitudinal paddles design of FIG. 59;

FIG. 59B is a side elevation of the longitudinal paddles design of FIG. 59;

FIG. 59C is a bottom plan view of the longitudinal paddles design of FIG. 59;

FIG. 60 is a perspective view of another device of the present invention having a longitudinal paddles design;

FIG. 60A is a top plan view of the basic longitudinal paddles design of FIG. 60;

FIG. 60B is a side elevation of the basic longitudinal paddles design of FIG. 60;

FIG. 60C is a bottom plan view of the basic longitudinal paddles design of FIG. 60;

FIG. 61 is a perspective view of another device of the present invention having a longitudinal paddles design;

FIG. 61A is a top plan view of the basic longitudinal paddles design of FIG. 61;

FIG. 61B is a side elevation of the longitudinal paddles design of FIG. 61;

FIG. 61C is a bottom plan view of the longitudinal paddles design of FIG. 61;

FIG. 61D is a detail view of the area 61D in FIG. 61B;

FIG. 62 is a perspective view of another device of the present invention having a longitudinal paddles design;

FIG. 62A is a top plan view of the longitudinal paddles design of FIG. 62;

FIG. 62B is a side elevation of the longitudinal paddles design of FIG. 62;

FIG. 62C is a bottom plan view of the longitudinal paddles design of FIG. 62;

FIG. 62D is a detail view of the area 62D in FIG. 62B;

FIG. 63 is a perspective view of another device of the present invention having a longitudinal paddles design;

FIG. 63A is a side elevation of the longitudinal paddles design of FIG. 63;

FIG. 63B is a sectional view taken along the line 63B-63B in FIG. 63A;

FIG. 63C is a detail view of the area 63C in FIG. 63A;

FIG. 63D is a bottom plan view of the longitudinal paddles design of FIG. 63;

FIG. 63E is a bottom perspective view of the longitudinal paddles design of FIG. 63;

FIG. 63F is a detail view of the area 63F in FIG. 63E;

FIG. 64 is a perspective view of another device of the present invention, shown with an example of a catheter disinfectant wiper arrangement;

FIG. 64A is an exploded assembly view of the device of FIG. 64;

FIG. 64B is an end elevation of the embodiment shown in FIG. 64;

FIG. 64C is a cross-section view of the embodiment taken along the line 64C-64C in FIG. 64B;

FIG. 64D is a detail view of the area 64D in FIG. 64C;

FIG. 65 is a perspective view of another device of the present invention, shown with an example catheter disinfectant wiper tool;

FIG. 65A is a close-up perspective view of the example catheter disinfectant wiper tool;

FIG. 65B is an exploded perspective view of the replaceable disinfectant wiper insert and tool handle;

FIG. 66 is a perspective view of another embodiment of the present invention representing further advancements in the design and functions continuing from those embodiments shown in FIG. 47;

FIG. 67 is a top plan view of the device shown in FIG. 66;

FIG. 67A is an end elevation of the device shown in FIG. 66;

FIG. 67B is a side elevation of the device shown in FIG. 66; and

FIG. 67C is bottom plan view of the device shown in FIG. 66.

DESCRIPTION OF THE PREFERRED EMBODIMENTS

Referring now to the drawings and the illustrative embodiments depicted therein, an external catheter stabilizer (ECS) device provides support and retention of a catheter tube at a patient. There is a center hole or hub, of variable size, centered over the surgical stoma, where the catheter or other drainage tube is to be inserted. There is a hook or tube retainer located at an outer ring of the device, opposite of the part that contacts the patient, where the catheter or other drainage tube is hooked under, to allow the tube to be both secured to the device and to hold the tube in a stable position, thus preventing the tube from sliding in or out of the hole in the center or hub of the device. The size of the external catheter stabilizer, most specifically the center hole and the hook, are variable and are specific to the size of catheter used. Standard catheters can range in diameter from 3Fr (1 mm diameter) to 34Fr (11.3 mm diameter), so an ECS12 would correspond to an ECS device that is designed specifically for a 12Fr catheter. The embodiments shown in the drawings and described below illustrate various optional aspects of external catheter stabilizer devices in accordance with the present invention. Various aspects of the shown and/or described embodiments may be applicable to some or all of the other shown and/or described embodiments while remaining within the spirit and scope of the present invention.

An embodiment of the external catheter stabilizer (ECS) device (see FIGS. 1-8D) resembles a wagon wheel, but the size and shape can vary depending on the location of the device on the patient, the size of the patient, and the specific catheter or drainage tube used in conjunction with this device. The wagon-wheel design of the ECS allows for the device to be securely positioned on the patient, the catheter to be stabilized and secure through the ECS, and yet allow air flow and post-surgical observation of the surgical stoma and surrounding tissue.

The external catheter stabilizer device may comprise any suitable material. For example, the device may be made or manufactured from various types of medical grade plastics, silicone, TPE or other medical grade materials or substances, which allows for the stability and flexibility needed or desired for proper or optimal functionality and performance of the device.

Methods of securing the device to the skin in any particular instance may be selected by the medical professional based upon the needs of the patient and tolerance to skin irritation and complications related to possible infection. For example, the underside (bottom) of the outer ring of the ECS may be fashioned with a circular array of Velcro hooks, which are attached to the ECS with a medical grade adhesive. The corresponding Velcro loops piece is adhered to the patient, encircling the surgical stoma, using medical grade adhesive. The decision of what type of adhesive, or if any other barrier or band between the ECS and the patient in any particular instance, may also be selected by medical professionals based upon the needs of the patient and the medical professional's opinion on what is needed for the best possible outcome for the patient.

Figure 1:
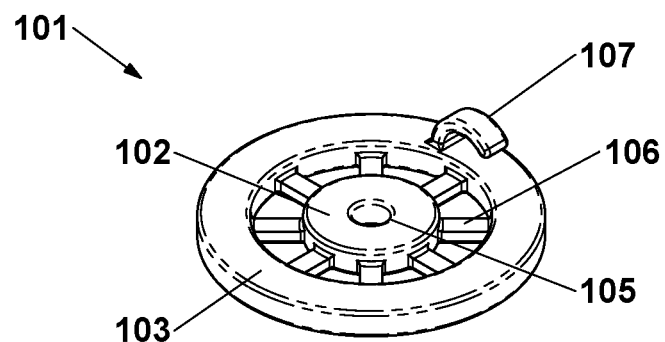
FIG. 1 is a perspective view of a catheter holding device of the present invention.
Figure 2C:
FIG. 2C is a cross-sectional view of the device, taken along the line 2C-2C in FIG. 2.
Figure 2D:
FIG. 2D is another cross-sectional view of the device, taken along the line 2D-2D in FIG. 2.
Figure 2:
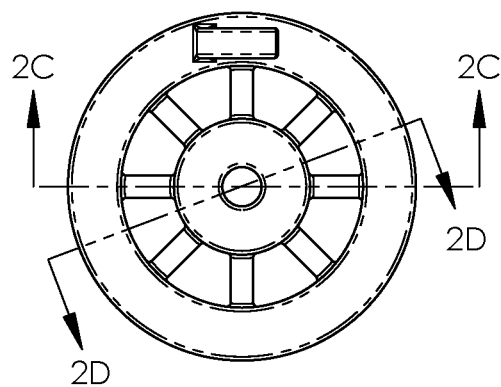
FIG. 2 is a top plan view of the device shown in FIG. 1.
Figure 2B:
FIG. 2B is another side elevation of the device shown in FIG. 2.
Figure 2A:
FIG. 2A is a side elevation of the device shown in FIG. 2.
Figure 3:
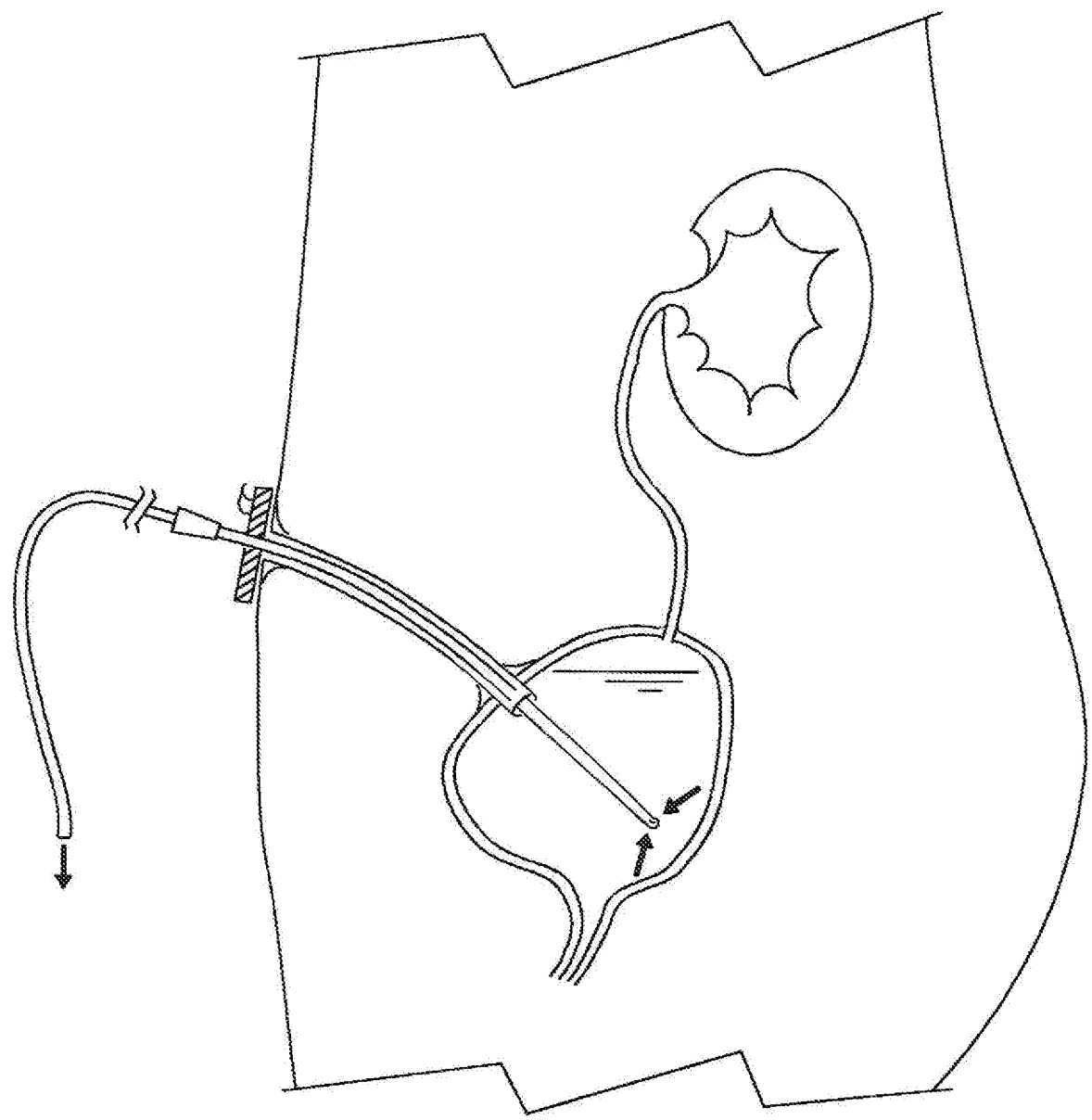
FIG. 3 is a side view pictorial example illustration showing the device of FIG. 1 in use on a medical patient.
Figure 4:
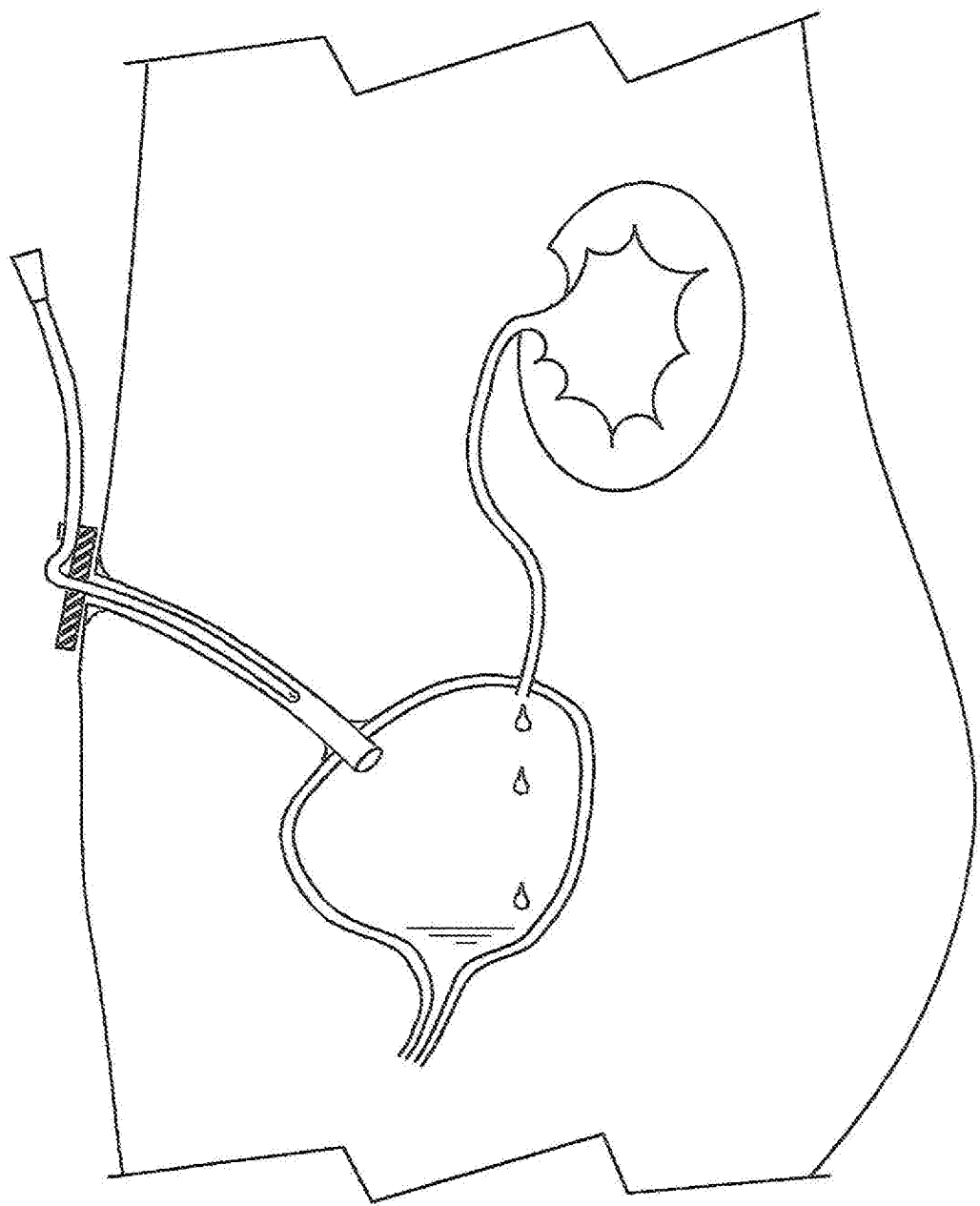
FIG. 4 is another side view pictorial example illustration showing the device of FIGS. 1-3, showing the catheter tube secured by the retaining clip member as desired when the catheter is not being used for fluid drainage purposes.
Figure 5:
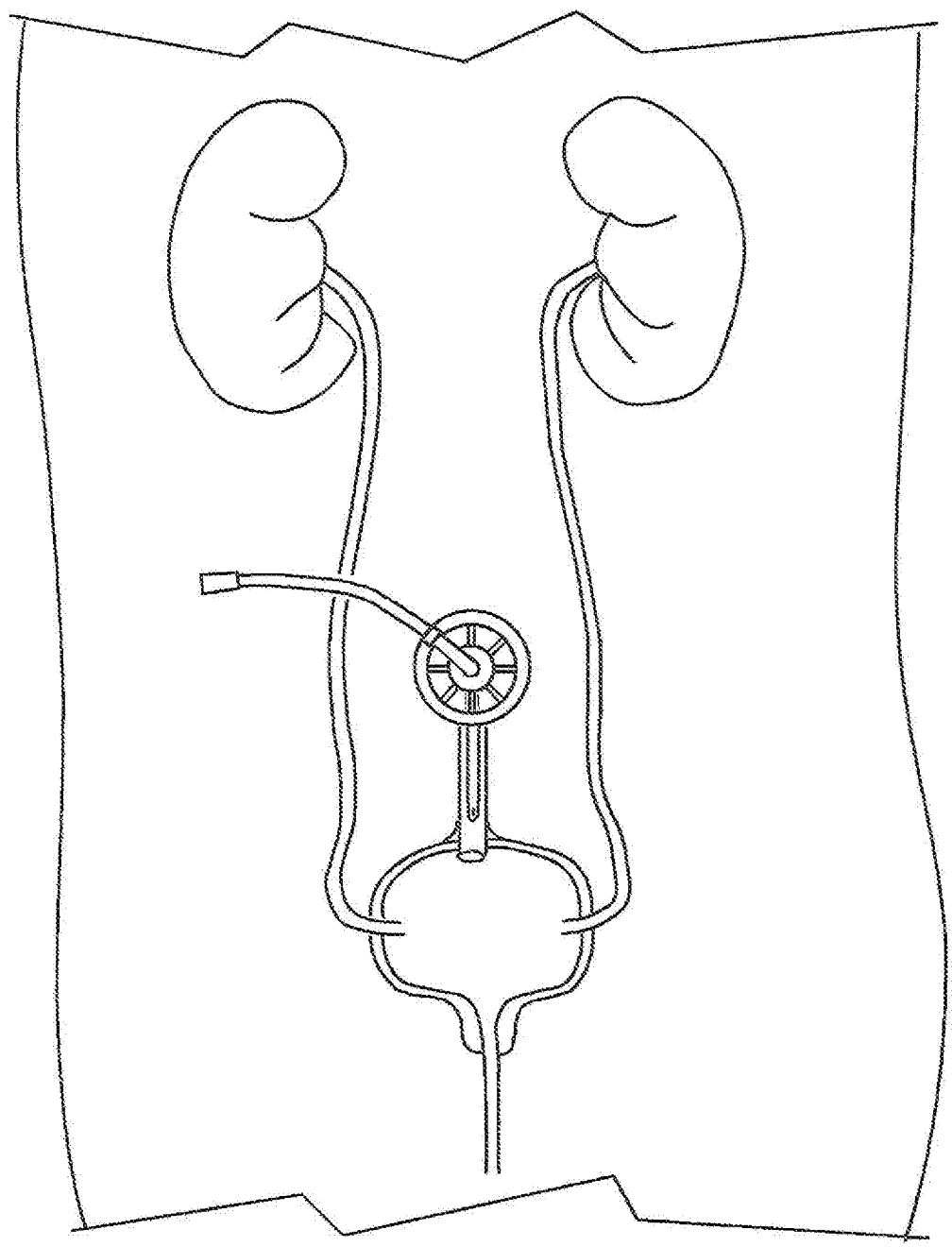
FIG. 5 is a front view pictorial example illustration of the arrangement shown in FIG. 4.

As shown in FIGS. 1 and 2A-D, the external catheter stabilizer device 101, preferably made of surgical plastic or like materials, includes a generally central hub portion 102 including a central opening 105 for receiving and engaging a generally flexible catheter tube, an outer circumference support portion 103 connected to the central hub portion by a series of substantially radial members or spokes 106, and a medical catheter retaining clip portion 107 disposed at the circumference portion for temporarily retaining, securing, and readily releasing a generally flexible medical catheter tube 110 (FIGS. 6, 6A and 6B) by hand as necessary. To provide a sense of size scale of the illustrated device, the approximate dimensions for example are about 46 mm (1.81 inches) outside diameter with a base thickness of about 4 mm (0.15 inches). During use on a medical patient, and such as shown in FIGS. 3-5, the device is applied to the patient and temporarily secures, stabilizes and retains a drainage catheter in position while a catheter tube has been inserted into the body through a surgical stoma into a bladder for drainage of bodily fluid within the bladder and kidneys in this example.

Figure 7:
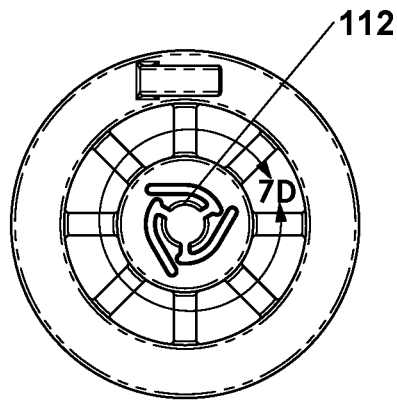
FIG. 7 is a top plan view of another catheter retaining device of the present invention, showing a means of providing greater flexibility and deflection capability at the central catheter engagement hole or opening.
Figure 7C:
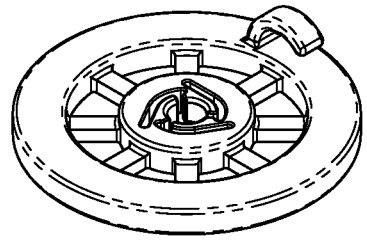
FIG. 7C is a perspective view of the device shown in FIGS. 7, 7A, and 7B.
Figure 7A:
FIG. 7A is a side elevation of the device shown in FIG. 7.
Figure 7B:
FIG. 7B is another side elevation of the device shown in FIG. 7.
Figure 7D:
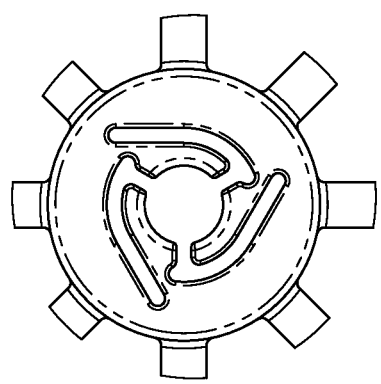
FIG. 7D is an enlarged plan view of the central hub portion of the device shown in FIG. 7.

Optionally, and such as shown in FIGS. 7-7D, the external catheter stabilizer device may include a means of providing greater flexibility and deflection capability at the central catheter engagement hole or opening, whereby the diameter of the hole can slightly change or deflect slightly as needed to accommodate a sliding frictional fit of a wider range of generally flexible catheter tubes than might otherwise be possible with only a fixed diameter hole. In the illustrated embodiment, the hole is surrounded or circumscribed by three flexible elements or arms 112. Each of the three arms around the periphery of the catheter engagement hole are designed to allow an increased degree of deflection by design by means of a reduced cross-sectional area or point of cantilever flexibility and springiness at or near the base-attachment portion of the respective arms at or near to the central hub portion of the device.

Even though the catheter tube itself is understood to be generally soft and flexible, this type of design allows greater flexibility and forgiveness in instances where the outside diameters of the catheter tube may be expected to vary between different suppliers and dimensional tolerance variations. The three small plastic arms at the center are intended to lightly contact and grasp the outside of the catheter tube. This type of design should provide a bit of springiness and deflect just slightly as needed to cover a wider range of catheter tube outside diameters. The thin section dimension of the arms would be selected based on testing and the physical characteristics of the plastic ultimately selected to manufacture and mass-produce these retainers. Additionally, the openings at the plastic arms provide additional thru-open spaces for sterile irrigation and air-flow as likely needed to the critical area of the stoma and catheter tube.

Figure 8:
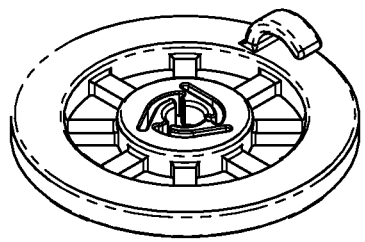
FIG. 8 is another perspective view of the device of FIG. 7, showing an 8-spoke design.
Figure 8A:
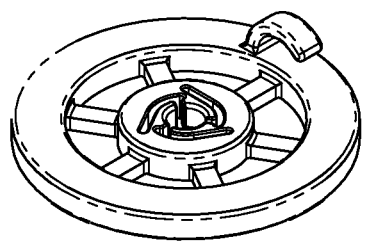
FIG. 8A is a perspective view of another device of the present invention, showing a 6-spoke design.
Figure 8B:
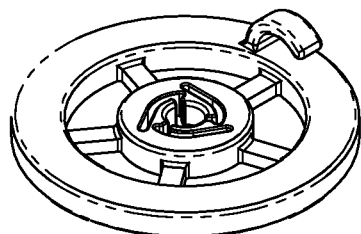
FIG. 8B is a perspective view of another device of the present invention, showing a 5-spoke design.
Figure 8C:
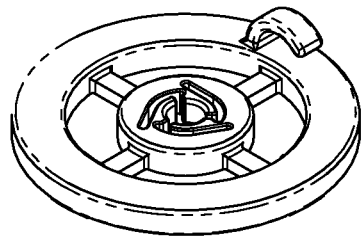
FIG. 8C is a perspective view of another device of the present invention, showing a 4-spoke design.
Figure 8D:
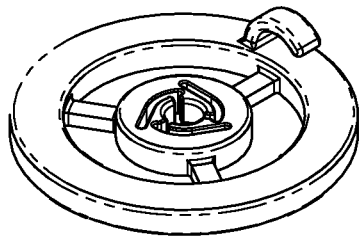
FIG. 8D is a perspective view of another device of the present invention, showing a 3-spoke design.
Figure 9:
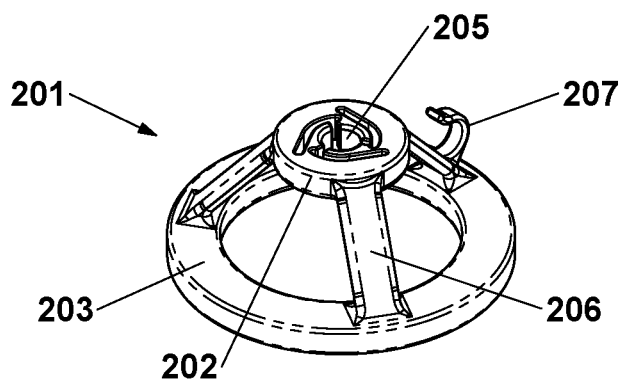
FIG. 9 is a perspective view of another device of the present invention, where the central hub portion of the device has been raised upward with respect to the base or circumferential portion, shown with a 3-spoke design similar to the device shown in FIG. 8D.
Figure 10:
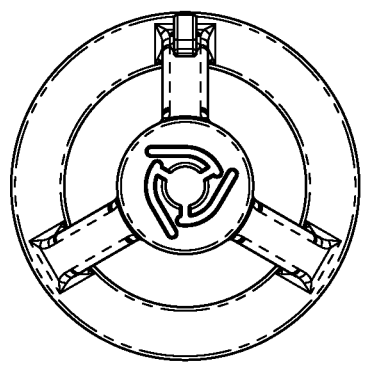
FIG. 10 is a top plan view of the device shown in FIG. 9.
Figure 10B:
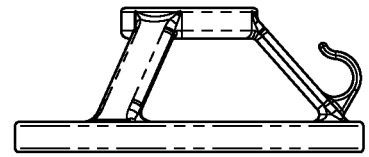
FIG. 10B is another side elevation of the device shown in FIG. 10.
Figure 10A:
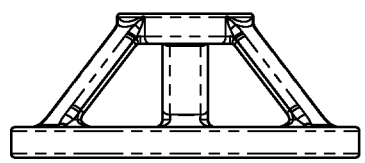
FIG. 10A is a side elevation of the device shown in FIG. 10.

Optionally, the external catheter stabilizer device may have various designs or forms, such as, for example, as shown in FIGS. 8-8D. These represent a series of options related to the number of spokes. Again, based upon maximizing open spaces as stated above, the 8-spoke design can readily evolve into, for example, a 3-spoke design. While the sizes of the spokes may be similar in these examples, the spokes of the 3-spoke version however, could be made thicker (in depth) and stronger if necessary, as well as made vertically narrower, to help further maximize the size of the thru openings around the hub portion. The 3-spoke design may thus offer a generally maximum open viewing area along with good mechanical strength characteristics of the device, and further provides improved physical access and air circulation to the stoma and surrounding skin and body tissues when the device is in use.

Optionally, and with reference to FIGS. 9-11B, the external catheter stabilizer device 201 may comprise a base portion 203 and a raised central hub 202, with the arms or spokes 206 extending between the central hub 202 and base portion 203 to support the central hub above the base portion and away from the patient's skin (when the device is disposed at or attached at a patient). In the illustrated embodiment, the catheter retaining clip portion 207 is disposed at the base of one of the spokes, but could be otherwise disposed elsewhere along a spoke or spokes 206 or at the base portion 203 itself.

Optionally, and with reference to FIGS. 12-17B, the external catheter stabilizer device may have a multi-part base portion 203' to reduce the contact surface area with the patient so as to limit or further prevent irritation to a newly-created and initially-healing stoma. The flat or continuous base portion design of the device of FIGS. 1-8 could potentially irritate the area near a newly created stoma, but could easily be used on an existing well established and substantially healed stoma. The multiple foot or engaging pad designs of FIGS. 12-17B provide for improved ease of release and lift off of the device from the area of a newly-created stoma, for example, such as when medical grade adhesives are being utilized for attachment of the device to the surface of the skin. The height of the hub could vary depending the size of catheters, health of the stoma, location of the stoma, and particular medical application of the stoma or opening in the body of a patient.

Figure 12:
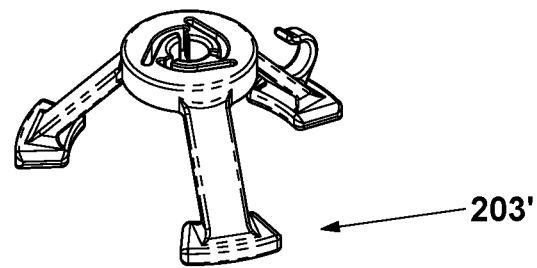
FIG. 12 is a perspective view of another device of the present invention, where the base or circumferential portion of the device shown in FIGS. 9 through 10B has been cut away at three locations providing for a three-contact design with the skin of a medical patient using the device.
Figure 13:
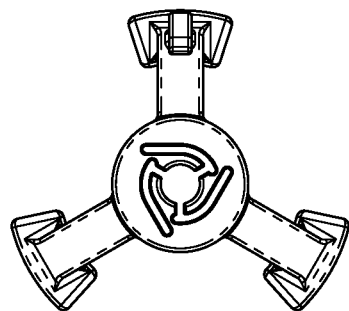
FIG. 13 is a top plan view of the device shown in FIG. 12.
Figure 13B:
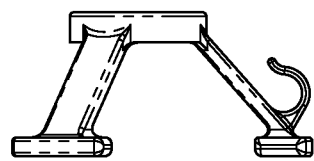
FIG. 13B is another side elevation of the device shown in FIG. 13.
Figure 13A:
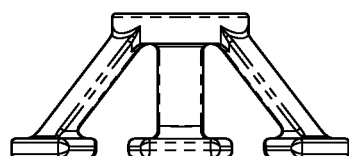
FIG. 13A is a side elevation of the device shown in FIG. 13.
Figure 14:
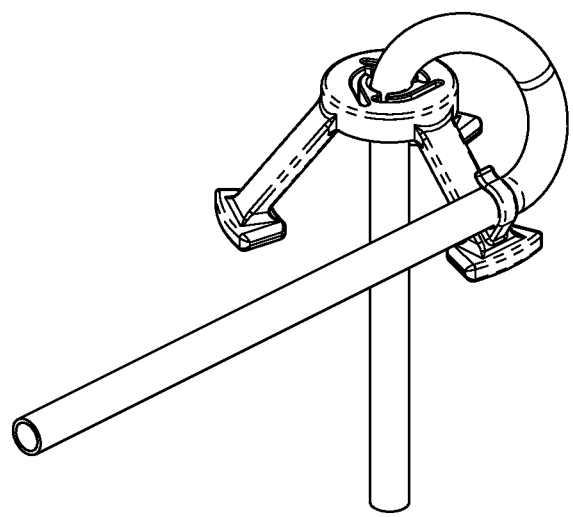
FIG. 14 is a perspective view showing an example arrangement of the device shown in FIGS. 12 through 13B, with an example of a catheter tube engaged and temporarily clipped into place.
Figure 14A:
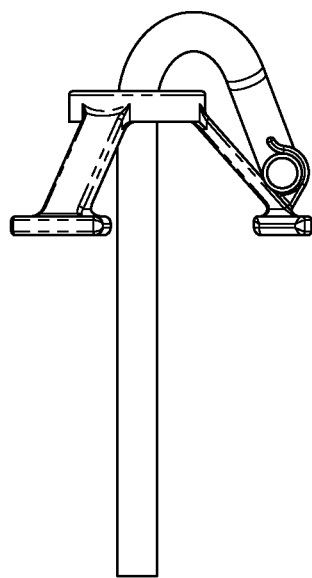
FIG. 14A is a side elevation of the example arrangement of shown in FIG. 14.
Figure 14B:
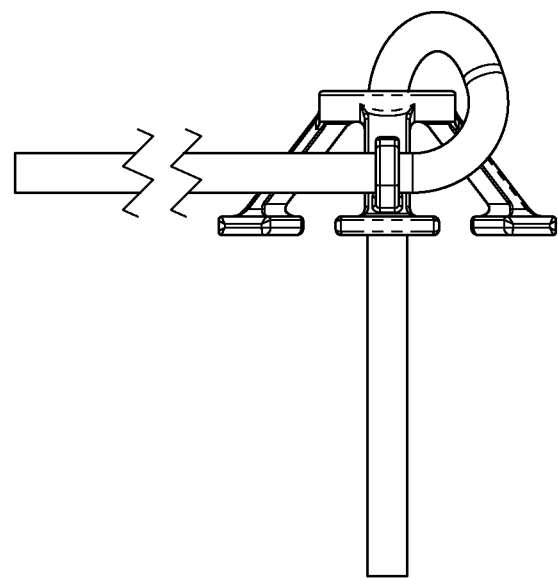
FIG. 14B is another side elevation of the example arrangement shown in FIG. 14.
Figure 15:
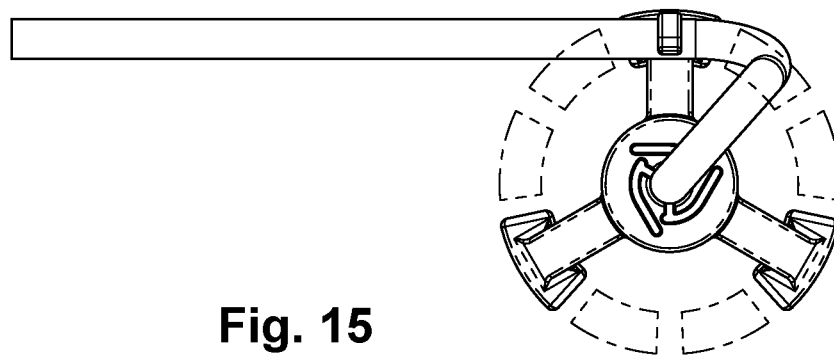
FIGS. 15, 15A, and 15B illustrate the 3-position indexing capability of the 3-leg contact design of the device of FIG. 12.
Figure 15A:
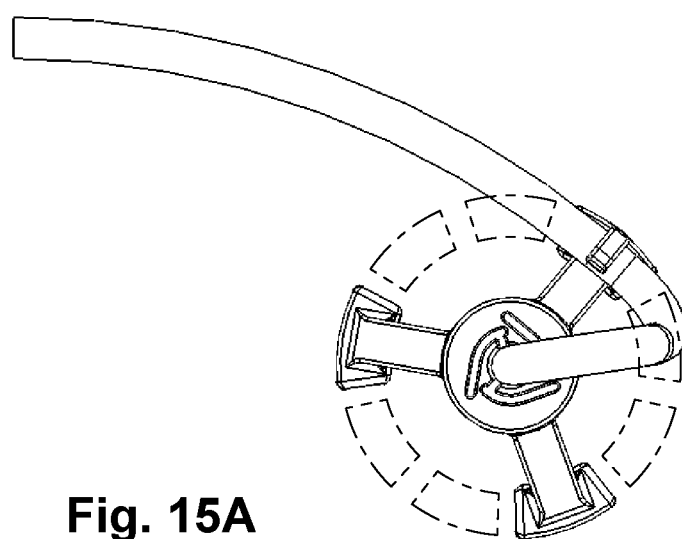
Figure 15B:
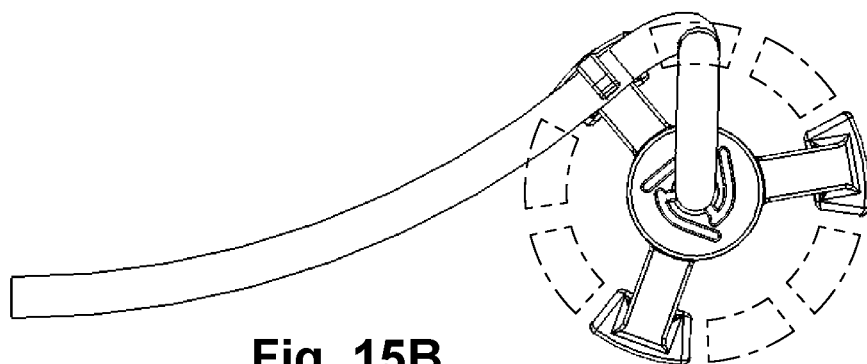
Figure 16:
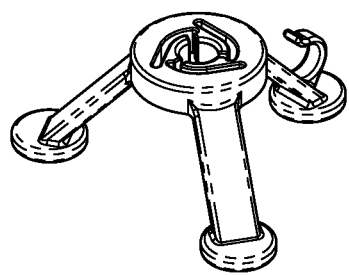
FIG. 16 is a perspective view of another device of the present invention, with the base or skin contact portions of the device shown as small round pads which can help to further reduce the total contact area with the skin.
Figure 17:
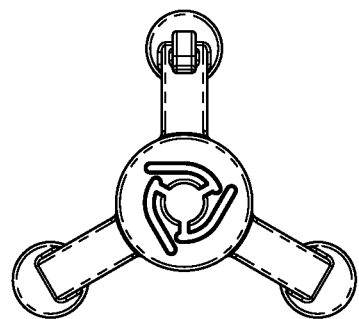
FIG. 17 is a top plan view of the device shown in FIG. 16.
Figure 17B:
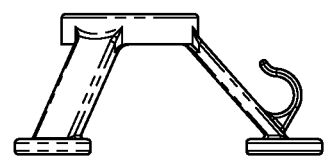
FIG. 17B is another side elevation of the device shown in FIG. 17.
Figure 17A:
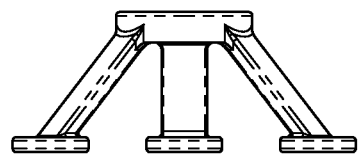
FIG. 17A is a side elevation of the device shown in FIG. 17.
Figure 18:
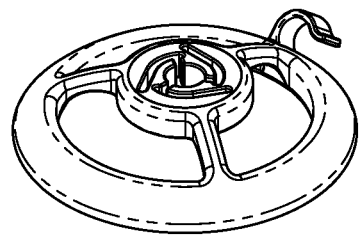
FIG. 18 is a perspective view of another device of the present invention, where the overall height of the device has been reduced to nearly half of the overall height of the previous raised central hub designs.
Figure 19:
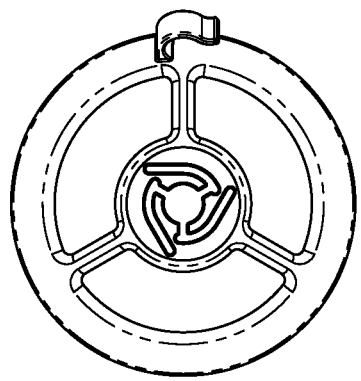
FIG. 19 is a top plan view of the device shown in FIG. 18.

As shown in FIGS. 15, 15A, and 15B, the external catheter stabilizer device may provide a 3-position indexing capability of the 3-leg contact design (see FIG. 12). This allows the skin attachment areas time to recover when the device is periodically rotated or indexed to one of three available positions in this case, at the same location on the skin. Attachment to the skin of a patient would typically utilize, for example, medical grade adhesives or silicone, tape, Velcro pads and other foreseeable methods and means for attachment to the skin. Also, the three legs could be optionally generally curved (more dome-shaped) or straight as shown in FIGS. 18-19A (and may connect the central hub to individual respective pads or a continuous circular base portion as shown). As shown in FIG. 16, the base or skin contact portions of the device are shown as small round pads which can help to further reduce the total contact area with the patient's skin. This may be beneficial depending upon the specific means and method of attachment to the skin for example when relatively higher strength temporary medical adhesives are used.

The addition of feet may include a flexible mechanical foot-joint attachment to the bottom of each of the legs. For example, the feet or pads may comprise a series of three small ball and sockets that would snap-together. The round sockets may be incorporated into each of the bottom surfaces of the respective feet, while the round ball attachment may be incorporated into the actual foot-pad. This would allow a much greater degree of freedom of angular movement and flexibility of attachment to uneven surfaces of the body and skin, helping any adhesive or Velcro attachments to remain better secured. Additionally, it is anticipated that the mechanical round ball and socket joints could be replaced by relatively small and highly flexible polymer medical grade materials which may readily bond well to plastic, for example. This type of a configuration, as compared to a mechanical ball and socket flexible foot design, would provide further simplicity to the design of the device and help to further avoid the potential for small openings and crevasses, where potential contaminants that may lead to a higher risk of infection might otherwise reside.

Figure 19B:
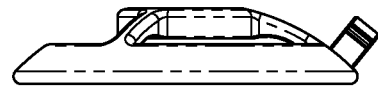
FIG. 19B is another side elevation of the device shown in FIG. 19.
Figure 19A:
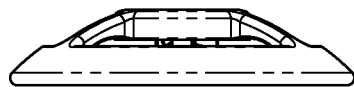
FIG. 19A is a side elevation of the device shown in FIG. 19.

Optionally, and as shown in FIGS. 18-19B, the external catheter stabilizer device may have a reduced overall height to nearly half of the overall height of the previous raised central hub designs. This design is intended to be contoured as low and smoothly as possible to further avoid any sharp corners and edges which have the potential to catch on clothing or hospital bedding, for example. Additionally, the smooth contours are intended to provide for increased ease of cleanliness to help avoid the potential for infection or injury. Additionally, this design embodiment will offer further advantages toward ease of manufacturing and reduced costs related to molded medical plastic production processes and like materials.

Figure 20:
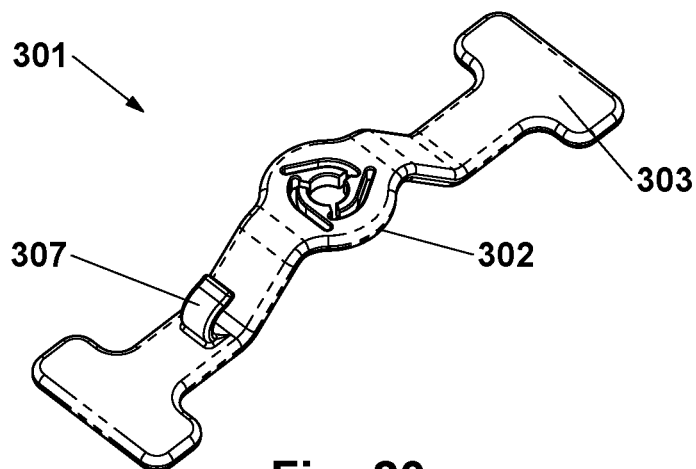
FIG. 20 is a perspective view of another device of the present invention, where a generally elongated member includes a raised center portion and expanded areas at each of its two ends providing increased surface area for both improved transverse directional stability and greater contact area for use of medical adhesives or tape for the purpose of attachment to the skin.
Figure 21:
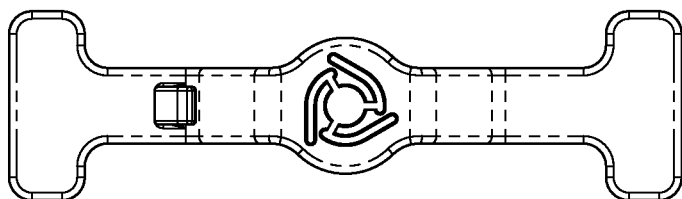
FIG. 21 is a top plan view of the device shown in FIG. 20.
Figure 21A:
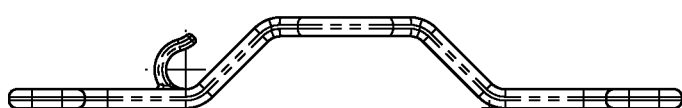
FIG. 21A is a side elevation of the device shown in FIG. 20.
Figure 21B:
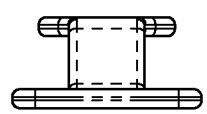
FIG. 21B is an end elevation of the device shown in FIG. 20.
Figure 21C:
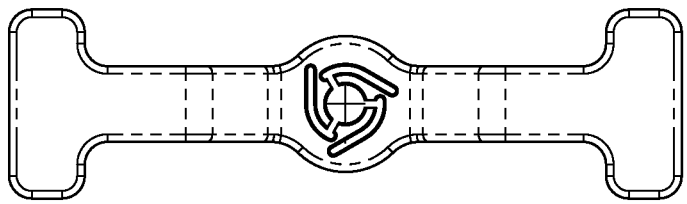
FIG. 21C is a bottom plan view of the device shown in FIG. 20.

Optionally, and as shown in FIGS. 20-21C, the external catheter stabilizer device 301 may have an elongated configuration or design that departs from the hub and spoke designs discussed above. This elongated design offers geometric advantages promoting enhanced air-flow and visibility to the stoma area of the skin for example, just below the central portion 302. The wider distal end portions 303 provide a larger contact surface area with the skin of the patient when either medical adhesives or medical adhesive tape is used to secure the device to the skin. The "T-shape" of the distal ends can further resist any typical "pull-out" forces when medical adhesive tape is being used. The wider distal end portions further provide enhanced lateral or transverse stability to the inherent longitudinal stability provided by this 2-point contact configuration. When alternately rotated to optional positions about an axis of rotation at the stoma site for example, this longitudinal design defines a relatively large diameter circle allowing for periodic rotational indexing of the attachment feet at different areas of the skin. This can allow the skin at the contact areas to "take a break" from exposure to medical adhesive or tape while the device is in prolonged or continuous use, therefore helping to reduce the likelihood of skin irritation. Optionally, and by design, a second catheter retaining device or hook 307 may be added to the opposite side in addition to the first one as shown. This second retaining device can offer a quick and immediate alternate routing of the catheter tube the other way around for example. This can be especially handy to allow for additional adjustment or flexibility of the tube routing after the device is securely attached to the skin of the patient.

Optionally, and as shown in FIGS. 22-23B, the external catheter stabilizer device comprises a three-leg design having similar design features and advantages as the device shown in FIGS. 20-21C and discussed above. This embodiment of the present invention provides the advantages of ideal or near-ideal geometric stability, while the optional three catheter retaining devices again offers a variety of up to six immediate and alternate routing options for the catheter tube as desired during installation and use of the device on the patient.

Optionally, as shown in FIGS. 24-25C, another version of an elongated external catheter stabilizer device 401 comprises a raised center portion 402 supported by a generally elliptical-shaped dome 406, resembling the shape of a portion of a football, including a widened-edge base at the bottom contact surface at the skin and longitudinal extensions or paddles 403 at each end. The longitudinal extensions or paddles at each end provide increased surface area for the use of medical adhesive at the underside of the paddles or medical tape applied over the paddles at each side for attachment of the device to the skin of the patient. There is a hole at the center of the "football" of variable size, which is to be centered over the surgical stoma that receives the catheter tube where the drainage tube is to be inserted, thus providing substantially perfect alignment of the drainage tube with the opening of the stoma. Openings are provided at four positions around the elliptical-shaped dome for facilitating post-surgical observation and visual inspection of the stoma site for example, as well as free air-flow and ventilation for the surrounding tissue. A catheter retaining device or hook is provided at one end allowing two options for routing and securing the catheter tube in place. Optionally, a second catheter retaining device may be added to the opposite end (not shown), thus providing more (such as up to four) catheter routing and securing options.

Figure 26:
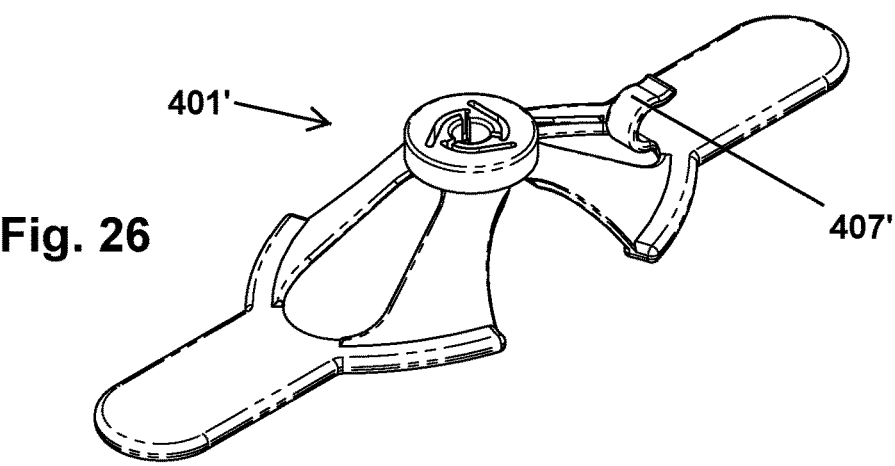
FIG. 26 is a perspective view of another device similar to the device shown in FIG. 24, shown with the catheter retention feature or hook reversed or turned around to the opposite direction.
Figure 27:
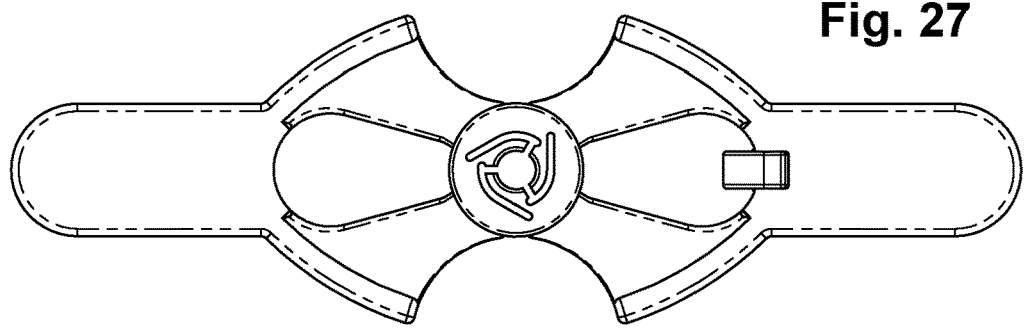
FIG. 27 is a top plan view of the device shown in FIG. 26.
Figure 27B:
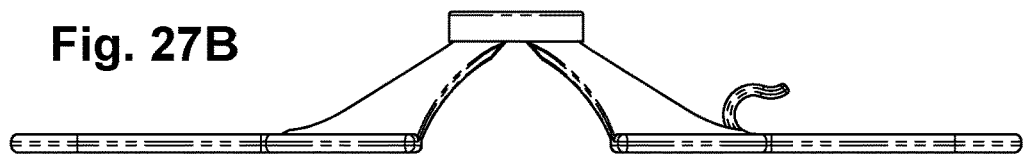
FIG. 27B is a side elevation of the device shown in FIG. 26.
Figure 27C:
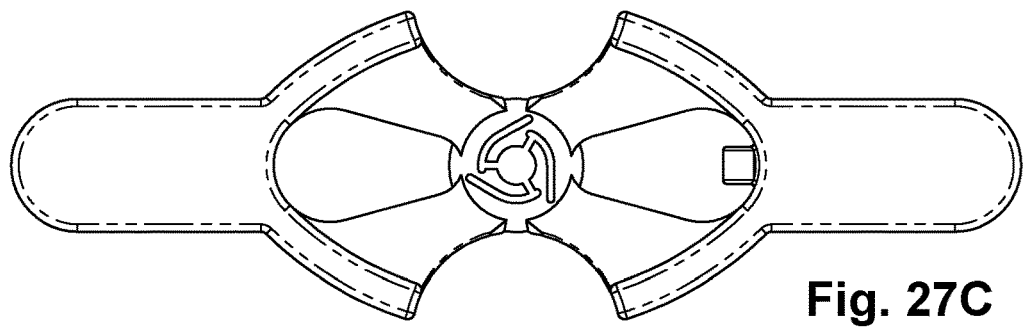
FIG. 27C is a bottom plan view of the device shown in FIG. 26.
Figure 27A:
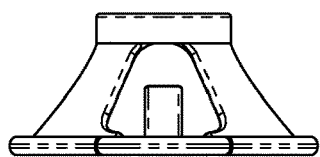
FIG. 27A is an end elevation of the device shown in FIG. 26.

Optionally, as shown in FIGS. 26-27C, the catheter retaining device or hook 407' is turned around as an alternate design option for the device 401'. Optionally, a second catheter retaining device or hook may be added to the opposite end (not shown), thus again providing up to four catheter routing and securing options.

Figure 28:
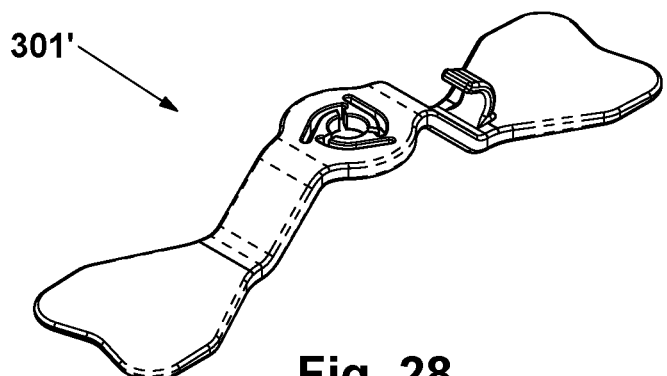
FIG. 28 is a perspective view of another device similar to the device shown in FIG. 20, shown with the generally elongated member including a raised center portion and further expanded surface areas at each of its two ends, thus providing further increased surface areas for both improved transverse directional stability and greater contact area for use of medical adhesives or tape for attachment to the skin, and shown with its distal ends tapered to reduce the thickness and bulk of the material at the end portions of the device.
Figure 29:
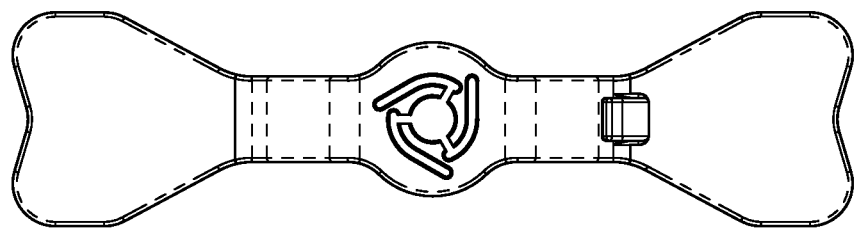
FIG. 29 is a top plan view of the device shown in FIG. 28.
Figure 29B:
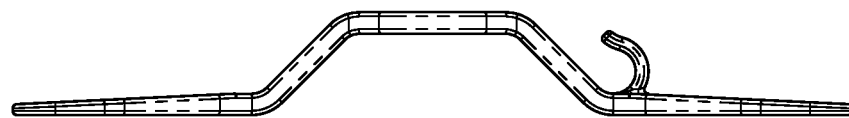
FIG. 29B is a side elevation of the device shown in FIG. 28.
Figure 29C:
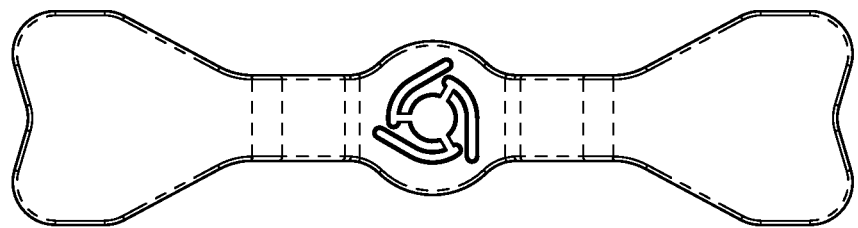
FIG. 29C is a bottom plan view of the device shown in FIG. 28.
Figure 29A:
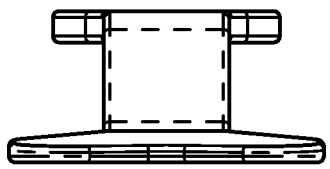
FIG. 29A is an end elevation of the device shown in FIG. 28.

Optionally, as shown in FIGS. 28-29C, another elongated external catheter stabilization device 301' similar to that shown in FIGS. 20-21C is shown. This embodiment of the device provides increased surface areas at the distal ends beyond that of device shown in FIGS. 20-21C. The increased surface areas offer increased security for attachment to the skin with medical adhesives or tape while the tapered ends help to reduce material thickness and bulk of material. When medical tape is used to attach the device to the skin, the tapered portions offer a smoother transition between the device and the surface of the skin for better tape adhesion and conformity of the tape between the respective surfaces. This design feature further promotes device stability and security of the external catheter retaining device when in place on the patient.

Figure 30:
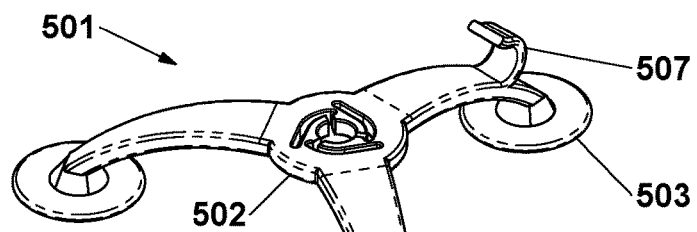
FIG. 30 is a perspective view of another device of the present invention, shown with three radial support extensions comprising the structural support of the center portion, and further including three circular pads or feet at each distal end of the radial support extensions comprised of generally rigid medical grade plastic each attached by means of a substantially flexible medical grade elastic polymer plastic all permanently bonded into a single unit, and shown with a catheter retaining feature or hook included at one of the radial support extensions.
Figure 31:
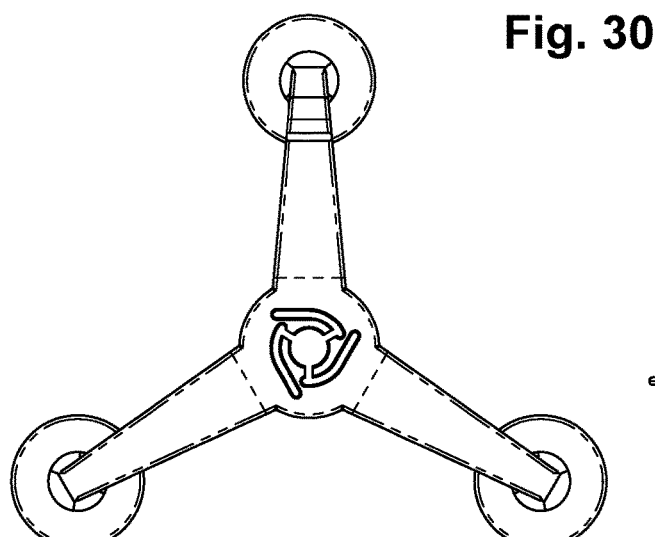
FIG. 31 is a top plan view of the device shown in FIG. 30.
Figure 31B:
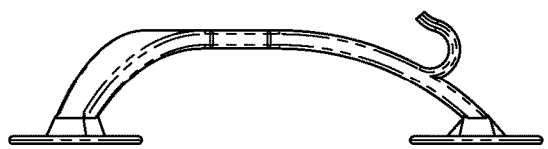
FIG. 31B is another side elevation of the device shown in FIG. 30.
Figure 31A:
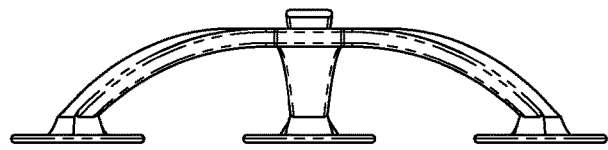
FIG. 31A is a side elevation of the device shown in FIG. 30.
Figure 31C:
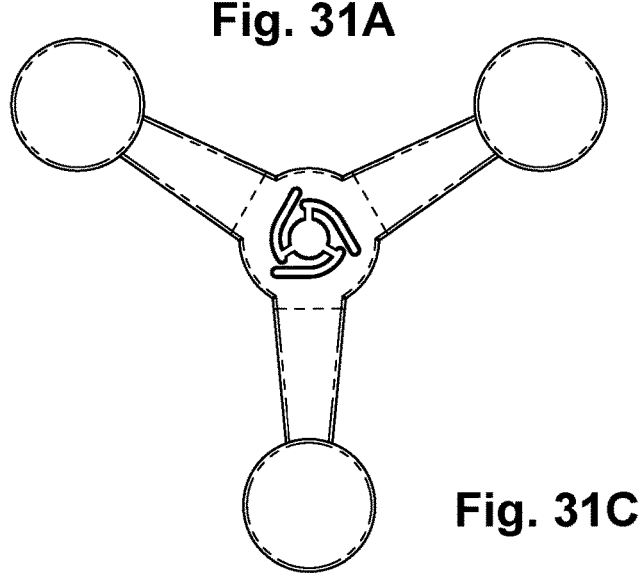
FIG. 31C is a bottom plan view of the device shown in FIG. 30.

Optionally, as shown in FIGS. 30-31C, another version of external catheter stabilizer device 501 comprises a three-leg design having a few similarities and advantages as the device shown in FIGS. 22-23B. This device of the present invention provides near-ideal geometric stability and comprises three structural support members 506 extending radially from a raised center portion 502 that includes a passageway or aperture for a generally flexible catheter tube to pass therethrough. The retaining hook 507 is disposed at or near a lower end of one (or more) of the spokes or support members 506, such as near the base or pads 503. The center portion and structural support members may comprise, for example, medical grade substantially rigid polymer plastic. The material and cross-sectional design of the members may be selected for good strength and rigidity characteristics, for example based upon the anticipated loads and forces experienced during normal use of the device.

Three circular pads 503 are adapted and secured to the distal ends of the three support members and provide skin contact surface areas for attachment to the skin of the patient using either medical adhesive or tape. The entire device may be formed or otherwise molded from a substantially rigid polymer plastic throughout. Optionally, however, small sections of thermoplastic elastomer (TPE) may be used to permanently bond the three circular pads at each of the distal ends of the support members. The TPE sections are designed to provide a substantial degree of flexibility at each of the circular pads with respect to the three support members, thus allowing the respective bottom contact surface of the pads to more readily conform to any generally uneven surfaces or overall contours of the patient's body and skin. The conformity of the circular pads allows the medical adhesive or tape to become more efficient in its attachment through reduced exposure to peel strength loads, as well as increased exposure to normal (as in direction) pull-strength loads, when the external retaining device is in place and in use by the patient. Optionally, the diameters and overall shape of the circular pads may be configured by design to achieve the desired levels of mechanical performance in their attachment to the patient's skin.

A further advantage of permanently bonded flexible joints between each of the substantially rigid plastic structural support legs and circular contact pads is that a smooth and uniform surface finish at each flexible joint is achievable in the final assembly of the device. This aspect can help to eliminate mechanical joints and crevasses that could harbor bacteria and potentially harmful debris which might be otherwise be hazardous to the successful and rapid healing of the patient.

A further advantage of this design is that it offers significantly improved visibility to the stoma area by, for example, medical personnel, and provides significantly improved circulation of air and ventilation and relative ease of access for maintenance, cleaning and irrigation of the stoma site.

Figure 32:
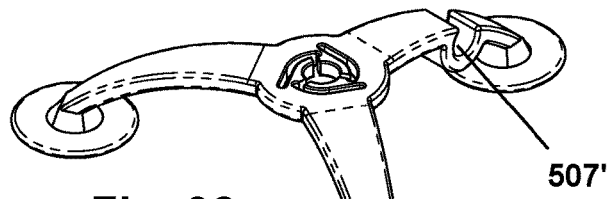
FIG. 32 is a perspective view of another device similar to the device shown in FIG. 30, where the catheter retaining feature is included and fully incorporated into and within the generally outer profile of one of the radial support extensions.
Figure 33:
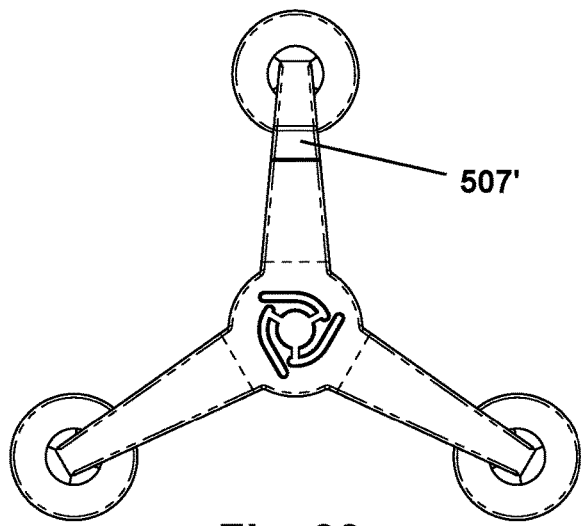
FIG. 33 is a top plan view of the device shown in FIG. 32.
Figure 33B:
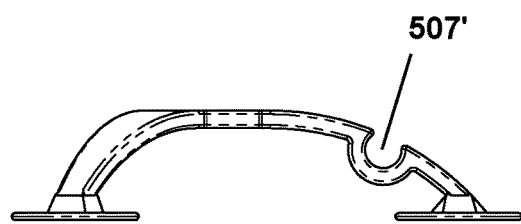
FIG. 33B is another side elevation of the device shown in FIG. 32.
Figure 33A:
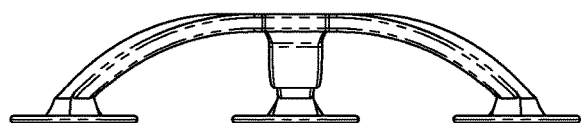
FIG. 33A is a side elevation of the device shown in FIG. 32.
Figure 33C:
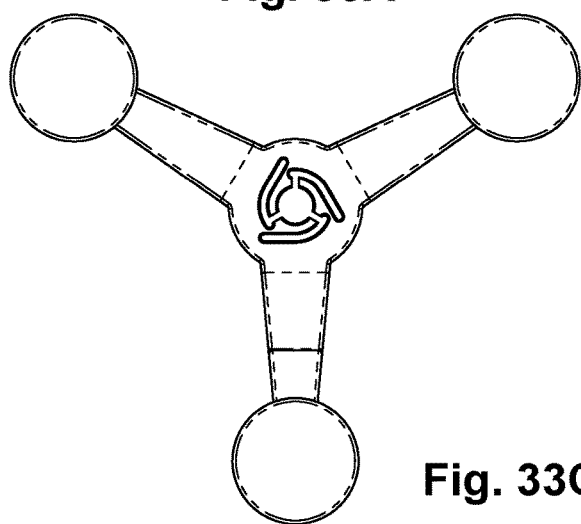
FIG. 33C is a bottom plan view of the device shown in FIG. 32.

Optionally, as shown in FIGS. 32-33C, another external catheter stabilizer device comprises a three-leg design having similarities and advantages of the device shown in FIGS. 30-31B. This device incorporates the catheter retaining feature 507' into one of the structural support members of the device. The outer profile of the device is reduced considerably to reduce the likelihood of the device inadvertently catching on clothing, hospital bedding, or other items. Leg strength and rigidity of the device may be compromised slightly. However, with proper thickening of the plastic and careful selection of the material radii near the catheter retainer, this concern is significantly diminished. The further advantage of this design aspect is that when the catheter tube in clipped into place at the retainer (which comprises a clip element formed in one of the legs and below the outer or upper surface of the leg), the likelihood of catching things is reduced even further by the fact that the catheter tube itself helps prevent things from getting caught in the U-shaped opening in the first place.

Figure 34:
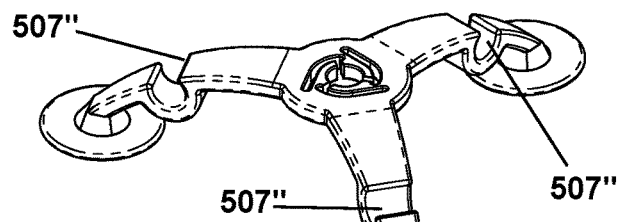
FIG. 34 is a perspective view of another device similar to the device shown in FIG. 32, where the catheter retaining feature is included and fully incorporated into and within the generally outer profile of each of the three radial support extensions.
Figure 35B:
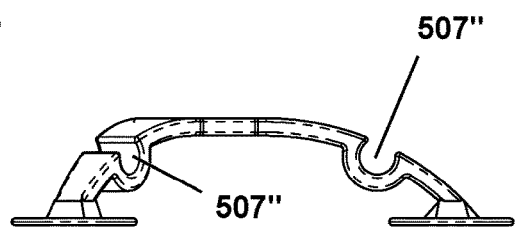
FIG. 35B is another side elevation of the device shown in FIG. 34.
Figure 35:
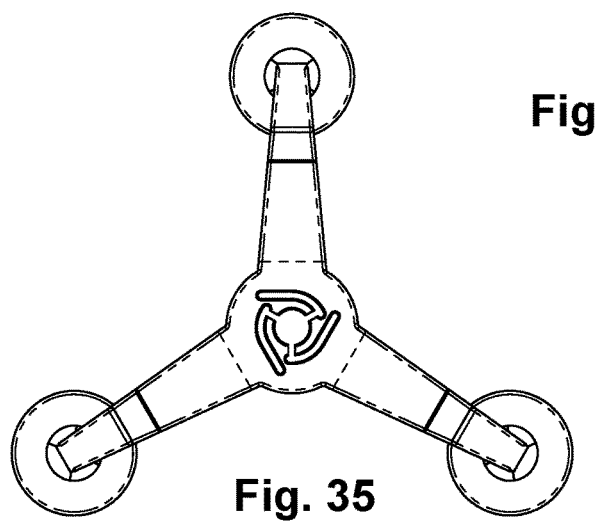
FIG. 35 is a top plan view of the device shown in FIG. 34.
Figure 35A:
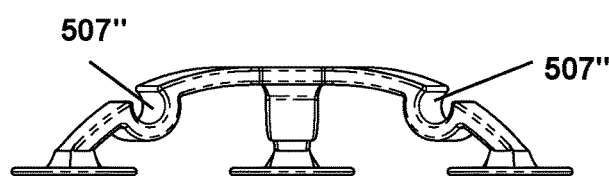
FIG. 35A is a side elevation of the device shown in FIG. 34.
Figure 35C:
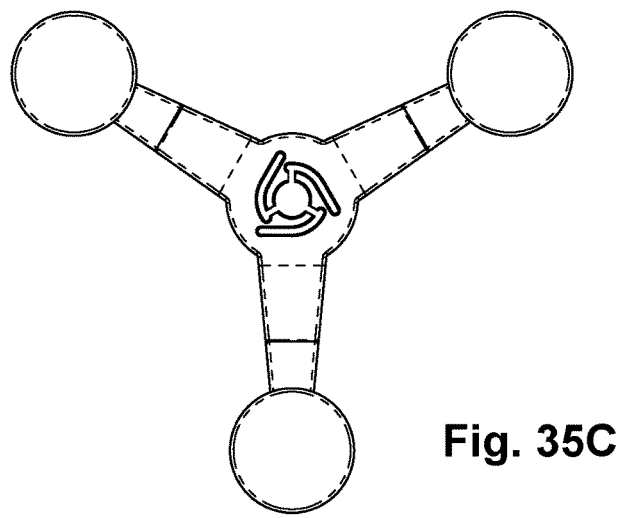
FIG. 35C is a bottom plan view of the device shown in FIG. 34.

Optionally, as shown in FIGS. 34-35C, another external catheter stabilizer device comprises a three-leg design having similarities and advantages of the device shown in FIGS. 32-33C. This device incorporates the catheter retaining feature 507" into all three of the structural support members of the device. This design configuration offers the advantage of allowing up to six routing options for the catheter tube in that the tube can be routed in either direction at any one of the three different locations. It may be optional and preferable to provide at least two small snap-in filler pieces to temporarily fill-up or occupy the two remaining and otherwise unused and empty catheter retainer openings to help avoid inadvertently catching on clothing, hospital bedding, or the like. Such filler pieces would preferably be formed such that, when disposed within the retaining feature, the outer surface of the filler piece generally corresponds with the outer contour of the arm or spoke of the device to further reduce possibility of catching on clothing or the like.

Optionally, as shown in FIGS. 36-37C, another external catheter stabilizer device 401" is shown that is similar to that shown in FIGS. 26-27C. In this embodiment, the device has been somewhat simplified. The two openings at the elliptical-shaped dome have been eliminated by design in favor of two larger openings at the sides. Additionally, four larger radii have been added to the "bottom inside corners", increasing visibility and air-flow even more and further adding greater comfort to the patient by eliminating the relatively sharper corners of the earlier design. A simple central hole is provided for the catheter tube as well as a thicker catheter retainer since this particular simplified design is favored for 3-D prototype printing including typical limitations of detailed resolution for concept evaluation and testing.

Optionally, as shown in FIGS. 38-39C, the device 401''' is substantially the same or identical to the device shown in FIGS. 36-37C. In this case however, it has been dimensionally and generally down-sized or scaled to about 80 percent (e.g., 20 percent smaller) of the device shown in FIGS.

36-37C. This design configuration is intended for use on a smaller person or a child, for example, while all the previous embodiments are generally intended for use on adults, for example. In this example, the inside diameter of the center hole and catheter retainer remains the same as the larger versions being designed for a 5.20 mm diameter catheter tube. Again, this simplified design is favored for 3-D prototype printing including typical limitations of detailed resolution for concept evaluation and testing.

Optionally, as shown in FIGS. 40-41C, the device 401'''' is similar to the device shown in FIGS. 38-39C, with the central portion of the device thickened along with the outer diameter having also been increased for added strength of the device at the relatively narrow (when viewed from the plan views of FIGS. 41 and 41C) central portion. Additionally, the distal ends are re-shaped to a more circular profile (when viewed from the plan views of FIGS. 41 and 41C). The more circular shape of the distal ends can further resist any typical "pull-out" forces when medical adhesive tape is used to attach the device to the surface of the patient's skin. Again, this simplified design is favored for 3-D prototype printing including typical limitations of detailed resolution for concept evaluation and testing.

Optionally, as shown in FIGS. 42-43C, the device 451 is similar to the device shown in FIGS. 40-41C, with the overall height of the center portion being reduced to further increase the overall stability of the device. The raised center portion has been more completely integrated into the dome-shaped central support structure while maintaining sufficient material thickness for strength. The various edges that define the outer-most profile of the device (as best viewed from the top plan view of FIG. 43 and perspective view of FIG. 42) show an increase in the upper fillet radii. These increased radii are advantageous because, when medical tape is used to attach the device to the skin, the various radii offer a smoother transition between the device and the surface of the skin for better tape adhesion and conformity of the tape between the respective surfaces. This design feature further promotes device stability and security of the external catheter retaining device when in place on the patient. Again, the more circular shape of the distal ends can further resist any typical "pull-out" forces when medical adhesive tape is being used to attach the device to the surface of the patient's skin. Again, this simplified design is favored for 3-D prototype printing including typical limitations of detailed resolution for concept evaluation and testing.

Figure 44:
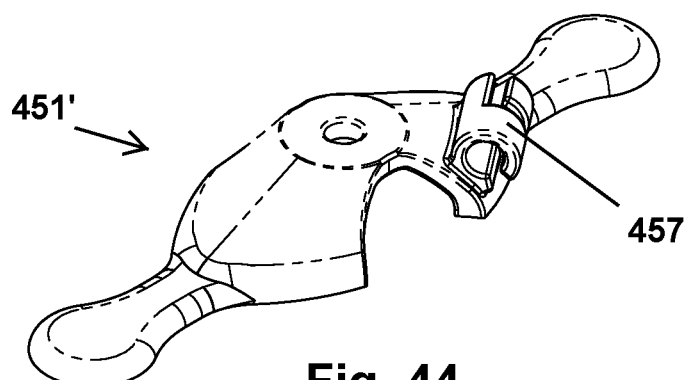
FIG. 44 is a perspective view of another device similar to the device shown in FIG. 42, where the catheter retaining element is revised as well as placed to one side of the device.
Figure 45:
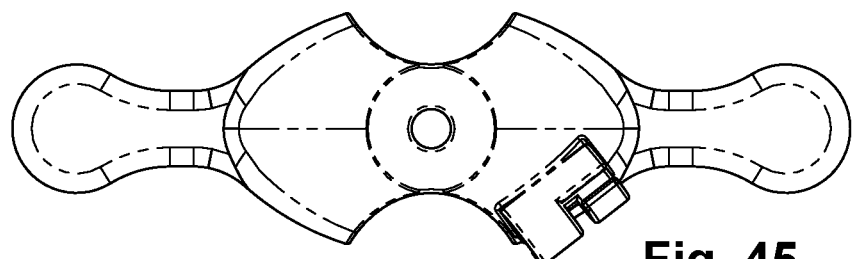
FIG. 45 is a top plan view of the device shown in FIG. 44.
Figure 45B:
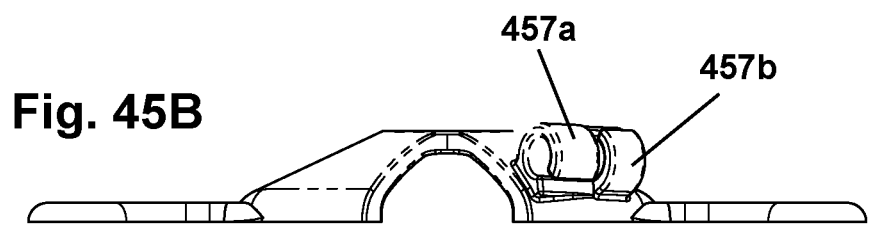
FIG. 45B is a side elevation of the device shown in FIG. 44.
Figure 45C:
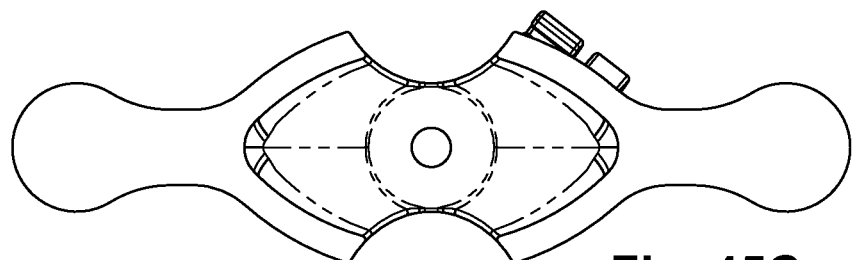
FIG. 45C is a bottom plan view of the device shown in FIG. 44.
Figure 45A:
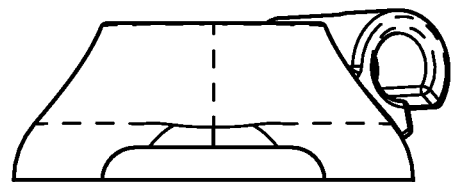
FIG. 45A is an end elevation of the device shown in FIG. 44.

Optionally, as shown in FIGS. 44-45C, the device 451' may be similar to the device shown in FIGS. 42-43C. In this case, an alternate design and location of the catheter retainer 457 is shown. This alternate design is provided to allow the flexible catheter tube to be pushed into the retainer in "zig-zag" fashion between the gaps of the two retaining elements 457a, 457b (FIG. 45B). The alternate location at the side of the device offers a slightly more streamlined routing path for the catheter tube as it is routed outward and away from the device with respect to the overall longitudinal orientation of the external catheter stabilizer. This is especially advantageous as the longitudinal orientation of the device is intended to be approximately or substantially parallel to the transverse or side-to-side direction across the body of the patient.

It is noted that this orientation may be a preferred orientation for all predominantly longer than wide or longitudinal embodiments herein described. This general orientation allows the patient greater freedom of movement while bending such as, for example, when moving from a reclined position to a sitting-up position in bed. In another example, with the longitudinal direction of the device parallel to the floor with a patent that is standing upright, the patient will be able to bend forward more readily and easily without disturbing the external catheter stabilizer and its associated adhesive tape or medical adhesives, as might otherwise be the case if it was positioned generally more vertically at the patient's body.

Figure 46:
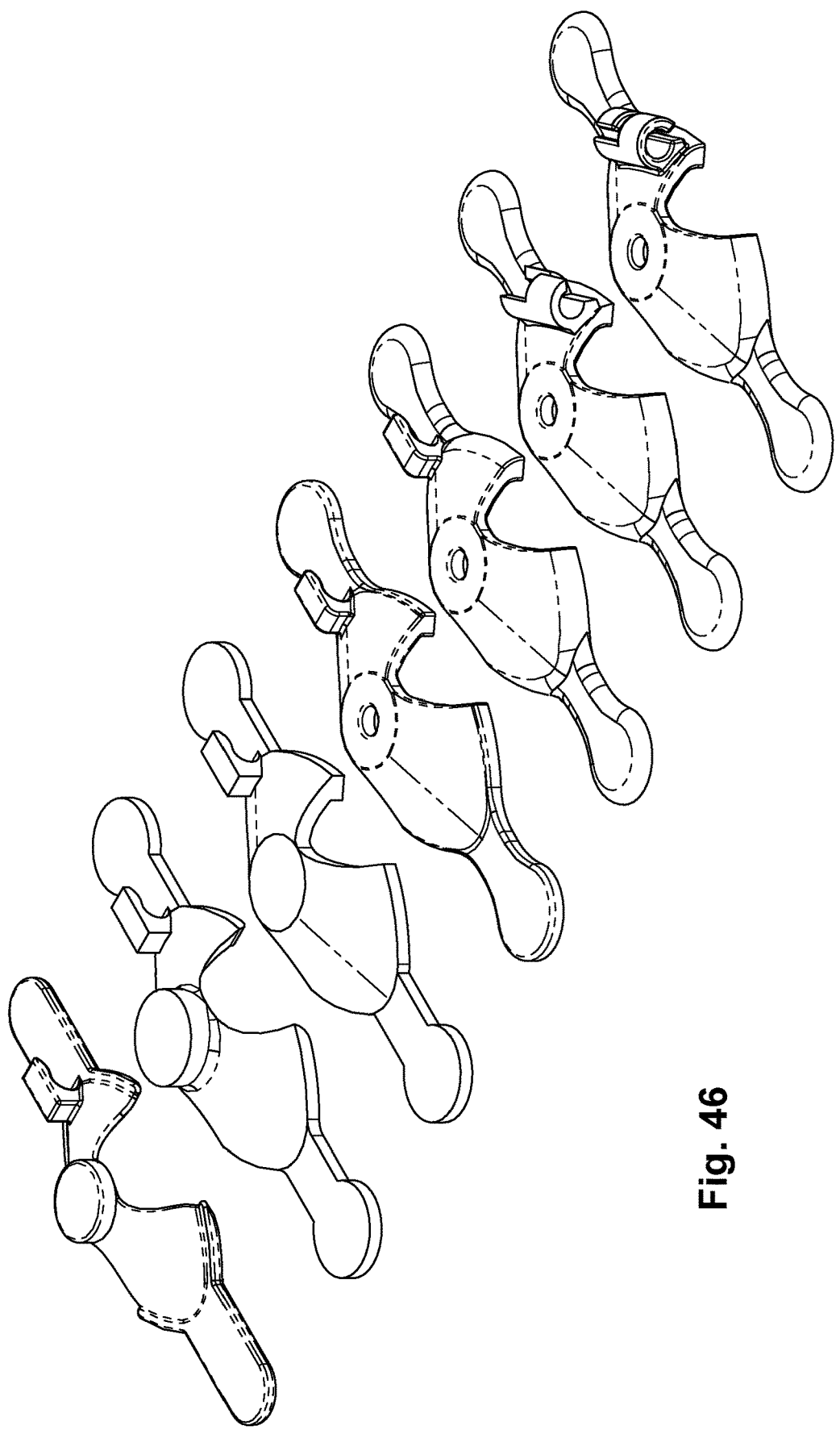
FIG. 46 is a perspective view of an illustrative example of various embodiments of the present invention, with some of the embodiments shown without a catheter opening.
Figure 51:
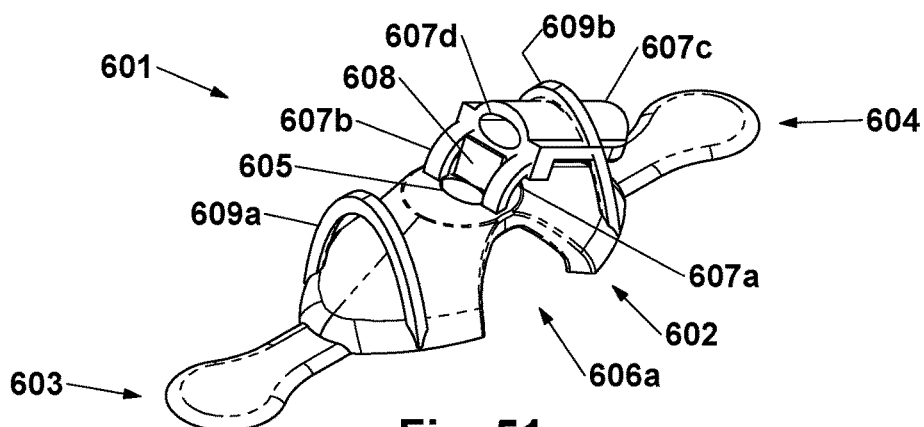
Figure 52:
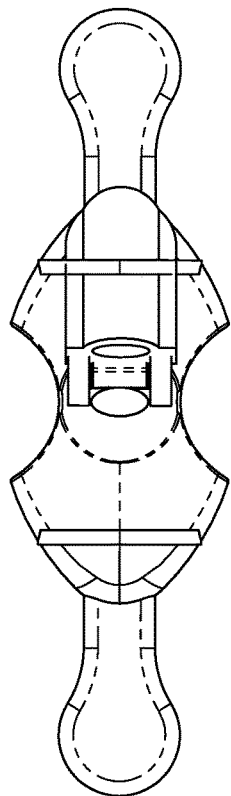
Figure 52B:
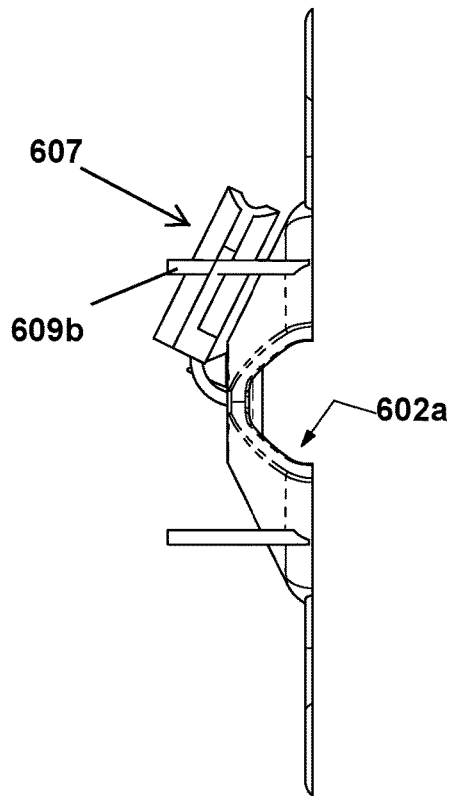
Figure 52C:
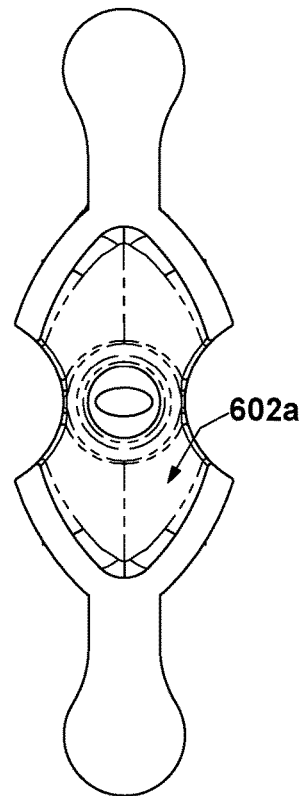
Figure 52A:
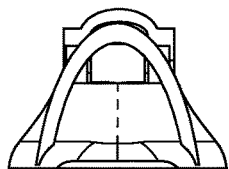

FIG. 46 provides an illustrative example of the progressive development of at least one of the preferred embodiments of the present invention through a series of at least seven iterations. It should be noted that the catheter openings are not shown in three of the illustrated embodiments in FIG. 46, but those embodiments would include either a circular passageway or flexible tab opening or any other suitable opening or passageway for receiving a catheter tube therethrough.

FIG. 47 shows a perspective view of another embodiment of the present invention generally based upon those shown in FIG. 46. The external catheter stabilization device 601 is preferably comprised of substantially soft and flexible medically approved thermoplastic elastomer (TPE). In this example embodiment, the entire device is preferably molded or may be optionally 3-D printed as a single piece part or component of a selected generally homogenous material throughout.

Medically approved grades of TPE materials are designed and intended to be as chemically inert as possible for continued use and contact with human skin. Therefore, the selection of medical grade TPE helps to minimize the potential for patient skin irritation and any resulting discomfort or further medical complications to the patient.

Optionally, the external catheter stabilization device 601 may comprise, for example, more than one grade of medically compatible thermoplastic elastomer (TPE) by means of an injection molding or 3-D printing process. This can provide the advantages of allowing the use of various grades of material including respective degrees of elasticity or rigidity for example, where the structural characteristics and requirements of the device can be better optimized. Likewise, the use of other types and grades for polymers or plastics, such as for example medically compatible high or low density polyethylene, can be further incorporated into areas that are not in continuous contact with the patient's skin, but provide the desired or preferred mechanical or structural characteristics that help to achieve optimal designs, functionality and ability to manufacture in an evolving technology industrial production environment. Other means of manufacture may include or incorporate, for example, the various metals and special alloys, room temperature vulcanization (RTV) materials, chemical adhesives, ultrasonic welding, laser welding, and use of 3-D printable water-soluble materials to facilitate the design and manufacturing of various final products related to the present invention.

As shown in FIGS. 47, 48, 48A, 48B, and 48C, external catheter stabilization device 601 includes a generally "football-shaped" hollow oval, elongated or elliptically-shaped hollow base 602 that further includes longitudinal ends or paddles 603 and 604. Hollow base 602 further includes a pair of longitudinal end portions or paddles 603 and 604 extending from generally opposite ends of hollow base 602 and therefore provide bottom support surfaces 603b and 604b for the device 601 as it makes contact with the skin at or over the location of the stoma for example. Bottom surfaces 603b and 604b provide primary surfaces support and stability for device 601. Preferably in one embodiment, strips of medical tape (not shown) are placed over the paddles 603 and 604 at upper support surfaces 603a and 604a and onto the skin of the patient to secure and stabilized the device 601 at its intended location over the stoma.

Paddle upper transition surfaces 603c and 604c may be preferably provided as a fillet radius or angled chamfer at the upper edge portions of longitudinal securing paddles 603 and 604. These provide a smoother transition for the medical adhesive tape as it is applied to the surface of the patient's skin, over the paddle upper support surfaces 603a and 603b and back onto the surface of the patient's skin at each end of the device 601, respectively.

Optionally, paddle bottom edge transition radii may be provided at and along edges 603d and 604d as best shown in FIGS. 48B and 48C. Various dimensions of radii may be selected and incorporated by design to help smooth and lessen what otherwise could be a relatively sharp edge in contact with the patient's skin, thus helping to reduce the potential for irritation and discomfort when the device 601 is secured to the patient's skin for extended periods.

Optionally, medical adhesive (not shown) may be manually applied to the bottom support surfaces 603b and 604b just prior to the placement of the device 601 onto the surface of the patient's skin. Further optionally, a medical adhesive may be pre-applied (not shown) at bottom support surfaces 603b and 604b. In this case, a pre-applied medical adhesive may be installed in a controlled production manufacturing setting, whereby "peel and stick" methods of installation of the device 601 can offer the user increased ease-of-use and convenience. By design, or at the option of the user, both medical tape and "peel and stick" methods of securing the device can be utilized at the same time for added stability and security of device 601 on the surface of the patient's skin.

Base central opening 605 provides an open passageway for the flexible catheter tube 610 (not shown in FIGS. 47, 48, 48A, 48B, 48C) to pass through. In this embodiment, the opening is preferably an oval or elliptical shape. This shape allows a for a partially free and slidable friction fit of a flexible catheter tube 610 through base central opening 605. Additionally, this shape, including the elastic characteristics of the materials involved, can provide a degree of forgiveness with regard to at least a limited range of standard catheter diameter sizes (e.g., Fr. 8, 10, 12, 14, etc.). This design feature offers a further degree of forgiveness and adaptability as the catheter diameters may vary slightly as a function of manufacturing tolerance variation between different manufacturers, which may slightly vary within one selected nominal size of catheter. Other optional geometric shapes for the base central opening 605, including those presented in the other embodiments of the present invention may be incorporated into the design as preferred.

As best shown in FIGS. 47, 48, 48B, and 48C, substantially semi-circular lateral openings are provided at the sides of external catheter stabilizer device 601. These lateral openings are also shown in a number of the other embodiments of the present invention. The substantially semi-circular lateral openings 606a and 606b provide access to the interior portion 602a of the generally elliptically shaped hollow base 602, thus providing at least partial visibility and at least partial access to the stoma, surrounding skin, and tissues surrounding the stoma area; without the necessity of having to remove the external catheter stabilization device 601 in every instance.

Additionally, the lateral openings 606a and 606b provide for the free passage of airflow to the stoma area and immediate surrounding skin and tissues which can help promote good health and healing. Further, these openings provide a passageway for irrigation of the skin and tissues with water, saline solutions, other medical treatment fluids, and the like; again to help promote medical serviceability of the stoma and immediate surrounding tissues without the necessity of having to remove the external catheter stabilization device 601 in every instance.

Finally, the substantially semi-circular lateral openings 606a and 606b provide for a convenient shape and contour for both the thumb and forefinger of the user respectively, whenever it becomes necessary to grasp and stabilize the external catheter stabilization device 601. This can often occur for example when (a) first installing the device 601 onto the patients skin with medical adhesive tape or the like, (b) grasping the device when checking for the tightness, stability and security of the device 601 when it is in place on the patient's skin, (c) grasping and supporting the device 601 when it is necessary to install, adjust, or remove a catheter, (d) changing or adjusting the configuration or mode of operation of the device 601 when selectively allowing the catheter to freely drain fluids or otherwise controllably stopping the free flow of fluids through the installed catheter.

As shown in FIGS. 47, 48, 48A, and 48B, the external catheter stabilization device 601 of the present invention includes a bendable upper portion 607 comprised of the same thermoplastic elastomer (TPE) as previously described. Bendable upper portion 607 is attached to the generally elliptically shaped hollow base 602 by two resilient and bendable hinge sections or retainer elements 607a and 607b. In this case, the cross sections of bendable hinge sections 607a and 607b are approximately square or rectangular, however other cross sectional shapes are may be used such as round, oval, or other shapes as preferred allowing substantially free and repeated reverse directional bending of the material without causing early onset of mechanical failure due to material fatigue. In instances where thermoplastic elastomer (TPE) is being used, the cross-sectional shape of the hinge sections 607a and 607b is not critical.

Bendable upper portion 607 includes an upper central portion 607c that further includes an elliptical or oval-shaped upper portion passageway opening 607d. Upper portion passageway opening 607d is generally aligned with base central opening 605 when in the vertical position shown allowing a flexible catheter tube 610 (not shown) to be slidably inserted through the entire device 601. Upper portion passageway opening 607d is very similar in shape and size to base central opening 605 providing similar advantages as previously described and allowing for a partially free and slidable light friction fit of a flexible catheter tube 610 through both respective passageways at the same time.

As best shown in FIGS. 47, 48, and 48B, upper central portion 607c of bendable upper portion 607 further includes an upper portion rectangular protrusion 607f which is approximately square or rectangular in cross section, extending approximately the full lateral width of the bendable upper portion 607, and extending horizontally and outwardly to one side from bendable upper portion 607. The purpose of upper portion rectangular protrusion 607f is to contribute to effectively pinching off or blocking the flow of fluid in the substantially flexible catheter tube 610 when the device 601 is configured for no-flow mode of operation. Examination of the following figures and views will help make the function and purpose of protrusion 607f more apparent.

As best shown in FIGS. 47, 48, 48A and 48B, wedge-block or protrusion 608 extends upward from the top portion of generally elliptically shaped hollow base 602. The sharp pointed top of wedge-block 608 points upward and extends laterally in width just between and off to one side of bendable hinge sections 607a and 607. The purpose of wedge-block 608 is to work in conjunction with upper portion rectangular protrusion 607f to engage the tube and to contribute toward effectively pinching off or blocking the flow of fluid through the substantially flexible catheter tube 610 when the device 601 is configured for no-flow mode of operation. Examination of the following figures and views will help make the function and purpose of wedge-block 608 more readily understood.

As best shown in FIGS. 47, 48, 48A and 48B, free-flow hold-down strap 609a and no-flow hold-down strap 609b (or hooks or other elements that are configured to receive the tube and/or the flexible retainer element or bendable hinge section) are respectively attached to the upper end portions of generally elliptically shaped hollow base 602. Free-flow hold-down strap 609a and no-flow hold-down strap 609b are comprised of the same resilient and significantly elastic thermoplastic elastomer (TPE) as previously described. In this case, free-flow hold-down strap 609a and no-flow hold-down strap 609b maintain the characteristic of acting much like rubber bands; able to generate a retractive force as they attempt to return to their original shape.

When device 601 is configured for free-flow mode of operation, upper central portion 607c (including the flexible catheter tube 610 (not shown)) is engaged through and under free-flow hold-down strap 609a. Alternately, when device 601 is configured for no-flow mode of operation, upper central portion 607 (including flexible catheter tube (not shown)) is engaged through and under no-flow hold-down strap 609b. In each of the two modes of operation, the hold-down straps 609a and 609b generally and securely hold the upper central portion 607c (including the flexible catheter tube (not shown)) downward and substantially tightly against generally elliptically shaped hollow base 602. Examination of the following figures and views will help make the function and purpose of the hold-down straps 609a and 609b more readily understood.

FIGS. 49, 50, 50A, 50B, and 50C show the external catheter stabilization device 601 configured for free-flow mode of operation, with upper central portion 607c (including the flexible catheter tube 610 (not shown for clarity)) is engaged through and under free-flow hold-down strap 609a.

FIGS. 51, 52, 52A, 52B, and 52C show the external catheter stabilization device 601 configured for no-flow mode of operation. With upper central portion 607c (including the flexible catheter tube 610 (not shown for clarity)) is engaged through and under no-flow hold-down strap 609b.

FIGS. 53, 54, 54A, and 54B show the external catheter stabilization device 601 configured with an example flexible section of flexible catheter tube 610 passing through the central portion of the device at base central opening 605 and through upper portion passageway opening 607d of upper central portion 607c. This mode of operation can be regarded as "the initial installation configuration" of the device 601, where the flexible catheter tube 610 has been just installed. Additionally, once the catheter has been installed in such a way and the device 601 has been taped and secured into place, including extending the flexible catheter tube 610 through the stoma and into the bladder, this arrangement provides the patient with free-flow operation, stability and control of the catheter to completely, quickly and readily drain the bladder (for example) into a container or the like whenever needed.

FIGS. 55, 56, 56A, 56B, and 56C show the external catheter stabilization device 601 configured with an example section of flexible catheter tube 610 passing through the central portion of the device at base central opening 605 and through upper portion passageway opening 607d of upper central portion 607c. This mode of operation can be generally defined and regarded as having "the flexible catheter secured for continuous night-time free-flow and drainage of the bladder" (for example). To achieve this mode of operation, generally the "out-flow end" of the flexible catheter tube 610 is routed under and through the free-flow hold-down strap 609. The flexible catheter tube 610 is then carefully pulled through and outward until the upper central portion 607c tilts and bends over in self-alignment for engagement under the free-flow hold-down strap 609a. At this point the top portion of the hold-down strap is pulled and stretched upward (by finger and thumb of one hand while the other hand finger and thumb stabilizes the device 601 by grasping the semi-circular lateral openings 606a and 606b) and onto the upper central portion 607, thus securing both the upper central portion 607c and catheter into place.

FIGS. 57, 58, 58A, 58B, and 58C again show the external catheter stabilization device 601 configured with an example section of flexible catheter tube 610 passing through the central portion of the device at base central opening 605 and through upper portion passageway opening 607d of upper central portion 607c. This mode of operation can be generally defined and regarded as "the flexible catheter secured for continuous blocked or no-flow" from the bladder (for example). To achieve this mode of operation, generally the "out-flow end" of the flexible catheter tube 610 is routed under and through the no-flow hold-down strap 609b. The flexible catheter tube 610 is then carefully pulled through and outward until the upper central portion 607c tilts and bends over in self-alignment for engagement under the no-flow hold-down strap 609b. At this point the top portion of the hold-down strap is pulled and stretched upward (by finger and thumb of one hand while the other hand finger and thumb stabilizes the device 601 by grasping the semi-circular lateral openings 606a and 606b) and onto the upper central portion 607, thus securing both the upper central portion 607c and the flexible catheter tube 610 into place.

As best approximately shown in FIGS. 57, 58, 58A, and 58B, this configuration and mode of operation the device 601 and shows how the flexible catheter tube 610 is effectively and sharply bent over and pinched closed between upper portion rectangular protrusion 607f and wedge-block 608, preventing free-flow of fluid from the bladder through the flexible catheter tube 610 when the device is configured for or adjusted or set to the no-flow mode of operation.

Free flow of the bladder (for example) can again be achieved when desired by returning the device 601 and flexible catheter tube 610 to either of the other two modes of operation or configurations; that shown in FIG. 53 generally described as being "the initial installation configuration" or that shown in FIG. 55 being generally described as being "the flexible catheter secured for continuous night-time free-flow and drainage of the bladder" (for example).

FIG. 59 is a perspective view of a simplified embodiment of the external catheter stabilization device 701 like those shown in FIG. 46. The purpose in this example is to establish further design options and improvements related more specifically to the longitudinal securing paddles 703 and 704.

FIG. 59A is a top plan view of a first basic longitudinal securing paddles design of FIG. 59 similar to those shown in many of the embodiments of the present invention. The dimensions shown may serve as a general baseline example for discussion. Dimension L1 is a center-to-center distance between the generally circular ends of the longitudinal paddles 703 and 704. Dimension L2 is the overall length, Dimension D1 is the width of the inner portion of the longitudinal securing paddles 703 and 704, dimension R1 is the radius of the circular portion of the longitudinal paddles. Generally, the longitudinal paddles are symmetrical as shown, however it is optional to provide non-symmetrical or asymmetrical longitudinal securing paddles to satisfy, for example, a particular design specification for a particular product application.

FIG. 59B is a side elevation of a first basic longitudinal paddles design of FIG. 59, showing for example dimension T1 representing the thickness of the longitudinal paddles. In this example, the thickness T1 is relatively thin. For example, when the external catheter stabilization device is taped and secured onto the skin, dimension F2 represents the hold-down force of the adhesive tape, while dimension F1 represents an anticipated upward pull force that, for example, might be expected from an upward pulling of a flexible catheter tube (not shown) during typical use. The relatively thin section of material at cross-section S1 could allow considerable undesired shear and torsional deflection of the generally elliptically shaped hollow base 702 relative to the surface of the skin. This may contribute to any excess instability and deflections of the device 701 at the surface of the skin of a patient during use.

FIG. 59C is a bottom plan view of a first basic longitudinal paddles design of FIG. 59 showing dimension A1 representing the surface contact area available at bottom support surface 703b.

FIG. 60 is a perspective view of a simplified embodiment of the external catheter stabilization device 701' like those shown in FIG. 46. The purpose in this example is to establish further design options and improvements related more specifically to the longitudinal securing paddles 703 and 704.

FIG. 60A is a top plan view of a second basic longitudinal securing paddles design of FIG. 60 like those shown in many of the embodiments of the present invention. The dimensions shown may serve as a general baseline example for discussion. Dimension L3 is a center-to-center distance between the generally circular ends of the longitudinal paddles 703 and 704. In this case, dimension L3 has been increased by approximately 6% over dimension L1 in previous FIG. 59A. The dimension L4, the overall length, has been increased approximately 10% over dimension L2 in previous FIG. 59A. Dimension D2 is the width of the inner portion of the longitudinal securing paddles 703 and 704. In this case, dimension D2 has not significantly changed from dimension D1 in FIG. 59A. Dimension R2 is the radius of the circular portion of the longitudinal securing paddles 703 and 704. In this case, dimension R2 has increased by approximately 30% over dimension R1 in FIG. 59A. By means of these modest dimensional increases, the available contact surface area A2 of FIG. 60C is increased by approximately 50% over that of area A1 in FIG. 59C. It may be noted that that these values refer to one end of the device 701'. The advantage of this change is the significant increase in the paddle bottom support surfaces areas 703b and 704a for a modest increase in the overall size of the device 701'. This can be a significant factor when securing the device 701' to the surface of the patent's skin using either medical tape or medical adhesive.

Again generally, the longitudinal paddles are symmetrical as shown, however it is optional to provide non-symmetrical or asymmetrical longitudinal securing paddles to satisfy, for example, a particular design specification for a particular product application.

FIG. 60B is a side elevation of the second basic longitudinal paddles design of FIG. 60 like those shown in many of the embodiments of the present invention. In this example, the thicknesses of the longitudinal securing paddles 703 and 704 shown by dimension T3 has been increased by approximately a factor of 3 from dimension T1 in FIG. 59B at the transition section between the longitudinal securing paddles 703, 704 and the generally elliptically shaped hollow base 702. This dimensional change provides a significant improvement in both shear and torsional deflection resistance at cross-section S2 over that of cross-section S1 of FIG. 59B.

Additionally, FIG. 60B shows a tapering reduction in thickness of longitudinal securing paddles 703 and 704 at the outermost ends, generally defined by dimension T2 and the example angle dimension "3.6 degrees typ." The advantage of this feature is to help minimize a step transition between the respective paddle upper support surfaces 703a and 704a and the skin when medical adhesive tape is used to secure the device 701' to the surface of the patient's skin.

FIG. 61 is a perspective view of a simplified embodiment showing another device 701" having a third longitudinal paddles design similar to that shown in previous FIGS. 60, 60A, 60B, and 60C. As shown in FIGS. 61A, 61B, 61C, and detail FIG. 61D, top relief channels 703e and 704e and bottom relief channels 703f and 704f have been added to provide a dedicated flex-joint or "plastic hinge" by design at the transition between the longitudinal securing paddles 703 and 704, and the generally elliptically shaped hollow base 702. By design specification per specific application, radii dimensions RT and RB can be selected along with selection of dimension D5 to accurately control the desired amount of relative flexibility of the device depending upon the characteristics of the selected material and the desired degree of flexibility of the overall device 701".

FIG. 62, is a perspective view of a simplified embodiment showing another device 701'" having a fourth longitudinal paddles design where attention is directed to paddle upper transition surfaces 703c and 704c, and paddle bottom edge transition radii 703d and 704d. Generally, FIGS. 62A, 62B, 62C, and detail FIG. 62D show dimension R3 which may represent a selected radius dimension to further improve the step transition from respective paddle upper support surfaces 703a and 704a and the surface of the patient's skin. This is particularly helpful when medical adhesive tape is used to secure the device 701'" to the surface of the patient's skin. Selected radius dimension R3 may be replaced by other geometric shapes, such as for example, a chamfer of a specified angle and length dimension to provide paddle upper transition surfaces 703c and 704c. Combinations of various transition surface shapes and geometry along the various portions of the device 701'" may also be selected as preferred.

Likewise, as best shown in FIG. 62B and detail view 62D, paddle bottom edge transition radius 703d and 704d may show dimension R4 which may represent a selected radius dimension to further improve or eliminate any potentially abrupt relatively sharp corner along the bottom outer edges of external catheter stabilization device 701'". This feature can help reduce the likelihood of the device 701'" causing potential irritation or discomfort at the surface of the skin of a patient using the device 701'".

FIG. 63 is a perspective view of a simplified embodiment showing another device 801 having a fifth longitudinal paddles design. FIG. 63A, section detail view FIG. 63B, detail view FIG, 63C, bottom plan view FIG. 63D, bottom perspective view FIG. 63E and detail view FIG. 63F show an example feature modification for paddle bottom support surfaces 803b and 804b. This feature modification is comprised of an array or series of relief channels or air circulation grooves 803g and 803h, a first set of grooves 803g set perpendicular (for example) to a second set of grooves 803h. The size and orientation of the grooves are selected to provide preferred and desired degree of air-flow or air circulation through and under the longitudinal securing paddles between the device 801 and the surface of the skin of the patient using the device. The contours of the relief channels are preferably smooth with no or minimal sharp edges to further reduce the potential for irritation or discomfort at the surface of the skin of a patient using the device 801. By preferred design, medical adhesive tape or medical adhesive may be selected to secure the device 801 to the skin of the patient while continuing to allow air circulation once in place. Additionally, the design of the contoured surfaces or grooves 803g, 803h, 804g, and 804h may provide increased grip and stability of the device as it contacts the surface of the skin with minimal potential irritation or discomfort to the patient.

Additionally, and as shown in FIG. 63E, the design of the contoured surfaces or grooves 803g, 803h, 804g, and 804h are also intended to provide passageways for irrigation of the skin and tissues with water, saline solutions, other medical treatment fluids, and the like; to help promote medical serviceability of the areas under and near the device 801, the stoma (for example) and immediate surrounding skin and tissues without the necessity of having to remove the external catheter stabilization device 301 in every instance.

FIG. 64 is a perspective view of a simplified embodiment showing an example of a catheter stabilization device 901 with a catheter disinfectant wiper arrangement of the present invention. FIG. 64A shows and exploded assembly of the disinfectant wiper insert 902 and wiper holder 903. FIG. 64B is a side elevation of FIG. 64. FIG. 64C is a cross-section view of FIG. 64B showing the general arrangement of components when assembled. FIG. 64D is a detail view of FIG. 64C and shows external catheter stabilization device internal groove 901a, into which wiper holder external ridge 903a engages to secure the wiper holder 903 in place. Wiper holder stop ring 903b prevents the wiper holder 903 from traveling too far upward when being assembled and pressed into place. Disinfectant wiper external ridge 902a engages with insert holder internal groove 903c to secure disinfectant wiper insert 902 in place.

Disinfectant wiper insert 902 is preferably comprised of semi-porous or similar sponge-like foam material such that is able to maintain a liquid film of disinfectant. When sliding the catheter downward into the stoma, the inherent wiping action of wiper blades 902b can serve as a deterrent against bacteria which may be present on the surface of the flexible catheter tube (not shown).

The inside diameter of wiper central opening 902c can be selected by design for specific diameter sizes of catheters. Since the wiper insert 902 and the wiper holder 903 are both inserts, various sizes of inserts can be assembled into the main body of the external catheter stabilization device 901. This level of interchangeability offers advantages in reducing the number of larger molded components in the manufacturing setting.

While this example of interchangeability relies upon "snap-in" ridges and grooves for securing the components, other means of assembly and fastening are anticipated without affecting the scope and claims of the present invention.

FIG. 65 is a perspective view of a simplified embodiment showing an example catheter disinfectant wiper tool. This example provides an alternative embodiment to the "built-in" disinfectant wiper arrangement previously described. As the flexible catheter tube is moved up or down within the external catheter stabilization device 911, the catheter disinfectant wiper tool 921 is pushed onto the flexible catheter tube 910 under the external catheter stabilization device 911 to provide disinfectant wiping action of the catheter 910. As best shown in FIGS. 65A and 65B, a split at one side of the replaceable wiper insert 922 facilitates this procedure. FIG. 65B is an exploded perspective view of the replaceable disinfectant wiper insert and wiper holding tool 923.

With reference to FIGS. 66, 67 and 67A-C, the external catheter stabilization device 601' is similar to device 601 discussed above with respect to FIGS. 47-58C, and is configured with a flexible section of the flexible catheter tube passing through the central portion of the device at base central opening 605 and through the flexible retainer 607 and through the upper portion passageway opening 607d of the upper central portion 607c, such as in a similar manner as discussed above. This mode of operation can be regarded as "the initial installation configuration" of the device 601', where the flexible catheter tube has been just installed. Additionally, once the catheter has been installed in such a way and the device 601' has been taped and secured into place, including extending the flexible catheter tube through the stoma and into the bladder, this arrangement provides the patient with free-flow operation, stability and control of the catheter to completely, quickly and readily drain the bladder (for example) into a container or the like whenever needed. Because device 601' is similar to device 601, discussed above, a detailed description of the devices need not be repeated herein.

Device 601' includes rectangular openings 606c at the walls or supports to provide enhanced air flow at the stoma site. The device 601' also includes filled-in areas 603e and 604e (FIG. 67C) for increased contact surface area for use with applied adhesives. Optionally, the device 601' may include holes 612 for suturing the device to the skin.

Additionally, the device 601' has increased contact area at the respective paddles 603 and 604 through increased diameters for increased contact surface area for use with applied adhesives. The hold-down loops 609a and 609b have slightly larger openings to allow a catheter with a slightly larger plastic end connection to route-through more easily by the user. This is helpful whenever modes of operation and the position of the catheter (flow/no-flow) are switched. Alternate catheter clamping systems or designs (such as open ended hooks that readily receive the tube into) are further envisioned that may avoid having to "thread" the end portion of the catheter tube through the respective hold-down loops 609a, 609b each time the mode of operation is switched.

Also, the device 601' generally demonstrates the structural material transition between the paddles 603, 604 and the main body 602, where the material transition has been smoothed from the previous designs. This relates to improving the relative rigidity or stability of the device when held in place on the skin with either medical tape or pre-applied medical adhesives (see FIGS. 59 through 62C for example).

The stability of the device and its functionality may depend at least in part on the relative hardness (or flexibility) of the plastic material (e.g., TPE or other suitable material)

that is used to mold or form the device. For example, the selected TPE material may have around a Shore A scale hardness range of between around 8 and 85 throughout. Optionally, a different hardness grade of material may be selected that is either softer or harder depending upon the desired product performance characteristics and specifications.

For applications where a softer and more pliable and flexible material is selected, parts of the device may comprise the softer material and other parts (that require additional rigidity) may be made out of a harder material, such as via a two shot molding process or overmolding process or the like. For example, if the triangular element 608 ended-up being too soft to fully and consistently engage the catheter and cut or restrict the flow through the catheter, a slightly stiffer material may be used for that particular feature during the manufacturing process. For example, the triangular element may be molded and the rest of the device may be overmolded over a portion of the triangular element. Thus, various stiffnesses and grades of TPE (or other suitable material) may be utilized throughout the one-piece molded or 3-D printed device to achieve the desired performance characteristics of the device and invention.

Additionally, the structural characteristics of the device may be adjusted as desired without the necessity of having to change the physical design or shape of the device itself every time (within a practical range of uses). For example, use of composite materials or different grades of hardness or TPE in the same device could offer the advantage of avoiding having to create new injection molds each time different performance (stiffness versus flexibility) characteristics are needed.

Various embodiments of the present invention are shown in the drawings using similar reference numbers, but with the appropriate or respective first digit to correspond to the description of the devices above. Each embodiment may include aspects of other embodiments where applicable.

Thus, the present invention provides an external catheter stabilizer device that can stabilize and retain a tube at a patient. Surgical drains are used in a wide variety of different types of surgeries, primarily to remove pus, blood, or other fluids from inside the body. The intention of a drain is to decompress or drain either fluid or air from the area of surgery. Tubes/catheters are used to transport the fluid from inside the body to outside the body. The purpose of the external catheter stabilizer device is to allow access of a tube or catheter into the body, to stabilize the tube or catheter outside of the body, all while allowing for the doctor, patient and/or caregiver the ability to observe and inspect the site of the stoma with minimal physical disturbance to the site.

Instead of being an indwelling catheter, the external catheter stabilizer device sits or is stationed on the outside of the body and allows a catheter to pass through it for any kind of stoma regardless of location or purpose. The external catheter stabilizer device limits or prevents stomal stenosis after a surgery where a stoma was created in the body and keeps the passageway into the body open until it heals while maintaining drainage if and when needed. The purpose of the hook or secure hold-down straps on the external catheter stabilizer device is to hold the catheter in place without the catheter being pulled out prematurely, preventing stomal stenosis. Any time a patient/doctor is going to be using a catheter or a similar device to drain fluids from the body, the external catheter stabilizer device allows the catheter to remain fixed in the body, at the depth desired, eliminating the need for multiple new catheter uses at each instance of use. One of the biggest advantages to the use of the external catheter stabilizer device is to ensure that the drain tube is secured. Inadvertent or accidental dislodgment of the catheter at the stoma site can significantly increase the risk of infection and irritation to the surrounding skin. The external catheter stabilizer device will significantly help ensure that the drain is secured and the catheter system is intact, limiting or preventing or avoiding dislodgment, infection, or irritation of surrounding skin. This, along with the ability to visually monitor the stoma, will significantly decrease the likelihood of post-operative management complications, specifically infections.

With the external catheter stabilizer device, a straight catheter would be placed through the center hole of the device and into the body through the stoma. The catheter would be able to go directly into the bladder and drain it. After the bladder has been drained, the catheter can be pulled back, still in place within the stoma, and locked into place using the hook or secure hold-down straps on the external catheter stabilizer device. If the patient needed to keep the catheter in the bladder for continual draining, the catheter would stay in the bladder and be locked into place using the hook or the secure hold-down straps of the external catheter stabilizer device. While draining, the catheter is able to keep the stoma from closing and prevent bladder spasms. Without the need for and complete absence of a Foley catheter balloon, frequent pain and considerable discomfort to the patient can be entirely avoided. The external catheter stabilizer device gives the option of keeping the catheter in the bladder for continual drainage or it allows the catheter to be pulled back out of the bladder, but staying or remaining just within the passageway of stoma, keeping it open until the stoma and passageway has fully healed.

Current solutions for all the problems herein covered and generally described either have separate or alternate devices offering their own particular disadvantages or they simply do not exist. The external catheter stabilizer device solves all of them at the same time. The Foley Catheter remains stationary within the bladder and cannot be removed until the balloon is deflated. It works well to keep the stoma open while it heals and allows the bladder to be drained, but the balloon in the bladder can cause major bladder spasms in the time that it is in place. There are other catheter stabilizers, but they are not placed over the stoma site which gives ample opportunity and an increased risk for the catheter to be accidentally pulled out or disturbed. The external catheter stabilizer device of the present invention could possibly save a patient from having to secure and utilize as many as 10 brand new catheters a day if they were previously using the L-stint method. Beyond the significant health benefits, the external catheter stabilizer device can represent a substantial improvement toward ease of care of the patient, the efforts of patient care staff workers, medical care costs and other necessary and related resources.

Changes and modifications in the specifically described embodiments can be carried out without departing from the principles of the invention, which is intended to be limited only by the scope of the appended claims, as interpreted according to the principles of patent law including the doctrine of equivalents.

The invention claimed is:
1. A method for stabilizing a tube at a stoma of a patient and for controlling fluid flow through the tube, the method comprising:
providing a stabilizing device having a base portion and a tube holding portion having a passageway therethrough that is configured to receive the tube, wherein the tube holding portion is attached to the base portion via at least two spaced apart legs;

affixing the base portion at the stoma of the patient, wherein, with the base portion affixed at the patient, the tube holding portion is spaced from the patient;

receiving the tube through the passageway of the tube holding portion;

adjusting the tube holding portion to position the tube in a free-flow orientation whereby fluid can flow through the tube, and retaining the tube in the free-flow orientation via a free-flow retaining element of the stabilizing device; and adjusting the tube holding portion to position the tube in a restricted-flow orientation by bending the tube to pinch the tube at the stabilizing device to limit fluid flow therethrough, and retaining the tube in the restricted-flow orientation via a restricted-flow retaining element of the stabilizing device.

2. The method of claim 1, wherein adjusting the tube holding portion to position the tube in the restricted-flow orientation comprises bending the tube so that the restricted-flow retaining element and a protrusion of the stabilizing device cooperate to pinch the tube to limit fluid flow therethrough.

3. The method of claim 1, wherein the tube holding portion comprises a flexible element that is attached to the base portion, and wherein adjusting the tube holding portion to position the tube in the free-flow orientation comprises flexing the flexible element in one direction to bend the tube toward the free-flow orientation, and wherein adjusting the tube holding portion to position the tube in the restricted-flow orientation comprises flexing the flexible element in another direction to bend the tube toward the restricted-flow orientation.

4. The method of claim 3, wherein retaining the tube in the free-flow orientation is via the free-flow retaining element disposed at one portion of the stabilizing device, and wherein retaining the tube in the restricted-flow orientation is via the restricted-flow retaining element disposed at another portion of the stabilizing device.

5. The method of claim 4, wherein retaining the tube in the free-flow orientation comprises receiving a portion of the tube in the free-flow retaining element to retain the tube holding portion and the tube in the free-flow orientation, and wherein retaining the tube in the restricted-flow orientation comprises receiving the portion of the tube in the restricted-flow retaining element to retain the tube holding portion and the tube in the restricted-flow orientation.

6. The method of claim 4, wherein a protrusion is disposed at the other portion of the stabilizing device, and wherein flexing the flexible element in the other direction bends the tube toward the restricted-flow orientation so that the restricted-flow retaining element and the protrusion of the stabilizing device cooperate to pinch the tube to limit fluid flow therethrough.

7. A method for stabilizing a tube at a stoma of a patient, the method comprising:

providing a stabilizing device having a base portion and a tube holding portion having a passageway therethrough that is configured to receive the tube, wherein the tube holding portion is attached to the base portion via at least two spaced apart legs;

affixing the base portion at the stoma of the patient, wherein, with the base portion affixed at the patient, the tube holding portion is spaced from the patient;

receiving the tube through a wiping element disposed at the passageway of the tube holding portion, wherein the wiping element is retained at the passageway via a retaining lip that circumscribes the wiping element and that engages a corresponding retaining lip of the tube holding portion at the passageway; and wiping the tube via the wiping element as the tube is inserted through the passageway and into the stoma of the patient.

8. The method of claim 7, wherein the wiping element comprises a disinfecting surface that wipes and disinfects the tube as the tube is inserted through the passageway.

9. The method of claim 8, wherein the wiping element comprises a semi-porous material that retains a disinfectant at the disinfecting surface.

10. The method of claim 7, wherein the wiping element is removably disposed at the passageway.

11. The method of claim 7, wherein the wiping element comprises a partial ring that is disposed at least partially around the tube via moving the wiping element transverse to a longitudinal axis of the tube so that the tube is received in the wiping element.

12. The method of claim 11, comprising moving the wiping element into engagement with the tube via a wiper tool that receives the wiping element therein and that is at least partially open along one end to allow for the tube to be received in the wiping element.

13. A method for stabilizing a tube at a stoma of a patient, the method comprising:

providing a stabilizing device having a base portion and a tube holding portion having a passageway therethrough that is configured to receive the tube, wherein the tube holding portion is attached to the base portion via at least two spaced apart legs;

wherein the base portion comprises (i) at least two pads that are configured to contact the patient, and (ii) a flexible polymeric element that couples each of the pads to a distal end of a respective leg via to allow for adjustment of the pads relative to the legs;

wherein the legs comprise a first plastic material and the flexible polymeric elements comprise a second plastic material, and wherein the second plastic material is more flexible than the first plastic material;

adjusting the pads relative to the legs and affixing the pads at the stoma of the patient, wherein, with the pads affixed at the patient, the tube holding portion is spaced from the patient; and receiving the tube through the passageway of the tube holding portion.

14. The method of claim 13, wherein the at least two spaced apart legs comprises three spaced apart legs.

15. The method of claim 13, wherein one of the legs includes a tube retaining element for retaining the tube at the stabilizing device.

16. The method of claim 15, wherein the tube retaining element comprises a receiving element that is configured to releasably receive the tube therein.

17. A method for stabilizing a tube at a stoma of a patient, the method comprising:

providing a stabilizing device having a base portion and a tube holding portion having a passageway therethrough that is configured to receive the tube, wherein the tube holding portion is attached to the base portion via at least two spaced apart legs;

wherein the base portion comprises (i) at least two pads that are configured to contact the patient, and (ii) a flexible polymeric element that couples each of the pads to a distal end of a respective leg via to allow for adjustment of the pads relative to the legs;

wherein one of the legs includes a tube retaining element for retaining the tube at the stabilizing device;

wherein the tube retaining element comprises a receiving element that is configured to releasably receive the tube therein;

wherein the receiving element is integrally formed with one of the legs, and wherein the tube, when received in the receiving element, is at or below an upper surface of the leg at the receiving element;

adjusting the pads relative to the legs and affixing the pads at the stoma of the patient, wherein, with the pads affixed at the patient, the tube holding portion is spaced from the patient; and receiving the tube through the passageway of the tube holding portion.

18. A method for stabilizing a tube at a stoma of a patient and for controlling fluid flow, the method comprising:

providing a stabilizing device having a base portion and a tube holding portion having a passageway therethrough that is configured to receive the tube, wherein the tube holding portion is attached to the base portion via at least two spaced apart legs;

wherein the tube holding portion comprises a plurality of flexible tabs each having a first end attached to a hub of the tube holding portion at the passageway and a distal second end protruding radially inwardly into the passageway;

wherein the flexible tabs are flexible between an initial state, where the flexible tabs cooperate to establish a first effective diameter of the passageway, and an expanded state, where the flexible tabs cooperate to establish a second effective diameter of the passageway that is larger than the first effective diameter, and wherein the flexible tabs are biased toward the initial state;

affixing the base portion at the patient at a stoma of the patient, wherein, with the base portion affixed at the patient, the tube holding portion is spaced from the patient;

with the base portion affixed at the patient at the stoma, inserting the tube through the passageway of the tube holding portion, wherein, with the tube inserted into the passageway, the flexible tabs deflect toward the expanded state to enlarge the passageway toward the second effective diameter to receive the tube in the passageway; and retaining the tube in the passageway at least in part via the flexible tabs being biased toward the initial state so as to engage the tube received in the passageway.

19. The method of claim 18, wherein each of the flexible tabs comprises a curved inner surface, and wherein the flexible tabs cooperate to form a cylindrical passageway for receiving the tube therein.

20. The method of claim 18, wherein the tube holding portion comprises at least three flexible tabs.

21. The method of claim 18, wherein one of the legs includes a tube retaining element for retaining the tube at the stabilizing device.

22. The method of claim 21, wherein the tube retaining element comprises a receiving element that is configured to releasably receive the tube therein, and wherein the tube, when received in the receiving element, is at or below an upper surface of the leg at the receiving element.

* * * * *

UNITED STATES PATENT AND TRADEMARK OFFICE
CERTIFICATE OF CORRECTION

PATENT NO. : 11,684,754 B2  
APPLICATION NO. : 15/929464  
DATED : June 27, 2023  
INVENTOR(S) : Sarah L. Olson et al.

Page 1 of 1

It is certified that error appears in the above-identified patent and that said Letters Patent is hereby corrected as shown below:

In the Claims

<u>Column 30</u>  
Claim 18, Line 4 "at the patient at a stoma" should be --at the stoma--

Signed and Sealed this  
Twenty-fifth Day of July, 2023

Katherine Kelly Vidal  
*Director of the United States Patent and Trademark Office*